United States Patent
White

(10) Patent No.: US 11,725,205 B2
(45) Date of Patent: Aug. 15, 2023

(54) METHODS AND POLYNUCLEOTIDES FOR AMPLIFYING A TARGET POLYNUCLEOTIDE

(71) Applicant: Oxford Nanopore Technologies PLC, Oxford (GB)

(72) Inventor: James White, Oxford (GB)

(73) Assignee: Oxford Nanopore Technologies PLC, Oxford (GB)

( * ) Notice: Subject to any disclaimer, the term of this patent is extended or adjusted under 35 U.S.C. 154(b) by 343 days.

(21) Appl. No.: 16/412,346

(22) Filed: May 14, 2019

(65) Prior Publication Data

US 2020/0032248 A1 Jan. 30, 2020

(30) Foreign Application Priority Data

May 14, 2018 (GB) .................................. 1807793

(51) Int. Cl.
| | | |
|---|---|---|
| C12N 15/10 | (2006.01) | |
| C07H 21/04 | (2006.01) | |
| C12N 15/11 | (2006.01) | |
| C12N 15/66 | (2006.01) | |

(52) U.S. Cl.
CPC ......... *C12N 15/1065* (2013.01); *C07H 21/04* (2013.01); *C12N 15/1031* (2013.01); *C12N 15/111* (2013.01); *C12N 15/66* (2013.01); *C12N 2310/122* (2013.01)

(58) Field of Classification Search
CPC ............ C12N 15/1065; C12N 15/1031; C12N 15/111; C12N 15/66; C12N 2310/122; C07H 21/04; C12Q 1/6853; C12Q 1/6869; C12Q 1/6806
See application file for complete search history.

(56) References Cited

U.S. PATENT DOCUMENTS

| | | | |
|---|---|---|---|
| 5,215,899 A | 6/1993 | Dattagupta | |
| 5,424,413 A | 6/1995 | Hogan et al. | |
| 5,561,043 A | 10/1996 | Cantor et al. | |
| 5,714,320 A | 2/1998 | Kool | |
| 5,777,078 A | 7/1998 | Bayley et al. | |
| 5,795,782 A | 8/1998 | Church et al. | |
| 5,817,771 A | 10/1998 | Bayley et al. | |
| 5,866,328 A | 2/1999 | Bensimon et al. | |
| 5,866,336 A | 2/1999 | Nazarenko et al. | |
| 5,985,834 A | 11/1999 | Engel et al. | |
| 6,015,714 A | 1/2000 | Baldarelli et al. | |
| 6,087,099 A | 7/2000 | Gupte et al. | |
| 6,123,819 A | 9/2000 | Peeters | |
| 6,127,166 A | 10/2000 | Bayley et al. | |
| 6,251,610 B1 | 6/2001 | Gupte et al. | |
| 6,274,320 B1 | 8/2001 | Rothberg et al. | |
| 6,362,002 B1 | 3/2002 | Denison et al. | |
| 6,403,319 B1 | 6/2002 | Lizardi et al. | |
| 6,426,231 B1 | 7/2002 | Bayley et al. | |
| 6,451,563 B1 | 9/2002 | Wittig et al. | |
| 6,451,593 B1 | 9/2002 | Wittig et al. | |
| 6,465,193 B2 | 10/2002 | Akeson et al. | |
| 6,498,023 B1 | 12/2002 | Abarzua | |
| 6,627,067 B1 | 9/2003 | Branton et al. | |
| 6,709,861 B2 | 3/2004 | Mead et al. | |
| 6,787,308 B2 | 9/2004 | Balasubramanian et al. | |
| 6,824,659 B2 | 11/2004 | Bayley et al. | |
| 6,863,833 B1 | 3/2005 | Bloom et al. | |
| 6,916,665 B2 | 7/2005 | Bayley et al. | |
| 6,927,070 B1 | 8/2005 | Bayley et al. | |
| 7,087,729 B1 | 8/2006 | Prive | |
| 7,189,503 B2 | 3/2007 | Akeson et al. | |
| 7,238,485 B2 | 7/2007 | Akeson et al. | |
| 7,361,466 B2 | 4/2008 | Korlach et al. | |
| 7,507,575 B2 | 3/2009 | Bedingham et al. | |
| 7,700,281 B2 | 4/2010 | Kubu et al. | |

(Continued)

FOREIGN PATENT DOCUMENTS

| | | |
|---|---|---|
| CN | 101495656 | 7/2009 |
| CN | 102245760 | 11/2011 |

(Continued)

OTHER PUBLICATIONS

Gill et al. (Nucleosides, Nucleotides, and Nucleic Acids, 27:p. 224-243, 2008).*
Notomi et al. (Nucleic Acids Research, 2000, vol. 28, No. 12, e63, 7 pages).*
Akeson et al., Microsecond time-scale discrimination among polycytidylic acid, polyadenylic acid, and polyuridylic acid as homopolymers or as segments within single RNA molecules. Biophys J. Dec. 1999;77(6):3227-33.
Altschul et al., Basic local alignment search tool. J Mol Biol. Oct. 5, 1990;215(3):403-10.
Altschul, A protein alignment scoring system sensitive at all evolutionary distances. J Mol Evol. Mar. 1993;36(3):290-300.

(Continued)

*Primary Examiner* — Robert H Havlin
(74) *Attorney, Agent, or Firm* — Wolf, Greenfield & Sacks, P.C.

(57) ABSTRACT

A method of amplifying a target polynucleotide, comprising: providing a template polynucleotide comprising a 5' hairpin, a target polynucleotide and a 3' hairpin, wherein the 5' hairpin comprises one or more non-canonical nucleotides; and contacting the template polynucleotide with a polymerase and canonical nucleotides, wherein the polymerase extends, using the canonical nucleotides, the target polynucleotide from its 3' end to form a first extended polynucleotide comprising the 5' hairpin at its 5' end and the complement of the 5' hairpin at its 3' end, wherein the complement of the 5' hairpin forms a 3' hairpin; and the polymerase extends the first extended polynucleotide from its 3' end to form a second extended polynucleotide comprising the 5' hairpin at its 5' end and the complement of the 5' hairpin at its 3' end, wherein the complement of the 5' hairpin forms a 3' hairpin.

10 Claims, 17 Drawing Sheets

Specification includes a Sequence Listing.

(56) References Cited

U.S. PATENT DOCUMENTS

| | | |
|---|---|---|
| 7,745,116 B2 | 6/2010 | Williams |
| 8,105,846 B2 | 1/2012 | Bayley et al. |
| 8,143,030 B2 | 3/2012 | Maxham et al. |
| 8,153,375 B2 | 4/2012 | Travers et al. |
| 8,343,746 B2 | 1/2013 | Rank et al. |
| 8,383,369 B2 | 2/2013 | Maxham et al. |
| 8,628,940 B2 | 1/2014 | Sorenson et al. |
| 8,652,779 B2 | 2/2014 | Turner et al. |
| 8,785,211 B2 | 7/2014 | Bayley et al. |
| 8,822,160 B2 | 9/2014 | Bayley et al. |
| 8,889,348 B2 | 11/2014 | Ju |
| 9,057,102 B2 | 6/2015 | Turner et al. |
| 9,116,118 B2 | 8/2015 | Turner et al. |
| 9,145,623 B2 | 9/2015 | Kavanagh et al. |
| 9,150,918 B2 | 10/2015 | Turner et al. |
| 9,542,527 B2 | 1/2017 | Travers et al. |
| 9,546,400 B2 | 1/2017 | Turner et al. |
| 9,551,023 B2 | 1/2017 | Turner et al. |
| 9,556,480 B2 | 1/2017 | Turner et al. |
| 9,582,640 B2 | 2/2017 | Travers et al. |
| 9,600,626 B2 | 3/2017 | Travers et al. |
| 9,670,526 B2 | 6/2017 | Kokoris et al. |
| 9,678,056 B2 | 6/2017 | Turner et al. |
| 9,738,929 B2 | 8/2017 | Turner et al. |
| 9,957,560 B2 | 5/2018 | Brown et al. |
| 10,131,944 B2 | 11/2018 | Bernick et al. |
| 10,221,450 B2 | 3/2019 | Heron et al. |
| 10,227,632 B2 | 3/2019 | Jarvius |
| 10,570,440 B2 | 2/2020 | White et al. |
| 10,597,713 B2 | 3/2020 | Brown et al. |
| 10,669,578 B2 | 6/2020 | Clarke et al. |
| 10,851,409 B2 | 12/2020 | Brown et al. |
| 11,155,860 B2 | 10/2021 | White et al. |
| 11,168,363 B2 | 11/2021 | Brown et al. |
| 11,186,857 B2 | 11/2021 | Stoddart et al. |
| 11,261,487 B2 | 3/2022 | Brown et al. |
| 11,352,664 B2 | 6/2022 | Mckeown |
| 11,390,904 B2 | 7/2022 | White |
| 2001/0039039 A1 | 11/2001 | Weissman et al. |
| 2002/0028458 A1 | 3/2002 | Lexow |
| 2002/0094526 A1 | 7/2002 | Bayley et al. |
| 2002/0098530 A1 | 7/2002 | Pfeifer et al. |
| 2002/0132350 A1 | 9/2002 | Suzuki et al. |
| 2002/0142331 A1 | 10/2002 | Fu et al. |
| 2002/0177701 A1 | 11/2002 | Weissman et al. |
| 2002/0197618 A1 | 12/2002 | Sampson |
| 2003/0044816 A1 | 3/2003 | Denison et al. |
| 2003/0059778 A1 | 3/2003 | Berlin et al. |
| 2003/0087232 A1 | 5/2003 | Christians et al. |
| 2003/0099951 A1 | 5/2003 | Akeson et al. |
| 2003/0108902 A1 | 6/2003 | Abarzua |
| 2003/0118595 A1 | 6/2003 | Niemeyer et al. |
| 2003/0165936 A1 | 9/2003 | Rabbani et al. |
| 2003/0166137 A1 | 9/2003 | Zuker et al. |
| 2003/0211502 A1 | 11/2003 | Sauer et al. |
| 2003/0215881 A1 | 11/2003 | Bayley et al. |
| 2004/0055901 A1 | 3/2004 | Petersen et al. |
| 2004/0214177 A1 | 10/2004 | Bension |
| 2004/0229315 A1 | 11/2004 | Lee et al. |
| 2005/0042633 A1 | 2/2005 | Williams |
| 2005/0053961 A1 | 3/2005 | Akeson et al. |
| 2005/0142559 A1 | 6/2005 | Makrigiorgos |
| 2005/0221316 A1 | 10/2005 | Pedersen et al. |
| 2005/0227239 A1 | 10/2005 | Joyce |
| 2005/0260655 A1 | 11/2005 | Liu et al. |
| 2006/0063171 A1 | 3/2006 | Akeson et al. |
| 2006/0086626 A1 | 4/2006 | Joyce |
| 2006/0141516 A1 | 6/2006 | Kobold et al. |
| 2006/0292611 A1 | 12/2006 | Berka et al. |
| 2007/0015182 A1 | 1/2007 | Abarzua |
| 2007/0020640 A1 | 1/2007 | McCloskey |
| 2007/0031857 A1 | 2/2007 | Makarov et al. |
| 2007/0122885 A1 | 5/2007 | Reeves et al. |
| 2007/0224613 A1 | 9/2007 | Strathmann |
| 2007/0269825 A1 | 11/2007 | Wang et al. |
| 2007/0287151 A1 | 12/2007 | Linnarsson |
| 2008/0108082 A1 | 5/2008 | Rank et al. |
| 2008/0166724 A1 | 7/2008 | Gerber et al. |
| 2008/0206252 A1 | 8/2008 | Pennica et al. |
| 2008/0311582 A1 | 12/2008 | Bayley et al. |
| 2009/0098612 A1 | 4/2009 | Rhee et al. |
| 2009/0191598 A1 | 7/2009 | Ruan et al. |
| 2009/0256116 A1 | 10/2009 | Shumaker-Parry et al. |
| 2009/0269771 A1 | 10/2009 | Schroeder |
| 2009/0280538 A1 | 11/2009 | Patel et al. |
| 2009/0298075 A1 | 12/2009 | Travers et al. |
| 2010/0003560 A1 | 1/2010 | Shibata |
| 2010/0035254 A1 | 2/2010 | Williams |
| 2010/0035260 A1 | 2/2010 | Olasagasti et al. |
| 2010/0075309 A1 | 3/2010 | Maxham et al. |
| 2010/0075327 A1 | 3/2010 | Maxham et al. |
| 2010/0075328 A1 | 3/2010 | Bjornson et al. |
| 2010/0092960 A1 | 4/2010 | Fehr |
| 2010/0120098 A1 | 5/2010 | Grunenwald et al. |
| 2010/0121582 A1 | 5/2010 | Pan et al. |
| 2010/0221212 A1 | 9/2010 | Stagliano et al. |
| 2010/0221716 A1 | 9/2010 | Flusberg et al. |
| 2010/0276588 A1 | 11/2010 | Syms |
| 2010/0331194 A1 | 12/2010 | Turner et al. |
| 2011/0019186 A1 | 1/2011 | Himmelhaus et al. |
| 2011/0124518 A1 | 5/2011 | Cantor |
| 2011/0136676 A1 | 6/2011 | Greene |
| 2011/0214991 A1 | 9/2011 | Kim et al. |
| 2011/0224106 A1 | 9/2011 | Eshoo et al. |
| 2011/0281768 A1 | 11/2011 | Travers et al. |
| 2011/0287435 A1 | 11/2011 | Grunenwald et al. |
| 2011/0311965 A1 | 12/2011 | Maglia et al. |
| 2012/0010085 A1 | 1/2012 | Rava et al. |
| 2012/0015821 A1 | 1/2012 | Raymond |
| 2012/0058468 A1 | 3/2012 | Mckeown |
| 2012/0100530 A1 | 4/2012 | Moysey et al. |
| 2012/0107802 A1 | 5/2012 | Stoddart et al. |
| 2012/0196279 A1 | 8/2012 | Underwood et al. |
| 2012/0244525 A1 | 9/2012 | Hendrickson |
| 2013/0017978 A1 | 1/2013 | Kavanagh et al. |
| 2013/0078624 A1 | 3/2013 | Holmes et al. |
| 2013/0143802 A1 | 6/2013 | Chilkoti |
| 2013/0195908 A1 | 8/2013 | Leonetti et al. |
| 2013/0203123 A1 | 8/2013 | Nelson et al. |
| 2013/0327644 A1 | 12/2013 | Turner et al. |
| 2014/0134618 A1 | 5/2014 | Kokoris et al. |
| 2014/0134629 A1 | 5/2014 | Turner et al. |
| 2014/0186823 A1 | 7/2014 | Clarke et al. |
| 2014/0206842 A1 | 7/2014 | Majeed et al. |
| 2014/0262784 A1 | 9/2014 | Clarke et al. |
| 2014/0296089 A1 | 10/2014 | Holmes et al. |
| 2014/0308661 A1 | 10/2014 | Holmes et al. |
| 2015/0008126 A1 | 1/2015 | Maglia et al. |
| 2015/0045257 A1 | 2/2015 | Kavanagh et al. |
| 2015/0152492 A1 | 6/2015 | Brown et al. |
| 2015/0167075 A1 | 6/2015 | Turner et al. |
| 2015/0175663 A1 | 6/2015 | Yokoi et al. |
| 2015/0197796 A1 | 7/2015 | White et al. |
| 2015/0218629 A1 | 8/2015 | Heron et al. |
| 2015/0265994 A1 | 9/2015 | Hyde et al. |
| 2015/0285781 A1 | 10/2015 | Heron et al. |
| 2015/0307934 A1 | 10/2015 | Turner et al. |
| 2016/0010147 A1 | 1/2016 | Heron et al. |
| 2016/0010148 A1 | 1/2016 | Turner et al. |
| 2016/0011169 A1 | 1/2016 | Turner et al. |
| 2016/0194677 A1 | 7/2016 | Stoddart et al. |
| 2016/0257942 A1 | 9/2016 | Bruce et al. |
| 2016/0281159 A1 | 9/2016 | Brown et al. |
| 2016/0362739 A1 | 12/2016 | Brown et al. |
| 2017/0002406 A1 | 1/2017 | Bowen et al. |
| 2017/0067101 A1 | 3/2017 | Clarke et al. |
| 2017/0240955 A1 | 8/2017 | White |
| 2017/0314062 A1 | 11/2017 | Kokoris et al. |
| 2017/0321266 A1 | 11/2017 | Mckeown |
| 2018/0030506 A1 | 2/2018 | Fujioka |
| 2018/0051277 A1* | 2/2018 | Godfrey ............ C12Q 1/6855 |
| 2018/0291440 A1 | 10/2018 | Mckeown |
| 2018/0291441 A1 | 10/2018 | Brown et al. |
| 2019/0194722 A1 | 6/2019 | Stoddart et al. |

(56) References Cited

U.S. PATENT DOCUMENTS

| | | | |
|---|---|---|---|
| 2019/0211390 | A1 | 7/2019 | Heron et al. |
| 2019/0376132 | A1 | 12/2019 | Mckeown |
| 2020/0002761 | A1 | 1/2020 | Mckeown |
| 2020/0024655 | A1 | 1/2020 | Brown et al. |
| 2020/0109396 | A1* | 4/2020 | Tsai ............... C12Q 1/6806 |
| 2020/0291452 | A1 | 9/2020 | White |
| 2020/0318179 | A1 | 10/2020 | Clarke et al. |
| 2022/0127669 | A1 | 4/2022 | Brown et al. |
| 2022/0145383 | A1 | 5/2022 | White et al. |
| 2022/0186274 | A1 | 6/2022 | Stoddart et al. |

FOREIGN PATENT DOCUMENTS

| | | | |
|---|---|---|---|
| DE | 112016000293 T5 | 9/2017 | |
| EP | 2682460 A1 | 1/2014 | |
| EP | 3470529 A1 | 4/2019 | |
| GB | 2130219 | 5/1984 | |
| GB | 2237390 | 5/1991 | |
| GB | 2453377 | 4/2009 | |
| JP | H11-137260 | 5/1999 | |
| JP | 2012-506704 A | 3/2012 | |
| WO | WO 1994/23065 | 10/1994 | |
| WO | WO 1999/05167 | 2/1999 | |
| WO | WO 2000/28312 | 5/2000 | |
| WO | WO 2001/40516 | 6/2001 | |
| WO | WO 2001/42782 | 6/2001 | |
| WO | WO 2001/59453 | 8/2001 | |
| WO | WO 2002/42496 | 5/2002 | |
| WO | WO 2003/095669 | 11/2003 | |
| WO | WO 2005/056750 | 6/2005 | |
| WO | WO 2005/068656 A1 | 7/2005 | |
| WO | WO 2005/118877 | 12/2005 | |
| WO | WO 2005/124888 | 12/2005 | |
| WO | WO 2006/020775 | 2/2006 | |
| WO | WO 2006/028508 | 3/2006 | |
| WO | WO 2006/100484 | 9/2006 | |
| WO | WO 2007/057668 | 5/2007 | |
| WO | WO 2007/075987 | 7/2007 | |
| WO | WO 2007/084103 | 7/2007 | |
| WO | WO 2007/114693 A2 | 10/2007 | |
| WO | WO 2007/146158 | 12/2007 | |
| WO | WO 2008/045575 | 4/2008 | |
| WO | WO 2008/083554 | 7/2008 | |
| WO | WO 2008/102120 | 8/2008 | |
| WO | WO 2008/102121 | 8/2008 | |
| WO | WO 2008/124107 | 10/2008 | |
| WO | WO 2009/035647 | 3/2009 | |
| WO | WO 2009/044170 A1 | 4/2009 | |
| WO | WO 2009/077734 A2 | 6/2009 | |
| WO | WO 2009/120372 A2 | 10/2009 | |
| WO | WO 2009/120374 A2 | 10/2009 | |
| WO | WO 2010/004265 | 1/2010 | |
| WO | WO 2010/004273 | 1/2010 | |
| WO | WO 2010/030683 A1 | 3/2010 | |
| WO | WO 2010/034018 | 3/2010 | |
| WO | WO 2010/048605 A1 | 4/2010 | |
| WO | WO 2010/051773 | 5/2010 | |
| WO | WO 2010/086602 A1 | 8/2010 | |
| WO | WO 2010/086603 | 8/2010 | |
| WO | WO 2010/086622 | 8/2010 | |
| WO | WO 2010/094040 | 8/2010 | |
| WO | WO 2010/109107 A1 | 9/2010 | |
| WO | WO 2010/109197 | 9/2010 | |
| WO | WO 2010/122293 | 10/2010 | |
| WO | WO 2010/146349 A1 | 12/2010 | |
| WO | WO 2011/067559 | 6/2011 | |
| WO | WO 2012/033524 A2 | 3/2012 | |
| WO | WO 2012/061832 | 5/2012 | |
| WO | WO 2012/083249 A2 | 6/2012 | |
| WO | WO 2012/098561 A2 | 7/2012 | |
| WO | WO 2012/098562 A2 | 7/2012 | |
| WO | WO 2012/103545 A1 | 8/2012 | |
| WO | WO 2012/107778 A2 | 8/2012 | |
| WO | WO 2012/164270 A1 | 12/2012 | |
| WO | WO 2013/014451 A1 | 1/2013 | |
| WO | WO 2013/041878 A1 | 3/2013 | |
| WO | WO 2013/057495 A2 | 4/2013 | |
| WO | WO 2013/098561 A1 | 7/2013 | |
| WO | WO 2013/098562 A2 | 7/2013 | |
| WO | WO 2013/131962 A1 | 9/2013 | |
| WO | WO 2013/153359 A1 | 10/2013 | |
| WO | WO 2013/185137 A1 | 12/2013 | |
| WO | WO 2014/013259 A1 | 1/2014 | |
| WO | WO 2014/013260 A1 | 1/2014 | |
| WO | WO 2014/013262 A1 | 1/2014 | |
| WO | WO 2014/108810 A2 | 7/2014 | |
| WO | WO 2014/135838 A1 | 9/2014 | |
| WO | WO 2014/153408 A1 | 9/2014 | |
| WO | WO 2015/022544 A1 | 2/2015 | |
| WO | WO 2015/031909 A1 | 3/2015 | |
| WO | WO 2015/055981 A2 | 4/2015 | |
| WO | WO 2015/056028 A1 | 4/2015 | |
| WO | WO 2015/110777 A1 | 7/2015 | |
| WO | WO 2015/110813 A1 | 7/2015 | |
| WO | WO 2015/189636 A1 | 12/2015 | |
| WO | WO 2015/200609 A1 | 12/2015 | |
| WO | WO 2016/003814 A1 | 1/2016 | |
| WO | WO 2016/022557 A1 | 2/2016 | |
| WO | WO 2016/028887 A1 | 2/2016 | |
| WO | WO 2016/059363 A1 | 4/2016 | |
| WO | WO 2017/215500 A1 | 12/2017 | |

OTHER PUBLICATIONS

Amblard et al., Cu(I)-catalyzed Huisgen azide-alkyne 1,3-dipolar cycloaddition reaction in nucleoside, nucleotide, and oligonucleotide chemistry. Chem Rev. Sep. 2009;109(9):4207-20. doi: 10.1021/cr9001462.

Ashkenasy et al., Recognizing a single base in an individual DNA strand: a step toward DNA sequencing in nanopores. Angew Chem Int Ed Engl. Feb. 18, 2005;44(9):1401-4.

Ashkenasy et al., Single Nucleobase Sensitivity of a-Hemolysin (a-HL) Transmembrane Protein Pore: Toward Single DNA Sequencing. ACS National Meeting. 2005;45(13), Abstract No. 74.

Astier et al., Stochastic detection of motor protein-RNA complexes by single-channel current recording. Chemphyschem. Oct. 22, 2007;8(15):2189-94.

Astier et al., Toward single molecule DNA sequencing: direct identification of ribonucleoside and deoxyribonucleoside 5'-monophosphates by using an engineered protein nanopore equipped with a molecular adapter. J Am Chem Soc. Feb. 8, 2006;128(5):1705-10.

Avrameas, Coupling of enzymes to proteins with glutaraldehyde. Use of the conjugates for the detection of antigens and antibodies. Immunochemistry. Jan. 1969;6(1):43-52.

Bayley et al., Stochastic sensors inspired by biology. Nature. Sep. 13, 2001;413(6852):226-30.

Bayley, Sequencing single molecules of DNA. Curr Opin Chem Biol. Dec. 2006;10(6):628-37. Epub Nov. 20, 2006.

Benner et al., Sequence-specific detection of individual DNA polymerase complexes in real time using a nanopore. Nat Nanotechnol. Nov. 2007;2(11):718-24. doi: 10.1038/nnano.2007.344. Epub Oct. 28, 2007.

Berger et al., Universal bases for hybridization, replication and chain termination. Nucleic Acids Res. Aug. 1, 2000;28(15):2911-4.

Bowie et al., Deciphering the message in protein sequences: tolerance to amino acid substitutions. Science. Mar. 16, 1990;247(4948):1306-10.

Braha et al., Carriers versus adapters in stochastic sensing. Chemphyschem. May 2005;6(5):889-92.

Braha et al., Designed protein pores as components for biosensors. Chem Biol. Jul. 1997;4(7):497-505.

Branton et al., The potential and challenges of nanopore sequencing. Nat Biotechnol. Oct. 2008;26(10):1146-53. doi:10.1038/nbt.1495.

Braslavsky et al., Sequence information can be obtained from single DNA molecules. Proc Natl Acad Sci U S A. Apr. 1, 2003;100(7):3960-4. Epub Mar. 21, 2003.

(56) References Cited

OTHER PUBLICATIONS

Budanova et al., Heptakis(6-amino-6-deoxy)-beta-cyclodextrin as a chiral selector for the separation of anionic analyte enantiomers by capillary electrophoresis. Electrophoresis. Aug. 2004;25(16):2795-800.

Burgess et al., Possible dissociation of the heparin-binding and mitogenic activities of heparin-binding (acidic fibroblast) growth factor-1 from its receptor-binding activities by site-directed mutagenesis of a single lysine residue. J Cell Biol. Nov. 1990;111(5 Pt 1):2129-38.

Busam, Structure of *Escherichia coli* exonuclease I in complex with thymidine 5'-monophosphate. Acta Crystallogr D Biol Crystallogr. Feb. 2008;64(Pt 2):206-10. doi: 10.1107/S090744490706012X. Epub Jan. 16, 2008.

Butler et al., Determination of RNA orientation during translocation through a biological nanopore. Biophys J. Jan. 1, 2006;90(1):190-9. Epub Oct. 7, 2005.

Butler et al., Single-molecule DNA detection with an engineered MspA protein nanopore. Proc Natl Acad Sci U S A. Dec. 30, 2008;105(52):20647-52. doi: 10.1073/pnas.0807514106. Epub Dec. 19, 2008.

Case 1:17-cv-00275-LPS Document 18. Notice of subsequent events relating to Oxford's motion to dismiss (D.I. 9). Oct. 18, 2017.

Case 1:17-cv-00275-LPS Document 19. Oxford Nanopore Technologies, Inc.'s response to Pacific Biosciences of California, Inc.'s notice of subsequent events. Oct. 24, 2017.

Case 1:17-cv-00275-RGA Document 10. Oxford's opening brief in support of its motion to dismiss PacBio's complaint for patent infringement. May 8, 2017.

Case 1:17-cv-00275-RGA Document 14. PacBio's response to Oxford's motion to dismiss. Jun. 5, 2017.

Case 1:17-cv-00275-RGA Document 16. Oxford's reply brief in support of its motion to dismiss PacBio's complaint for patent infringement. Jun. 26, 2017.

Case 1:17-cv-01353-LPS Document 13. First Amended Complaint for Patent Infringement. Nov. 30, 2017.

Case 1:17-cv-01353-LPS Document 15. Plaintiff's response to Oxford Nanopore Techologies, Inc.'s Motion to Dismiss and Request for Scheduling Conference. Nov. 30, 2017.

Case 1:17-cv-01353-RGA Document 10. Oxford's opening brief in support of its motion to partially dismiss Pacbio's complaint for patent infringement. Nov. 16, 2017.

Chan, Advances in sequencing technology. Mutat Res. Jun. 3, 2005;573(1-2):13-40.

Cheley et al., A functional protein pore with a "retro" transmembrane domain. Protein Sci. Jun. 1999;8(6):1257-67.

Cheley et al., A genetically encoded pore for the stochastic detection of a protein kinase. Chembiochem. Dec. 2006;7(12):1923-7.

Cheley et al., Spontaneous oligomerization of a staphylococcal alpha-hemolysin conformationally constrained by removal of residues that form the transmembrane beta-barrel. Protein Eng. Dec. 1997;10(12):1433-43.

Cheley et al., Stochastic sensing of nanomolar inositol 1,4,5-trisphosphate with an engineered pore. Chem Biol. Jul. 2002;9(7):829-38.

Chen et al., Atomic Layer Deposition to Fine-Tune the Surface Properties and Diameters of Fabricated Nanopores. Nano Lett. Jun. 25, 2004;4(7):1333-1337.

Chen et al., Outer membrane protein G: Engineering a quiet pore for biosensing. Proc Natl Acad Sci U S A. Apr. 29, 2008;105(17):6272-7. doi: 10.1073/pnas.0711561105. Epub Apr. 28, 2008.

Cheng, et al., Functional characterization of the multidomain F plasmid TraI relaxase-helicase. J Biol Chem. Apr. 8, 2011;286(14):12670-82. doi: 10.1074/jbc.M110.207563. Epub Feb. 2, 2011.

Clarke et al., Continuous base identification for single-molecule nanopore DNA sequencing. Nat Nanotechnol. Apr. 2009;4(4):265-70. doi: 10.1038/nnano.2009.12. Epub Feb. 22, 2009.

Cockroft et al., A single-molecule nanopore device detects DNA polymerase activity with single-nucleotide resolution. J Am Chem Soc. Jan. 23, 2008;130(3):818-20. doi: 10.1021/ja077082c. Epub Jan. 1, 2008.

Colas et al., Microscopical investigations of nisin-loaded nanoliposomes prepared by Mozafari method and their bacterial targeting. Micron. 2007;38(8):841-7. Epub Jul. 3, 2007.

Comai et al., Protein engineering modulates the transport properties and ion selectivity of the pores formed by staphylococcal gamma-haemolysins in lipid membranes. Mol Microbiol. Jun. 2002;44(5):1251-67.

Comer et al., Microscopic mechanics of hairpin DNA translocation through synthetic nanopores. Biophys J. Jan. 2009;96(2):593-608. doi: 10.1016/j.bpj.2008.09.023.

Cudic et al., Binding of Nucleotides in Water by Phenathridinium Bis(intercaland) Receptor Molecules. J. Chem. Soc., Chem. Commun., pp. 1073-1075 (1995).

Dapprich, Single-molecule DNA digestion by lambda-exonuclease. Cytometry. Jul. 1, 1999;36(3):163-8.

Deamer et al., Characterization of nucleic acids by nanopore analysis. Acc Chem Res. Oct. 2002;35(10):817-25.

Deamer et al., Nanopores and nucleic acids: prospects for ultrarapid sequencing. Trends Biotechnol. Apr. 2000;18(4):147-51.

Derrington et al., Nanopore DNA sequencing with MspA. Proc Natl Acad Sci U S A. Sep. 14, 2010;107(37):16060-5. doi: 10.1073/pnas.1001831107. Epub Aug. 26, 2010.

Devereaux et al., A comprehensive set of sequence analysis programs for the VAX. Nucleic Acids Res. Jan. 11, 1984;12(1 Pt 1):387-95.

Dorre et al., Techniques for single molecule sequencing. Bioimaging, vol. 5:139-152 (1997).

Eid et al., Real-time DNA sequencing from single polymerase molecules. Science. Jan. 2, 2009;323(5910):133-8. doi:10.1126/science.1162986. Epub Nov. 20, 2008.

Eliseev et al., Aminocyclodextrins as Selective Hosts with Several Binding Sites for Nucleotides. Angew. Chem. Int. Ed. Engl., vol. 32(9):1331-1333 (1993).

Eliseev et al., Molecular Recognition of Nucleotides, Nucleosides, and Sugars by Aminocyclodextrins. J. Am. Chem. Soc., vol. 116:6081-6088 (1994).

El-Sagheer et al., Synthesis and polymerase chain reaction amplification of DNA strands containing an unnatural triazole linkage. J Am Chem Soc. Mar. 25, 2009;131(11):3958-64. doi: 10.1021/ja8065896.

Erie et al., A dumbbell-shaped, double-hairpin structure of DNA: a thermodynamic investigation. Biochemistry. Nov. 3, 1987;26(22):7150-9.

Fairman-Williams et al., SF1 and SF2 helicases: family matters. Curr Opin Struct Biol. Jun. 2010;20(3):313-24. doi: 10.1016/j.sbi.2010.03.011. Epub Apr. 22, 2010.

Flomenbom et al., Single stranded DNA translocation through a nanopore: a master equation approach. Phys Rev E Stat Nonlin Soft Matter Phys. Oct. 2003;68(4 Pt 1):041910. Epub Oct. 14, 2003.

Flusberg et al., Direct detection of DNA methylation during single-molecule, real-time sequencing. Nat Methods. Jun. 2010;7(6):461-5. doi: 10.1038/nmeth.1459. Epub May 9, 2010.

Gacillàn-Barcia et al., The diversity of conjugative relaxases and its application in plasmid classification. FEMS Microbiol Rev. May 2009;33(3):657-87.

Genschel et al., Interaction of *E. coli* single-stranded DNA binding protein (SSB) with exonuclease I. The carboxy-terminus of SSB is the recognition site for the nuclease. Biol Chem. Mar. 2000;381(3):183-92.

Gershow et al., Recapturing and trapping single molecules with a solid-state nanopore. Nat Nanotechnol. Dec. 2007;2(12):775-9. doi:10.1038/nnano.2007.381. Epub Dec. 2, 2007.

Ghosal, Electrokinetic-flow-induced viscous drag on a tethered DNA inside a nanopore. Phys Rev E Stat Nonlin Soft Matter Phys. Dec. 2007;76(6 Pt 1):061916. Epub Dec. 26, 2007.

Gonzalez-Perez et al., Biomimetic triblock copolymer membrane arrays: a stable template for functional membrane proteins. Langmuir. Sep. 15, 2009;25(18):10447-50. doi: 10.1021/la902417m.

(56) References Cited

OTHER PUBLICATIONS

Grant et al., A facile method for attaching nitroxide spin labels at the 5' terminus of nucleic acids. Nucleic Acids Res. 2007;35(10):e77. Epub May 21, 2007.
Gu et al., Capture of a single molecule in a nanocavity. Science. Jan. 26, 2001;291(5504):636-40.
Gu et al., Electroosmotic enhancement of the binding of a neutral molecule to a transmembrane pore. Proc Natl Acad Sci U S A. Dec. 23, 2003;100(26):15498-503. Epub Dec. 15, 2003.
Gu et al., Prolonged residence time of a noncovalent molecular adapter, beta-cyclodextrin, within the lumen of mutant alpha-hemolysin pores. J Gen Physiol. Nov. 2001;118(5):481-94.
Gu et al., Reversal of charge selectivity in transmembrane protein pores by using noncovalent molecular adapters. Proc Natl Acad Sci U S A. Apr. 11, 2000;97(8):3959-64.
Gu et al., Single molecule sensing by nanopores and nanopore devices. Analyst. Mar. 2010;135(3):441-51. doi: 10.1039/b907735a. Epub Dec. 22, 2009.
Gu et al., Stochastic sensing of organic analytes by a pore-forming protein containing a molecular adapter. Nature. Apr. 22, 1999;398(6729):686-90.
Guan et al., Stochastic sensing of TNT with a genetically engineered pore. Chembiochem. Oct. 2005;6(10):1875-81.
Han et al., Characterization and optimization of an entropic trap for DNA separation. Anal Chem. Jan. 15, 2002;74(2):394-401.
Han et al., RecJ exonuclease: substrates, products and interaction with SSB. Nucleic Acids Res. Feb. 18, 2006;34(4):1084-91. Print 2006.
Hammerstein et al., Subunit dimers of alpha-hemolysin expand the engineering toolbox for protein nanopores. J Biol Chem. Apr. 22, 2011;286(16):14324-34. doi: 10.1074/jbc.M111.218164. Epub Feb. 15, 2011.
He et al., The T4 Phage SF1B Helicase Dda is Structurally Optimized to Perform DNA Strand Separation. Structure. Jul. 3, 2012; 20(7): 1189-1200. EPub May 31, 2012. doi: 10.1016/j.str.2012.04.013.
Hein et al., Click chemistry, a powerful tool for pharmaceutical sciences. Pharm Res. Oct 2008;25(10):2216-30. doi: 10.1007/s11095-008-9616-1. Epub May 29, 2008.
Henrickson et al., Driven DNA transport into an asymmetric nanometer-scale pore. Phys Rev Lett. Oct. 2, 2000;85(14):3057-60.
Heredia et al., In vitro double transposition for DNA identification. Anal Biochem. Apr. 1, 2010;399(1):78-83. doi: 10.1016/j.ab.2009.11.030. Epub Nov. 26, 2009.
Heron et al., Simultaneous measurement of ionic current and fluorescence from single protein pores. J Am Chem Soc. Feb. 11, 2009;131(5):1652-3. doi: 10.1021/ja808128s.
Hobbs et al., SSB protein limits RecOR binding onto single-stranded DNA. J Biol Chem. Apr. 13, 2007;282(15):11058-67. Epub Feb. 1, 2007.
Holden et al., Direct introduction of single protein channels and pores into lipid bilayers. J Am Chem Soc. May 11, 2005;127(18):6502-3.
Holden et al., Functional bionetworks from nanoliter water droplets. J Am Chem Soc. Jul. 11, 2007;129(27):8650-5. Epub Jun. 16, 2007.
Hornblower et al., Single-molecule analysis of DNA-protein complexes using nanopores. Nat Methods. Apr. 2007;4(4):315-7. Epub Mar. 4, 2007.
Howorka et al., DNA Duplex Formation of Individual DNA Strands within a Single Protein Pore. Biophysical Journal, vol. 82{1, pt. 2):508a, No. 2482-Plat (2002).
Howorka et al., Improved protocol for high-throughput cysteine scanning mutagenesis. Biotechniques. Nov. 1998;25(5):764-6, 768, 770 passim.
Howorka et al., Kinetics of duplex formation for individual DNA strands within a single protein nanopore. Proc Natl Acad Sci U S A. Nov. 6, 2001;98(23):12996-3001. Epub Oct. 23, 2001.
Howorka et al., Probing distance and electrical potential within a protein pore with tethered DNA. Biophys J. Dec. 2002;83(6):3202-10.
Howorka et al., Sequence-specific detection of individual DNA strands using engineered nanopores. Nat Biotechnol. Jul. 2001;19(7):636-9.
Hu et al., Theory of DNA translocation through narrow ion channels and nanopores with charged walls. Phys Rev E Stat Nonlin Soft Matter Phys. Sep. 2008;78(3 Pt 1):032901. Epub Sep. 10, 2008.
Hwang et al., Electrical behavior of droplet interface bilayer networks: experimental analysis and modeling. J Am Chem Soc. Sep. 26, 2007;129(38):11854-64. Epub Sep. 1, 2007.
Ivanov et al., DNA tunneling detector embedded in a nanopore. Nano Lett. Jan. 12, 2011;11(1):279-85. doi: 10.1021/nl103873a. Epub Dec. 6, 2010.
Jayasinghe et al., The leukocidin pore: evidence for an octamer with four LukF subunits and four LukS subunits alternating around a central axis. Protein Sci. Oct. 2005;14(10):2550-61.
Jung et al., The internal cavity of the staphylococcal alpha-hemolysin pore accommodates approximately 175 exogenous amino acid residues. Biochemistry. Jun. 28, 2005;44(25):8919-29.
Kalisch et al., Covalently linked sequencing primer linkers (splinkers) for sequence analysis of restriction fragments. Gene. 1986;44(2-3):263-70.
Kanan et al., Reaction discovery enabled by DNA-templated synthesis and in vitro selection. Nature. Sep. 30, 2004;431(7008):545-9.
Kang et al., Single protein pores containing molecular adapters at high temperatures. Angew Chem Int Ed Engl. Feb. 25, 2005;44(10):1495-9.
Kasianowicz et al., Characterization of individual polynucleotide molecules using a membrane channel. Proc Natl Acad Sci U S A. Nov. 26, 1996;93(24):13770-3.
Keyser, Controlling molecular transport through nanopores. J R Soc Interface. Oct. 7, 2011;8(63):1369-78. doi: 10.1098/rsif.2011.0222. Epub Jun. 29, 2011.
Khulbe et al., DNA translocation through a-hemolysin nanopores with potential application to macromolecular data storage. Journal Applied Physics, vol. 97(104317):1-7 (2005).
Kocalka et al., Rapid and efficient DNA strand cross-linking by click chemistry. Chembiochem. May 23, 2008;9(8):1280-5. doi:10.1002/cbic.200800006.
Kolb et al., Click Chemistry: Diverse Chemical Function from a Few Good Reactions. Angew Chem Int Ed Engl. Jun. 1, 2001;40(11):2004-2021.
Kovall et al., Toroidal structure of lambda-exonuclease. Science. Sep. 19, 1997;277(5333):1824-7.
Kozarewa et al., 96-plex molecular barcoding for the Illumina Genome Analyzer. Methods Mol Biol. 2011;733:279-98. doi: 10.1007/978-1-61779-089-8_20.
Kozlov et al., Regulation of Single-stranded DNA Binding by the C Termini of *Escherichia coli* Single-stranded DNA-binding (SBB) Protein. J. Biol. Chem. May 28, 2010;285(22):17246-52.
Kumar et al., Nonradioactive labeling of synthetic oligonucleotide probes with terminal deoxynucleotidyl transferase. Anal Biochem. Mar. 1988;169(2):376-82. Erratum in: Anal Biochem Sep. 1988;173(2):469.
Langecker et al., Synthetic lipid membrane channels formed by designed DNA nanostructures. Science. Nov. 16, 2012;338(6109):932-6. doi: 10.1126/science.1225624.
Lazar et al., Transforming growth factor alpha: mutation of aspartic acid 47 and leucine 48 results in different biological activities. Mol Cell Biol. Mar. 1988;8(3):1247-52.
Lee et al., Importance of the conserved CA dinucleotide at Mu termini. J Mol Biol. Nov. 30, 2001;314(3):433-44.
Li et al., DNA molecules and configurations in a solid-state nanopore microscope. Nat Mater. Sep. 2003;2(9):611-5. Epub Aug. 24, 2003.
Lieberman et al., Processive replication of single DNA molecules in a nanopore catalyzed by phi29 DNA polymerase. J Am Chem Soc. Dec. 22, 2010;132(50):17961-72. doi:10.1021/ja1087612. Epub Dec. 1, 2010.
Liu et al., Adding new chemistries to the genetic code. Annu Rev Biochem. 2010;79:413-44. doi: 10.1146/annurev.biochem.052308.105824.
Liu et al., Structure of the DNA repair helicase XPD. Cell. May 30, 2008;133(5):801-12. doi: 10.1016/j.cell.2008.04.029.

(56) References Cited

OTHER PUBLICATIONS

Lohman et al., Non-hexameric DNA helicases and translocases: mechanisms and regulation. Nat Rev Mol Cell Biol. May 2008;9(5):391-401. doi: 10.1038/nrm2394.
Lovett et al., Identification and purification of a single-stranded-DNA-specific exonuclease encoded by the recJ gene of *Escherichia coli*. Proc Natl Acad Sci U S A. Apr. 1989;86(8):2627-31.
Lovrinovic et al., Rapid synthesis of DNA-cysteine conjugates for expressed protein ligation. Biochem Biophys Res Commun. Sep. 30, 2005;335(3):943-8.
Lu et al., Peptide inhibitors identify roles for SSB C-terminal residues in SSB/Exonuclease I complex formation. Biochemistry. Jul. 28, 2009; 48(29): 6764-6771. doi: 10.1021/bi900361r. Author Manuscript.
Lu et al., Structural basis of *Escherichia coli* single-stranded DNA-binding protein stimulation of exonuclease I. Proc Natl Acad Sci U S A. Jul. 8, 2008;105(27):9169-74. doi: 10.1073/pnas. 0800741105. Epub Jun. 30, 2008.
Luo et al., Influence of polymer-pore interactions on translocation. Phys Rev Lett. Oct. 5, 2007;99(14):148102. Epub Oct. 1, 2007.
Lutz et al., Efficient construction of therapeutics, bioconjugates, biomaterials and bioactive surfaces using azide-alkyne "click" chemistry. Adv Drug Deliv Rev. Jun. 10, 2008;60(9):958-70. doi: 10.1016/j.addr.2008.02.004. Epub Mar. 4, 2008.
Ma et al., Bright functional rotaxanes. Chem Soc Rev. Jan. 2010;39(1):70-80. doi: 10.1039/b901710k. Epub Jul. 21, 2009.
Maglia et al., Analysis of single nucleic acid molecules with protein nanopores. Methods Enzymol. 2010;475:591-623. doi: 10.1016/S0076-6879(10)75022-9.
Maglia et al., Enhanced translocation of single DNA molecules through alpha-hemolysin nanopores by manipulation of internal charge. Proc Natl Acad Sci U S A. Dec. 16, 2008;105(50):19720-5. doi:10.1073/pnas.0808296105. Epub Dec. 5, 2008.
Martin et al., Nanoscale protein pores modified with PAMAM dendrimers. J Am Chem Soc. Aug. 8, 2007;129(31):9640-9. Epub Jul. 18, 2007.
Martínez et al., The mRNA cap structure stimulates rate of poly(A) removal and amplifies processivity of degradation. J Biol Chem. Jul. 27, 2001;276(30):27923-9. Epub May 18, 2001.
Marziali et al., New DNA sequencing methods. Annu Rev Biomed Eng. 2001;3:195-223.
Mathé et al., Orientation discrimination of single-stranded DNA inside the alpha-hemolysin membrane channel. Proc Natl Acad Sci U S A. Aug. 30, 2005;102(35):12377-82. Epub Aug. 19, 2005.
Matsuura et al., Real-time observation of a single DNA digestion by lambda exonuclease under a fluorescence microscope field. Nucleic Acids Res. Aug. 15, 2001;29(16):E79.
Meller et al., Rapid nanopore discrimination between single polynucleotide molecules. Proc Natl Acad Sci U S A. Feb. 1, 2000;97(3):1079-84.
Meller et al., Single molecule measurements of DNA transport through a nanopore. Electrophoresis. Aug. 2002;23(16):2583-91.
Meller, Dynamics of polynucleotide transport through nanometre-scale pores. Journal Physics: Condensed Matter, vol. 15:R581-R607 (2003).
Merzlyak et al., Conductance and ion selectivity of a mesoscopic protein nanopore probed with cysteine scanning mutagenesis. Biophys J. Nov. 2005;89(5):3059-70. Epub Aug. 5, 2005.
Miles et al., Single molecule sensing with solid-state nanopores: novel materials, methods, and applications. Chem Soc Rev. Jan. 7, 2013;42(1):15-28. doi: 10.1039/c2cs35286a. Epub Sep. 19, 2012.
Miner et al., Molecular barcodes detect redundancy and contamination in hairpin-bisulfite PCR. Nucleic Acids Res. 2004; 32(17): e135. EPub Sep. 30, 2004. doi: 10.1093/nar/gnh132.
Mitchell et al., Chemical tags facilitate the sensing of individual DNA strands with nanopores. Angew Chem Int Ed Engl. 2008;47(30):5565-8. doi:10.1002/anie.200800183.
Mohammad et al., Controlling a single protein in a nanopore through electrostatic traps. J Am Chem Soc. Mar. 26, 2008;130(12):4081-8. doi: 10.1021/ja710787a. Epub Mar. 6, 2008.

Mol et al., Structure and function of the multifunctional DNA-repair enzyme exonuclease III. Nature. Mar. 23, 1995;374(6520):381-6.
Montal et al., Formation of bimolecular membranes from lipid monolayers and a study of their electrical properties. Proc Natl Acad Sci U S A. Dec. 1972;69(12):3561-6.
Movileanu et al., Detecting protein analytes that modulate transmembrane movement of a polymer chain within a single protein pore. Nat Biotechnol. Oct. 2000;18(10):1091-5.
Movileanu et al., Location of a constriction in the lumen of a transmembrane pore by targeted covalent attachment of polymer molecules. J Gen Physiol. Mar. 2001;117(3):239-52.
Muller et al., DNA-directed assembly of artificial multienzyme complexes. Biochem Biophys Res Commun. Dec. 5, 2008;377(1):62-7. doi:10.1016/j.bbrc.2008.09.078. Epub Sep. 25, 2008.
Nakane et al., A nanosensor for transmembrane capture and identification of single nucleic Acid molecules. Biophys J. Jul. 2004;87(1):615-21. Erratum in: Biophys J. Nov. 2004;87(5):3618.
Nakane et al., Nanopore sensors for nucleic acid analysis. J. Phys.: Condens. Matter, vol. 15: R 1365-R1393 (2003).
Niemeyer et al., DNA-directed assembly of bienzymic complexes from in vivo biotinylated NAD(P)H:FMN oxidoreductase and luciferase. Chembiochem. Mar. 1, 2002;3(2-3):242-5.
Nikolov et al., Behavior of giant vesicles with anchored DNA molecules. Biophys J. Jun. 15, 2007;92(12):4356-68. Epub Mar. 23, 2007.
North et al., Host factors that promote transpososome disassembly and the PriA-PriC pathway for restart primosome assembly. Mol Microbiol. Jun. 2005;56(6):1601-16.
Nwe et al., Growing applications of "click chemistry" for bioconjugation in contemporary biomedical research. Cancer Biother Radiopharm. Jun. 2009;24(3):289-302. doi: 10.1089/cbr.2008.0626.
O'Shea et al., X-ray structure of the GCN4 leucine zipper, a two-stranded, parallel coiled coil. Science. Oct. 25, 1991;254(5031):539-44.
Paner et al., Studies of DNA dumbbells. III. Theoretical analysis of optical melting curves of dumbbells with a 16 base-pair duplex stem and Tn end loops (n=2, 3, 4, 6, 8, 10, 14). Biopolymers. Jul. 1992;32(7):881-92.
Paner et al., Studies of DNA dumbbells. VI. Analysis of optical melting curves of dumbbells with a sixteen-base pair duplex stem and end-loops of variable size and sequence. Biopolymers. Dec. 1996;39(6):779-93.
Pfeiffer et al., Bivalent cholesterol-based coupling of oligonucletides to lipid membrane assemblies. J Am Chem Soc. Aug. 25, 2004;126(33):10224-5.
Phoenix et al., OmpF-Lpp signal sequence mutants with varying charge hydrophobicity ratios provide evidence for a phosphatidylglycerol-signal sequence interaction during protein translocation across the *Escherichia coli* inner membrane. J Biol Chem. Aug. 15, 1993;268(23):17069-73.
Purnell et al., Nucleotide identification and orientation discrimination of DNA homopolymers immobilized in a protein nanopore. Nano Lett. Sep. 2008;8(9):3029-34. doi: 10.1021/nl802312f. Epub Aug. 13, 2008.
Remaut et al., Protein-protein interaction through beta-strand addition. Trends Biochem Sci. Aug. 2006;31(8):436-44. Epub Jul. 7, 2006.
Saariaho et al., Characteristics of MuA transposase-catalyzed processing of model transposon end DNA hairpin substrates. Nucleic Acids Res. Jun. 6, 2006;34(10):3139-49. Print 2006.
Sanchez-Quesada et al., Cyclic Peptides as Molecular Adapters for a Pore-Forming Protein. Journal American Chemical Society, vol. 122(48):11757-11766 (2000).
Sanchez-Quesada et al., Single DNA rotaxanes of a transmembrane pore protein. Angew Chem Int Ed Engl. Jun. 7, 2004;43(23):3063-7.
Sanderson, Personal genomes: Standard and pores. Nature. Nov. 6, 2008;456(7218):23-5. doi: 10.1038/456023a.
Satapathy et al., ATPase activity of RecD is essential for growth of the Antarctic Pseudomonas syringae Lz4W at low temperature. FEBS J. Apr. 2008;275(8):1835-51. doi: 10.1111/j.1742-4658.2008. 06342.x. Epub Mar. 9, 2008.

(56) References Cited

OTHER PUBLICATIONS

Sauer-Budge et al., Unzipping kinetics of double-stranded DNA in a nanopore. Phys Rev Lett. Jun. 13, 2003;90(23):238101. Epub Jun. 9, 2003.
Schneider et al., DNA sequencing with nanopores. Nat Biotechnol. Apr. 10, 2012;30(4):326-8. doi: 10.1038/nbt.2181.
Seeman, Nucleic acid junctions and lattices. J Theor Biol. Nov. 21, 1982;99(2):237-47.
Seo et al., Click chemistry to construct fluorescent oligonucleotides for DNA sequencing. J Org Chem. Jan. 24, 2003;68(2):609-12.
Seol et al., Stretching of homopolymeric RNA reveals single-stranded helices and base-stacking. Phys Rev Lett. Apr. 13, 2007;98(15):158103. Epub Apr. 12, 2007.
Shank et al., Redesigning channel-forming peptides: amino acid substitutions that enhance rates of supramolecular self-assembly and raise ion transport activity. Biophys J. Mar. 15, 2006;90(6):2138-50. Epub Dec. 30, 2005.
Shin et al., Kinetics of a reversible covalent-bond-forming reaction observed at the single-molecule level. Angew Chem Int Ed Engl. Oct. 4, 2002;41(19):3707-9; 3523.
Smeets et al., Salt dependence of ion transport and DNA translocation through solid-state nanopores. Nano Lett. Jan. 2006;6(1):89-95.
Smith et al., Capture, Unfolding, and Detection of Individual tRNA Molecules Using a Nanopore Device. Front Bioeng Biotechnol. Jun. 24, 2015;3:91. doi: 10.3389/fbioe.2015.00091.
Song et al., Structure of staphylococcal alpha-hemolysin, a heptameric transmembrane pore. Science. Dec. 13, 1996;274(5294):1859-66.
Soni et al., Synchronous optical and electrical detection of biomolecules traversing through solid-state nanopores. Rev Sci Instrum. Jan. 2010;81(1):014301. doi: 10.1063/1.3277116.
Stoddart et al., Multiple base-recognition sites in a biological nanopore: two heads are better than one. Angew Chem Int Ed Engl. 2010;49(3):556-9. doi: 10.1002/anie.200905483.
Stoddart et al., Single-nucleotide discrimination in immobilized DNA oligonucleotides with a biological nanopore. Proc Natl Acad Sci U S A. May 12, 2009;106(19):7702-7. doi: 10.1073/pnas.0901054106. Epub Apr. 20, 2009.
Sutherland et al., An analysis of mismatched duplex DNA unzipping through a bacterial nanopore. Biochem Cell Biol. Jun. 2004;82(3):407-12.
Tadey et al., Capillary electrophoretic separation of nucleotide isomers via complexation with cyclodextrin and borate. J Chromatogr B Biomed Appl. Jul. 15, 1994;657(2):365-72.
Thomas et al., Processivity of DNA exonucleases. J Biol Chem. Jan. 25, 1978;253(2):424-9.
Tohda et al., "Channel Mimetic Sensing Membranes for Nucleotides Based on Multitopic Hydrogen Bonding," Israel Journal of Chemistry, vol. 37:267-275 (1997).
Travers et al., A flexible and efficient template format for circular consensus sequencing and SNP detection. Nucleic Acids Res. Aug. 2010;38(15):e159. doi: 10.1093/nar/gkq543. Epub Jun. 22, 2010.
Troutt et al., Ligation-anchored PCR: a simple amplification technique with single-sided specificity. Proc Natl Acad Sci U S A. Oct. 15, 1992;89(20):9823-5. Erratum in: Proc Natl Acad Sci U S A Apr. 15, 1993;90(8):3775.
Tung et al., Preparation and applications of peptide-oligonucleotide conjugates. Bioconjug Chem. Sep.-Oct. 2000;11(5):605-18.
Tuteja et al., Unraveling DNA helicases. Motif, structure, mechanism and function. Eur J Biochem. May 2004;271(10):1849-63. Review. Erratum in: Eur J Biochem. Aug. 2004;271(15):3283.
United States District Court for the District of Delaware Order. *Pacific Biosciences of California, Inc. v. Oxford Nanopore Technolgoies, Inc.* Civil Action No. 17-275-RGA. Nov. 9, 2017.
Van De Goor, Nanopore Detection: Threading DNA Through a Tiny Hole. PharmaGenomics, vol. 4 (3):28-30 (2004).
Van Heel et al., Single-particle electron cryo-microscopy: towards atomic resolution. Q Rev Biophys. Nov. 2000;33(4):307-69.
Van Lengerich et al., Covalent attachment of lipid vesicles to a fluid-supported bilayer allows observation of DNA-mediated vesicle interactions. Langmuir. Jun. 1, 2010;26(11):8666-72. doi: 10.1021/la904822f.
Venkatesan et al., Nanopore sensors for nucleic acid analysis. Nat Nanotechnol. Sep. 18, 2011;6(10):615-24. doi: 10.1038/nnano.2011.129.
Walker et al., Key residues for membrane binding, oligomerization, and pore forming activity of staphylococcal alpha-hemolysin identified by cysteine scanning mutagenesis and targeted chemical modification. J Biol Chem. Sep. 29, 1995;270(39):23065-71.
Wang et al., Bioconjugation by copper(I)-catalyzed azide-alkyne [3+2] cycloaddition. J Am Chem Soc. Mar. 19, 2003;125(11):3192-3.
Wang et al., Nanopores with a spark for single-molecule detection. Nat Biotechnol. Jul. 2001;19(7):622-3.
Wanunu et al., Discrimination of methylcytosine from hydroxymethylcytosine in DNA molecules. J Am Chem Soc. Jan. 26, 2011;133(3):486-92. doi:10.1021/ja107836t. Epub Dec. 14, 2010.
Wanunu et al., DNA translocation governed by interactions with solid-state nanopores. Biophys J. Nov. 15, 2008;95(10):4716-25. doi: 10.1529/biophysj.108.140475. Epub Aug. 15, 2008.
Wemmer et al., Preparation and melting of single strand circular DNA loops. Nucleic Acids Res. Dec. 9, 1985;13(23):8611-21.
Winters-Hilt et al., Highly accurate classification of Watson-Crick basepairs on termini of single DNA molecules. Biophys J. Feb. 2003;84(2 Pt 1):967-76.
Wolfe et al., Catalyzing the translocation of polypeptides through attractive interactions. J Am Chem Soc. Nov. 14, 2007;129(45):14034-41. Epub Oct. 19, 2007.
Wong et al., Polymer capture by electro-osmotic flow of oppositely charged nanopores. J Chem Phys. Apr. 28, 2007;126(16):164903.
Woodman et al., Archaeal Hel308 domain V couples DNA binding to ATP hydrolysis and positions DNA for unwinding over the helicase ratchet. J Mol Biol. Dec. 14, 2007;374(5):1139-44. Epub Oct. 10, 2007.
Wu et al., Protein nanopores with covalently attached molecular adapters. J Am Chem Soc. Dec. 26, 2007;129(51):16142-8. Epub Nov. 30, 2007.
Xie et al., Single-molecule observation of the catalytic subunit of cAMP-dependent protein kinase binding to an inhibitor peptide. Chem Biol. Jan. 2005;12(1):109-20.
Yamagata et al., Overexpression, purification and characterization of RecJ protein from Thermus thermophilus HB8 and its core domain. Nucleic Acids Res. Nov. 15, 2001;29(22):4617-24.
Yoshina-Ishii et al., Arrays of mobile tethered vesicles on supported lipid bilayers. J Am Chem Soc. Apr. 2, 2003;125(13):3696-7.
Yusko et al., Controlling the translocation of proteins through nanopores with bioinspired fluid walls. Nat Nanotechnol. Apr. 2011; 6(4): 253-260. EPub Feb. 20, 2011. doi: 10.1038/nnano.2011.12.
[No Author Listed], Multiplex sequencing. https://www.illumina.com/science/technology/next-generation-sequencing/multiplex-sequencing.html. Printed on Nov. 4, 2021. 1 page.
[No Author Listed], Single-molecule real-time sequencing. Wikipedia entry/ Sep. 19, 2021. Retrieved from https://en.wikipedia.org/w/index.php?title+Singlemolecule_real-time_sequencing&oldid=1045146197. Printed on Nov. 4, 2021. 10 pages.
Dong et al., Amplified detection of nucleic acid by G-quadruplex based hybridization chain reaction. Biosens Bioelectron. Oct.-Dec. 2012;38(1):258-63. doi: 10.1016/j.bios.2012.05.042. Epub Jun. 8, 2012.
Faller et al., The structure of a mycobacterial outer-membrane channel. Science. Feb. 20, 2004;303(5661):1189-92. doi: 10.1126/science.1094114.
He et al., The carboxyl-terminal domain of bacteriophage T7 single-stranded DNA-binding protein modulates DNA binding and interaction with T7 DNA polymerase. J Biol Chem. Aug. 8, 2003;278(32):29538-45. doi: 10.1074/jbc.M304318200. Epub May 24, 2003.

(56) References Cited

OTHER PUBLICATIONS

Hollis et al., Structure of the gene 2.5 protein, a single-stranded DNA binding protein encoded by bacteriophage T7. Proc Natl Acad Sci U S A. Aug. 14, 2001;98(17):9557-62. doi: 10.1073/pnas.171317698. Epub Jul. 31, 2001.

Hyland et al., The DNA binding domain of the gene 2.5 single-stranded DNA-binding protein of bacteriophage T7. J Biol Chem. Feb. 28, 2003;278(9):7247-56. doi: 10.1074/jbc.M210605200. Epub Dec. 20, 2002.

Kahvejian et al., Making single-molecule sequencing a reality. American Laboratory. Jan. 1, 2008;40(20):48-53. www.americanlaboratory.com/913-Technical-Articles/780-Making-Single-Molecule-Sequencing-a-Reality/. Last accessed Dec. 10, 2021.

Kuipers, Random mutagenesis by using mixtures of dNTP and dITP in PCR. Methods Mol Biol. 1996;57:351-6. doi: 10.1385/0-89603-332-5:351.

Liang, Structure of outer membrane protein G by solution NMR spectroscopy. Proc Natl Acad Sci U S A. Oct. 9, 2007;104(41):16140-5. doi: 10.1073/pnas.0705466104. Epub Oct. 2, 2007.

Locher et al., Transmembrane signaling across the ligand-gated FhuA receptor: crystal structures of free and ferrichrome-bound states reveal allosteric changes. Cell. Dec. 11, 1998;95(6):771-8. doi: 10.1016/s0092-8674(00)81700-6.

Pettersson et al., Generations of sequencing technologies. Genomics. Feb. 2009;93(2):105-11. doi: 10.1016/j.ygeno.2008.10.003. Epub Nov. 21, 2008.

Rezende et al., Essential amino acid residues in the single-stranded DNA-binding protein of bacteriophage T7. Identification of the dimer interface. J Biol Chem. Dec. 27, 2002;277(52):50643-53. doi: 10.1074/jbc.M207359200. Epub Oct. 12, 2002.

Shendure et al., Overview of DNA sequencing strategies. Curr Protoc Mol Biol. Jan. 2008;Chapter 7:Unit 7.1. doi: 10.1002/0471142727.mb0701s81.

Spee et al., Efficient random mutagenesis method with adjustable mutation frequency by use of PCR and dITP. Nucleic Acids Res. Feb. 11, 1993;21(3):777-8. doi: 10.1093/nar/21.3.777.

Wang et al., A simple and reproducible method for directed evolution: combination of random mutation with dITP and DNA fragmentation with endonuclease V. Mol Biotechnol. Jan. 2013;53(1):49-54. doi: 10.1007/s12033-012-9516-9.

Yamashita et al., Crystal structures of the OmpF porin: function in a colicin translocon. EMBO J. Aug. 6, 2008;27(15):2171-80. doi: 10.1038/emboj.2008.137. Epub Jul. 17, 2008.

U.S. Appl. No. 17/821,950, filed Aug. 24, 2022, McKeown.

U.S. Appl. No. 17/843,888, filed Jun. 17, 2022, White et al.

Manosas et al., Magnetic tweezers for the study of DNA tracking motors. Methods Enzymol. 2010;475:297-320. doi: 10.1016/S0076-6879(10)75013-8.

Matson et al., The gene 4 protein of bacteriophage T7. Characterization of helicase activity. J Biol Chem. Nov. 25, 1983;258(22):14017-24.

* cited by examiner

Distribution of Per-read Accuracies

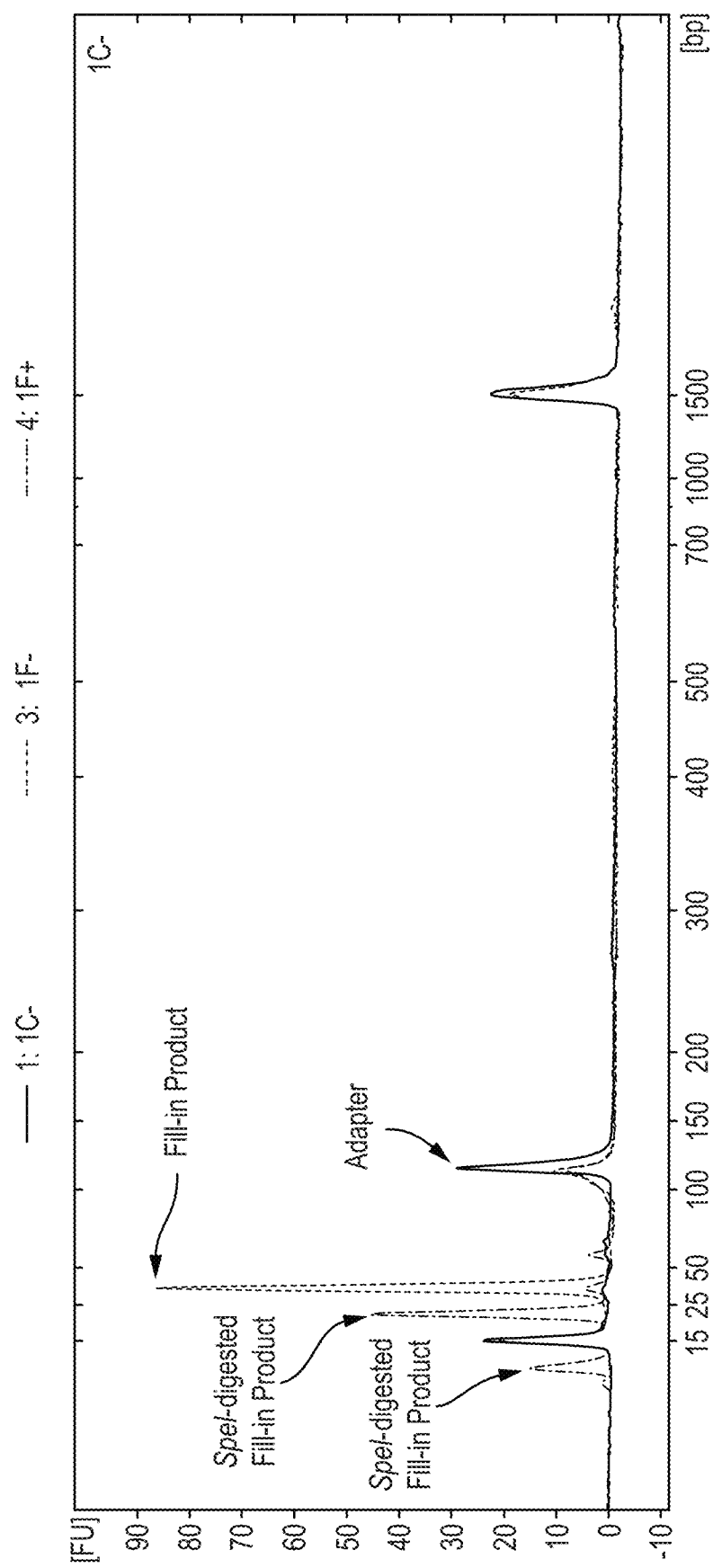

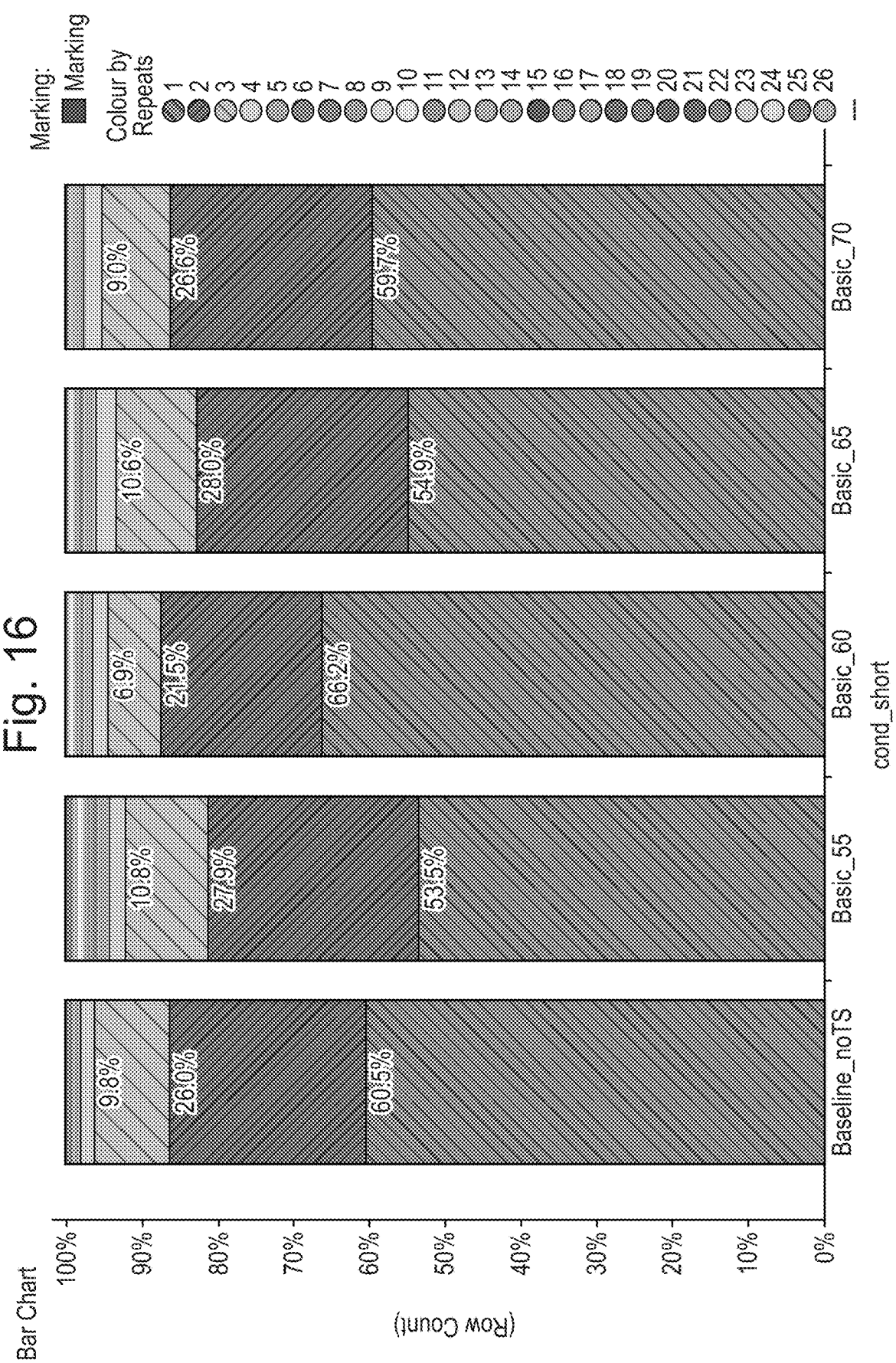

SEQUENCE LISTING

<160> NUMBER OF SEQ ID NOS: 11

<210> SEQ ID NO 1
<211> LENGTH: 47
<212> TYPE: DNA
<213> ORGANISM: Artificial Sequence
<220> FEATURE:
<223> OTHER INFORMATION: Synthetic polynucleotide

<400> SEQUENCE: 1
gcgtactttt tagtacgctt ttcggcgtct gcttgggtgt ttaacct        47

<210> SEQ ID NO 2
<211> LENGTH: 47
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: deoxyinosine
<220> FEATURE:
<221> NAME/KEY: misc_feature
<222> LOCATION: (2)..(2)
<223> OTHER INFORMATION: deoxyzebularine
<220> FEATURE:
<221> NAME/KEY: misc_feature
<222> LOCATION: (3)..(3)
<223> OTHER INFORMATION: deoxyinosine
<220> FEATURE:
<221> NAME/KEY: misc_feature
<222> LOCATION: (6)..(6)
<223> OTHER INFORMATION: deoxyzebularine
<220> FEATURE:
<221> NAME/KEY: misc_feature
<222> LOCATION: (13)..(13)
<223> OTHER INFORMATION: deoxyinosine
<220> FEATURE:
<221> NAME/KEY: misc_feature
<222> LOCATION: (16)..(16)
<223> OTHER INFORMATION: deoxyzebularine
<220> FEATURE:
<221> NAME/KEY: misc_feature
<222> LOCATION: (17)..(17)
<223> OTHER INFORMATION: deoxyinosine
<220> FEATURE:
<221> NAME/KEY: misc_feature
<222> LOCATION: (18)..(18)
<223> OTHER INFORMATION: deoxyzebularine

<400> SEQUENCE: 2
nnntantttt tantannntt ttcggcgtct gcttgggtgt ttaacct        47

<210> SEQ ID NO 3
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 3

```
ggttaaacac ccaagcagac gccg                                              24
```

<210> SEQ ID NO 4
<211> LENGTH: 22
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: deoxyinosine
<220> FEATURE:
<221> NAME/KEY: misc_feature
<222> LOCATION: (2)..(2)
<223> OTHER INFORMATION: deoxyzebularine
<220> FEATURE:
<221> NAME/KEY: misc_feature
<222> LOCATION: (3)..(3)
<223> OTHER INFORMATION: deoxyinosine
<220> FEATURE:
<221> NAME/KEY: misc_feature
<222> LOCATION: (6)..(6)
<223> OTHER INFORMATION: deoxyzebularine
<220> FEATURE:
<221> NAME/KEY: misc_feature
<222> LOCATION: (13)..(13)
<223> OTHER INFORMATION: deoxyinosine
<220> FEATURE:
<221> NAME/KEY: misc_feature
<222> LOCATION: (16)..(16)
<223> OTHER INFORMATION: deoxyzebularine
<220> FEATURE:
<221> NAME/KEY: misc_feature
<222> LOCATION: (17)..(17)
<223> OTHER INFORMATION: deoxyinosine
<220> FEATURE:
<221> NAME/KEY: misc_feature
<222> LOCATION: (18)..(18)
<223> OTHER INFORMATION: deoxyzebularine

<400> SEQUENCE: 4

```
nnntantttt tantannntt tt                                                22
```

<210> SEQ ID NO 5
<211> LENGTH: 70
<212> TYPE: DNA
<213> ORGANISM: Artificial Sequence
<220> FEATURE:
<223> OTHER INFORMATION: Synthetic polynucleotide
<220> FEATURE:
<221> NAME/KEY: modified_base
<222> LOCATION: (1)..(1)
<223> OTHER INFORMATION: 5' DBCO-TEG
<220> FEATURE:
<221> NAME/KEY: misc_feature
<222> LOCATION: (17)..(20)
<223> OTHER INFORMATION: C3 Spacer
<220> FEATURE:
<221> NAME/KEY: misc_feature
<222> LOCATION: (21)..(21)
<223> OTHER INFORMATION: deoxyinosine
<220> FEATURE:
<221> NAME/KEY: misc_feature
<222> LOCATION: (22)..(22)
<223> OTHER INFORMATION: deoxyzebularine
<220> FEATURE:
<221> NAME/KEY: misc_feature
<222> LOCATION: (23)..(23)
<223> OTHER INFORMATION: deoxyinosine
<220> FEATURE:
<221> NAME/KEY: misc_feature
<222> LOCATION: (26)..(26)
<223> OTHER INFORMATION: deoxyzebularine
<220> FEATURE:
<221> NAME/KEY: misc_feature

```
<222> LOCATION: (33)..(33)
<223> OTHER INFORMATION: deoxyinosine
<220> FEATURE:
<221> NAME/KEY: misc_feature
<222> LOCATION: (36)..(36)
<223> OTHER INFORMATION: deoxyzebularine
<220> FEATURE:
<221> NAME/KEY: misc_feature
<222> LOCATION: (37)..(37)
<223> OTHER INFORMATION: deoxyinosine
<220> FEATURE:
<221> NAME/KEY: misc_feature
<222> LOCATION: (38)..(38)
<223> OTHER INFORMATION: deoxyzebularine

<400> SEQUENCE: 5
gcttgggtgt ttaaccnnnn nnntantttt tantannntt ttgcttacgg ttcactactc      60
acgacgatgt                                                            70

<210> SEQ ID NO 6
<211> LENGTH: 70
<212> TYPE: DNA
<213> ORGANISM: Artificial Sequence
<220> FEATURE:
<223> OTHER INFORMATION: Synthetic polynucleotide
<220> FEATURE:
<221> NAME/KEY: modified_base
<222> LOCATION: (1)..(1)
<223> OTHER INFORMATION: 5' DBCO-TEG
<220> FEATURE:
<221> NAME/KEY: misc_feature
<222> LOCATION: (17)..(20)
<223> OTHER INFORMATION: C3 Spacer
<220> FEATURE:
<221> NAME/KEY: misc_feature
<222> LOCATION: (21)..(21)
<223> OTHER INFORMATION: deoxyinosine
<220> FEATURE:
<221> NAME/KEY: misc_feature
<222> LOCATION: (22)..(22)
<223> OTHER INFORMATION: deoxyzebularine
<220> FEATURE:
<221> NAME/KEY: misc_feature
<222> LOCATION: (23)..(23)
<223> OTHER INFORMATION: deoxyinosine
<220> FEATURE:
<221> NAME/KEY: misc_feature
<222> LOCATION: (26)..(26)
<223> OTHER INFORMATION: deoxyzebularine
<220> FEATURE:
<221> NAME/KEY: misc_feature
<222> LOCATION: (33)..(33)
<223> OTHER INFORMATION: deoxyinosine
<220> FEATURE:
<221> NAME/KEY: misc_feature
<222> LOCATION: (36)..(36)
<223> OTHER INFORMATION: deoxyzebularine
<220> FEATURE:
<221> NAME/KEY: misc_feature
<222> LOCATION: (37)..(37)
<223> OTHER INFORMATION: deoxyinosine
<220> FEATURE:
<221> NAME/KEY: misc_feature
<222> LOCATION: (38)..(38)
<223> OTHER INFORMATION: deoxyzebularine

<400> SEQUENCE: 6
gcttgggtgt ttaaccnnnn nnntanaaaa atntannnaa aagcttacgg ttcactactc      60
acgacgatgt                                                            70

<210> SEQ ID NO 7
<211> LENGTH: 80
<212> TYPE: DNA
```

```
<213> ORGANISM: Artificial Sequence
<220> FEATURE:
<223> OTHER INFORMATION: Synthetic polynucleotide
<220> FEATURE:
<221> NAME/KEY: modified_base
<222> LOCATION: (1)..(1)
<223> OTHER INFORMATION: 5' DBCO-TEG
<220> FEATURE:
<221> NAME/KEY: misc_feature
<222> LOCATION: (17)..(20)
<223> OTHER INFORMATION: C3 Spacer
<220> FEATURE:
<221> NAME/KEY: misc_feature
<222> LOCATION: (21)..(21)
<223> OTHER INFORMATION: deoxyinosine
<220> FEATURE:
<221> NAME/KEY: misc_feature
<222> LOCATION: (22)..(22)
<223> OTHER INFORMATION: deoxyzebularine
<220> FEATURE:
<221> NAME/KEY: misc_feature
<222> LOCATION: (23)..(23)
<223> OTHER INFORMATION: deoxyinosine
<220> FEATURE:
<221> NAME/KEY: misc_feature
<222> LOCATION: (25)..(25)
<223> OTHER INFORMATION: deoxyzebularine
<220> FEATURE:
<221> NAME/KEY: misc_feature
<222> LOCATION: (26)..(27)
<223> OTHER INFORMATION: deoxyinosine
<220> FEATURE:
<221> NAME/KEY: misc_feature
<222> LOCATION: (31)..(31)
<223> OTHER INFORMATION: deoxyinosine
<220> FEATURE:
<221> NAME/KEY: misc_feature
<222> LOCATION: (38)..(38)
<223> OTHER INFORMATION: deoxyzebularine
<220> FEATURE:
<221> NAME/KEY: misc_feature
<222> LOCATION: (42)..(43)
<223> OTHER INFORMATION: deoxyzebularine
<220> FEATURE:
<221> NAME/KEY: misc_feature
<222> LOCATION: (44)..(44)
<223> OTHER INFORMATION: deoxyinosine
<220> FEATURE:
<221> NAME/KEY: misc_feature
<222> LOCATION: (46)..(46)
<223> OTHER INFORMATION: deoxyzebularine
<220> FEATURE:
<221> NAME/KEY: misc_feature
<222> LOCATION: (47)..(47)
<223> OTHER INFORMATION: deoxyinosine
<220> FEATURE:
<221> NAME/KEY: misc_feature
<222> LOCATION: (48)..(48)
<223> OTHER INFORMATION: deoxyzebularine

<400> SEQUENCE: 7
gcttgggtgt ttaaccnnnn nnnannntat naaaaatnat annntnnnaa aagcttacgg     60
ttcactactc acgacgatgt                                                80

<210> SEQ ID NO 8
<211> LENGTH: 80
<212> TYPE: DNA
<213> ORGANISM: Artificial Sequence
<220> FEATURE:
<223> OTHER INFORMATION: Synthetic polynucleotide
<220> FEATURE:
<221> NAME/KEY: modified_base
<222> LOCATION: (1)..(1)
<223> OTHER INFORMATION: 5' DBCO-TEG
<220> FEATURE:
<221> NAME/KEY: misc_feature
```

```
<222> LOCATION: (17)..(20)
<223> OTHER INFORMATION: C3 Spacer
<220> FEATURE:
<221> NAME/KEY: misc_feature
<222> LOCATION: (21)..(21)
<223> OTHER INFORMATION: deoxyzebularine
<220> FEATURE:
<221> NAME/KEY: misc_feature
<222> LOCATION: (23)..(23)
<223> OTHER INFORMATION: deoxyinosine
<220> FEATURE:
<221> NAME/KEY: misc_feature
<222> LOCATION: (26)..(26)
<223> OTHER INFORMATION: deoxyzebularine
<220> FEATURE:
<221> NAME/KEY: misc_feature
<222> LOCATION: (27)..(27)
<223> OTHER INFORMATION: deoxyinosine
<220> FEATURE:
<221> NAME/KEY: misc_feature
<222> LOCATION: (30)..(31)
<223> OTHER INFORMATION: deoxyinosine
<220> FEATURE:
<221> NAME/KEY: misc_feature
<222> LOCATION: (38)..(39)
<223> OTHER INFORMATION: deoxyzebularine
<220> FEATURE:
<221> NAME/KEY: misc_feature
<222> LOCATION: (42)..(42)
<223> OTHER INFORMATION: deoxyzebularine
<220> FEATURE:
<221> NAME/KEY: misc_feature
<222> LOCATION: (43)..(43)
<223> OTHER INFORMATION: deoxyinosine
<220> FEATURE:
<221> NAME/KEY: misc_feature
<222> LOCATION: (46)..(46)
<223> OTHER INFORMATION: deoxyzebularine
<220> FEATURE:
<221> NAME/KEY: misc_feature
<222> LOCATION: (48)..(48)
<223> OTHER INFORMATION: deoxyinosine

<400> SEQUENCE: 8
gcttgggtgt ttaaccnnnn nantanntan naaaaatnnt anntantnaa aagcttacgg      60
ttcactactc acgacgatgt                                                 80

<210> SEQ ID NO 9
<211> LENGTH: 27
<212> TYPE: DNA
<213> ORGANISM: Artificial Sequence
<220> FEATURE:
<223> OTHER INFORMATION: Synthetic polynucleotide

<400> SEQUENCE: 9
catcgtcgtg actagtgaac cgtaagc                                         27

<210> SEQ ID NO 10
<211> LENGTH: 27
<212> TYPE: DNA
<213> ORGANISM: Artificial Sequence
<220> FEATURE:
<223> OTHER INFORMATION: Synthetic polynucleotide

<400> SEQUENCE: 10
catcgtcgtg agtagtgaac cgtaagc                                         27

<210> SEQ ID NO 11
<211> LENGTH: 49
<212> TYPE: DNA
<213> ORGANISM: Artificial Sequence
<220> FEATURE:
```

```
<223> OTHER INFORMATION: Synthetic polynucleotide
<220> FEATURE:
<221> NAME/KEY: misc_feature
<222> LOCATION: (1)..(1)
<223> OTHER INFORMATION: deoxyinosine
<220> FEATURE:
<221> NAME/KEY: misc_feature
<222> LOCATION: (2)..(2)
<223> OTHER INFORMATION: deoxyzebularine
<220> FEATURE:
<221> NAME/KEY: misc_feature
<222> LOCATION: (3)..(3)
<223> OTHER INFORMATION: deoxyinosine
<220> FEATURE:
<221> NAME/KEY: misc_feature
<222> LOCATION: (6)..(6)
<223> OTHER INFORMATION: deoxyzebularine
<220> FEATURE:
<221> NAME/KEY: misc_feature
<222> LOCATION: (13)..(13)
<223> OTHER INFORMATION: deoxyinosine
<220> FEATURE:
<221> NAME/KEY: misc_feature
<222> LOCATION: (16)..(16)
<223> OTHER INFORMATION: deoxyzebularine
<220> FEATURE:
<221> NAME/KEY: misc_feature
<222> LOCATION: (17)..(17)
<223> OTHER INFORMATION: deoxyinosine
<220> FEATURE:
<221> NAME/KEY: misc_feature
<222> LOCATION: (18)..(18)
<223> OTHER INFORMATION: deoxyzebularine

<400> SEQUENCE: 11
nnntantttt tantannntt tgcttacggt tcactactca cgacgatgt          49
```

METHODS AND POLYNUCLEOTIDES FOR AMPLIFYING A TARGET POLYNUCLEOTIDE

RELATED APPLICATIONS

Foreign priority benefits are claimed under 35 U.S.C. § 119 of British application number 1807793.3, filed May 14, 2018. The entire contents of which is hereby incorporated by reference in its entirety.

FIELD

The invention relates generally to methods of amplifying polynucleotides. The invention also relates generally to methods of characterising the amplified polynucleotides, and to regents and kits for amplifying polynucleotides.

BACKGROUND

Rolling Circle Amplification (RCA), an isothermal DNA amplification technique, has been developed based on the natural rolling circle replication process of bacteriophages. RCA is a process of unidirectional nucleic acid replication that can be used to rapidly synthesise multiple copies of circular polynucleotide molecules. RCA is widely used in molecular biology, particularly to amplify signals in biological detection methods.

There are three main ways to make a RCA template. In a first method, a single strand DNA ligase may be used to circularise the template DNA before a random or designed primer is annealed. A polymerase is used to amplify the DNA and it displaces the primer and the extended product as it proceeds around the circular template. Disadvantages of this method are that it is difficult to circularise the DNA, it is only possible to obtain information on the template strand and the template is never included in the product, only copies.

In a second method, an oligonucleotide splint of known sequence, complementary to the two ends of the single strand DNA, is annealed to the single strand DNA and the gap between the two ends of the single strand DNA is sealed with a double stranded DNA ligase to circularise the template. Polymerase amplification begins with the splint acting as a primer, and displaces the primer and extended product as it goes. Disadvantages of this method are that knowledge of the single strand sequence is required to circularise the DNA, it is only possible to obtain information on the template strand and the template is never included in the product, only copies.

In a third method, a DNA hairpin is ligated to both strands of double stranded DNA. A primer complementary to the DNA hairpin is annealed and a polymerase is used to amplify both strands of the DNA. As amplification proceeds the polymerase displaces the primer and extended product. A disadvantage of this method is that the template is never included in the product, only copies.

Loop mediated isothermal amplification (LAMP) is a single tube technique for the amplification of DNA that is carried out at a constant temperature using two or three primer pairs and a polymerase.

SUMMARY

The inventors have devised a method of rolling linear amplification. The method uses a polymerase to copy a 5' hairpin at the end of a polynucleotide strand, which hairpin comprises at least one non-canonical base, to create a complementary sequence with the potential to form a 3' hairpin. As the 5' hairpin contains at least one modified nucleotide and the complementary sequence is synthesised using canonical nucleotides, it is more energetically favourable for the ends of the extended polynucleotide to form a 3' hairpin and a 5' hairpin, than for the 3' and 5' ends of the extended polynucleotide to hybridise to one another. Therefore, in the extended polynucleotide, the original 5' hairpin and a new 3' hairpin form rapidly after synthesis of the extension complementary to the original polynucleotide strand. The newly formed 3' hairpin provides a site from which a polymerase can initiate to copy the extended polynucleotide so that the whole cycle can be repeated. This cycle can be repeated multiple times.

The new method has the advantage that it can be performed without any knowledge of the target sequence, or can be made target specific. For example, an adaptor comprising the 5' hairpin may be attached to the 5' end of a single stranded target polynucleotide, or to the 5' end of one or both strands of a double stranded polynucleotide. The 5' hairpin may, for example, be attached by ligation, topoligation, click chemistry or by use of a transposase. An adaptor comprising a 3' hairpin may be attached to the 3' end of a template polynucleotide, or to the 3' end of one or both strands of a double stranded polynucleotide. The adaptor may comprise both the 5' hairpin and the 3' hairpin. Alternatively, the 5' hairpin may be included in PCR primers that can be used to amplify a polynucleotide sequence between two known sequences.

The new method has the advantage that the original target sequence can be included in the amplified product, which is an extension of the template polynucleotide. This is particularly useful for producing a product for use in detecting modifications to a polynucleotide, such as, for example, DNA methylation.

Accordingly, provided herein is a method of amplifying a target polynucleotide comprising:
 (a) providing a template polynucleotide comprising a 5' hairpin, a target polynucleotide and a 3' hairpin, wherein the 5' hairpin comprises one or more non-canonical nucleotides;
 (b) contacting the template polynucleotide with a polymerase and canonical nucleotides, wherein:
  (i) the polymerase extends, using the canonical nucleotides, the template polynucleotide from its 3' end to form a first extended polynucleotide comprising the 5' hairpin at its 5' end and the complement of the 5' hairpin at its 3' end, wherein the complement of the 5' hairpin forms a 3' hairpin; and
  (ii) the polymerase extends the first extended polynucleotide from its 3' end to form a second extended polynucleotide comprising the 5' hairpin at its 5' end and the complement of the 5' hairpin at its 3' end, wherein the complement of the 5' hairpin forms a 3' hairpin.

The following methods that utilise this principle are also provided:
 a method of amplifying a target polynucleotide, comprising:
  (a) providing a primer pair, wherein each primer comprises a 5' hairpin that comprises one or more non-canonical nucleotides;
  (b) contacting a sample comprising a target polynucleotide with the primer pair, a polymerase and canonical nucleotides under conditions suitable for polymerase activity; and a method of amplifying a target polynucleotide, comprising:

(a) ligating an adaptor comprising a 5' hairpin that comprises one or more non-canonical nucleotides to the target polynucleotide to produce a template polynucleotide;

(b) contacting the template polynucleotide with a polymerase and canonical nucleotides under conditions suitable for polymerase activity.

Also provided are:

an extended polynucleotide obtainable by the above methods;

a method of characterising a polynucleotide, comprising:

(a) contacting the extended polynucleotide obtainable by the above method with a nanopore such the polynucleotide translocates through the nanopore; and (b) taking one or more measurements as the polynucleotide moves with respect to the nanopore, wherein the measurements are indicative of one or more characteristics of the polynucleotide and thereby characterising the polynucleotide;

a double stranded polynucleotide adaptor comprising a first strand and a second strand, wherein the first strand comprises a 5' hairpin comprising one or more non-canonical nucleotides, and the second strand comprises a 3' hairpin;

a PCR primer pair, wherein each primer comprises a 5' hairpin that comprises one or more non-canonical nucleotides; and a kit for amplifying a target polynucleotide comprising: an adaptor comprising a first strand and a second strand, wherein the first strand comprises a 5' hairpin comprising one or more non-canonical nucleotides, and the second strand comprises a 3' hairpin or a a PCR primer pair, wherein each primer comprises a 5' hairpin that comprises one or more non-canonical nucleotides; and a polymerase.

DESCRIPTION OF THE FIGURES

It is to be understood that Figures are for the illustration purposes and are not intended to be limiting.

FIGS. 1A-1C show the three main ways to make a rolling circle amplification template. FIG. 1A: A single strand DNA ligase is used to circularise the template DNA before a random or designed primer is annealed. Polymerase amplification begins and displaces the primer and extended product as it goes. FIG. 1B: An oligo splint of known sequence, complementary to the two ends of the single strand DNA, is annealed and the gap sealed with a double stranded DNA ligase to circularise the template. Polymerase amplification begins with the splint acting as a primer and displaces the primer and extended product as it goes. FIG. 1C: A DNA hairpin is ligated to both strands of double stranded DNA. A primer complementary to the DNA hairpin is annealed and polymerase amplification begins. As amplification proceeds it and displaces the primer and extended product as it goes.

FIG. 3A: ligation of a double stranded adaptor comprising a 5' hairpin (3) made up only of canonical nucleotides to a double stranded template polynucleotide (1), followed by addition of a polymerase (4) and canonical nucleotides (dA, dT, dG, dC) results in a double stranded polynucleotide in which the two strands hybridise along the whole length of the polynucleotide. The polymerase synthesizes the complement of the 5' hairpin and it is more energetically favourable for the two strands to hybridise to one another than to form terminal hairpins. FIG. 3B: ligation of an adaptor comprising a 5' hairpin (2) made up of both canonical and non-canonical nucleotides (e.g. dITAZ, wherein dI is deoxyinosine and dZ is deoxyzebularine) to a double stranded template polynucleotide (1), followed by addition of a polymerase and canonical nucleotides results in a double stranded polynucleotide in which only the central portions of the two strands hybridise to each other whilst the 5' and 3' ends form hairpins. This occurs because folding of the dGTAC complement of the dITAZ sequence to form a hairpin that includes G-C base pairs is more favourable than the dGTAC complement of the dITAZ sequence remaining base paired with the dITAZ nucleotides in the top strand. The non-canonical nucleotides, I and Z, each form two hydrogen bonds per base pair when base paired with the canonical nucleotides G and C in the bottom strand. Thus, separation of the top and bottom strands and formation of the hairpins is more energetically favourable, as it allows the canonical nucleotides G and C in the bottom strand to form G-C base pairs, each G-C base pair having three hydrogen bonds, in contrast to the two hydrogen bonds per base pair formed with the non-canonical nucleotides. The polymerase then fills-in from the newly formed 3' hairpin and the process repeats to produce multiple copies of linked template and complement as described in the FIG. 2 legend.

FIG. 4A shows the trace when the 124 bp polynucleotide alone was analysed. The peaks marked 15 and 1500 are markers, and the peak marked 119 is the 124 bp polynucleotide. FIG. 4B shows the trace after ligation of the adaptor comprising a 5' dGTAC hairpin to the 124 bp polynucleotide, overlaid on the trace from FIG. 4A. During the ligation reaction the adaptor is added to both ends of some molecules of the 124 bp polynucleotide (represented by the peak marked 2×) and to just one end of other molecules of the 124 bp polynucleotide (the peak marked 1×). FIG. 4C shows the trace after ligation of the adaptor comprising a 5' dITAZ hairpin to the 124 bp polynucleotide, overlaid on the trace from FIG. 4A. During the ligation reaction the adaptor is added to both ends of some molecules of the 124 bp polynucleotide (represented by the peak marked 2×) and to just one end of other molecules of the 124 bp polynucleotide (the peak marked 1×).

FIG. 5A shows the products obtained using the dGTAC 5' hairpin with the trace obtained for the products of the ligation reaction prior to addition of the polymerase and SSB overlaid. The ligation products (marked 1× and 2× in FIGS. 4A-4C) are shifted to a peak that corresponds to a double stranded 124 bp polynucleotide in which the 3' ends of the strands opposite the 5' hairpin have been filled in by the polymerase. FIG. 5B shows the products obtained using the dITAZ 5' hairpin with the trace obtained for the products of the ligation reaction prior to addition of the polymerase and SSB overlaid. Some of the ligation products (marked 1× and 2× in FIGS. 4A-4C) are shifted to a small peak that corresponds to a double stranded 124 bp polynucleotide in which the 3' ends of the strands opposite the 5' hairpin have been filled in by the polymerase. There is also a large peak that corresponds to a high molecular weight repeating polynucleotide structure. FIG. 5C is an overlay of the reaction products obtained using the dGTAC 5' hairpin and the reaction products obtained using the dITAZ 5' hairpin.

FIG. 6A shows that short reads were obtained when the dGTAC 5' hairpin adaptor was used and FIG. 6B shows that a population of reads with increased read lengths was obtained when the dITAZ 5' hairpin adaptor was used.

FIG. 15 shows the digestion of the fill in product by SpeI, confirming that the SpeI restruction site was formed in the amplification product generated by the action of the Bst 3.0 polymerase. The traces for RLA_Top and RLA_btm_v2_SpeI, adapter, fill-in product and SpeI digested fill-in product are overlaid.

FIG. 16 compares the amplification products generated at different incubation temperatures. The baseline_noTS was carried out at 50° C. The other temperatures used were 55° C., 60° C., 65° C. and 70° C. as indicated in the figure. The products were sequenced using an Oxford Nanopore Technologies' flow cell and analysed for the presence of repeats of the template and complement sections. The number of repeats is shown in the bargraph in FIG. 16.

DESCRIPTION OF THE SEQUENCE LISTING

Figure 1C:
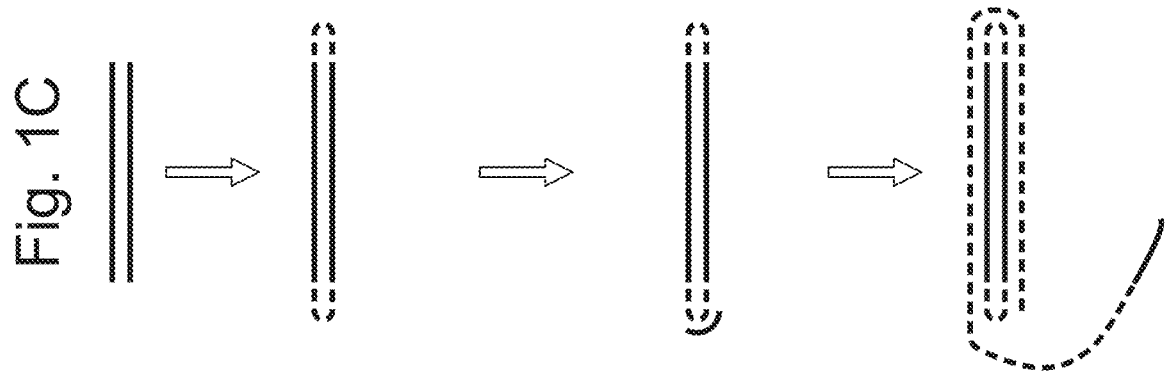
FIGS. 1A-1C illustrate the principle of rolling circle amplification as known in the prior art.
Figure 1B:
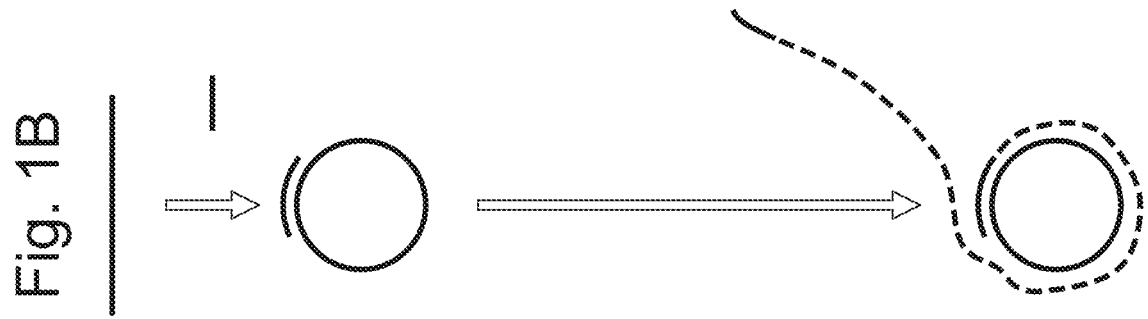
Figure 1A:
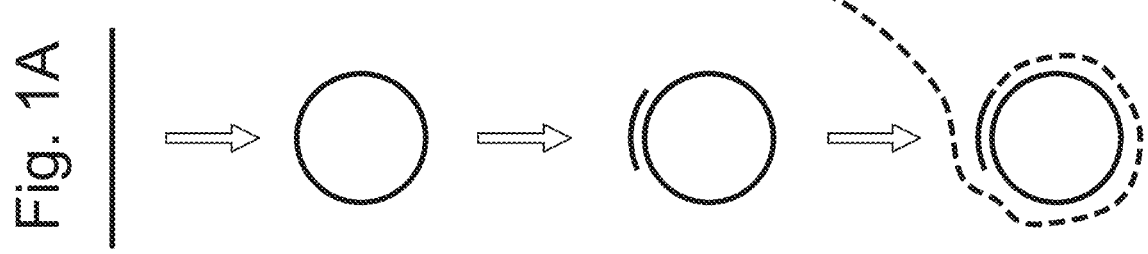
Figure 2:
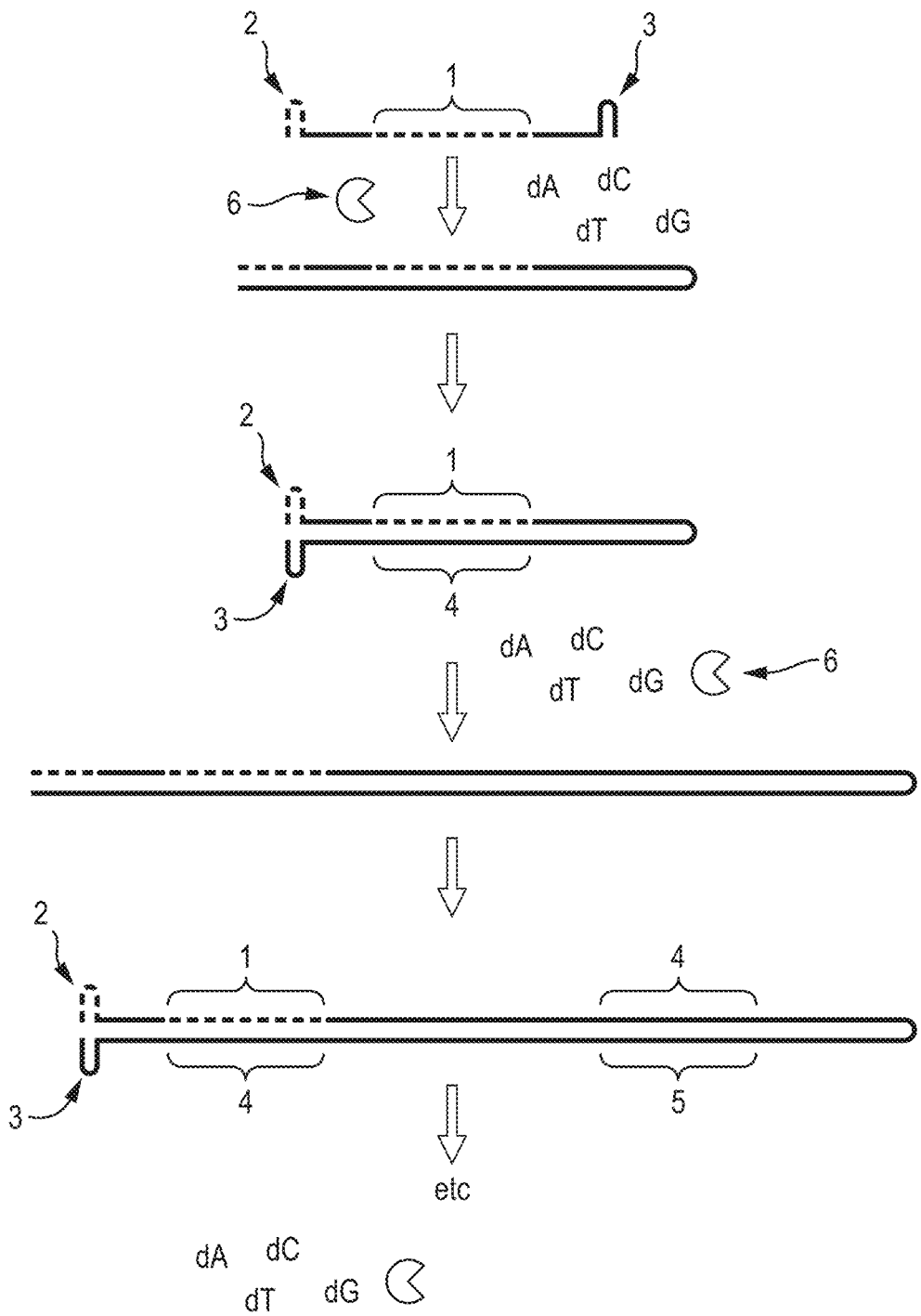
FIG. 2 illustrates the principle of rolling linear amplification. The starting template polynucleotide comprises a target polynucleotide (1), a 5' hairpin (2) and a 3' hairpin (3). The 5' hairpin (2) comprises at least one non-canonical nucleotide. The 3' hairpin facilitates the binding of a polymerase (6) to the 3' end of the template polynucleotide. The polymerase then extends the 3' end of the template polynucleotide by synthesizing the complement of the template using only canonical nucleotides (dA, dT, dG, dC), including the target polynucleotide and the 5' hairpin. It is more energetically favourable for the 5' hairpin to reform and for the complement of the 5' hairpin to form a new 3' hairpin than for the 5' hairpin to hybridise to its complement. Therefore the extension product forms a new template that comprises the target polynucleotide (1), the 5' hairpin (2), a 3' hairpin (3) and the complement of the target polynucleotide (4). The 3' hairpin facilitates the binding of a polymerase (6) to the 3' end of the template polynucleotide. The polymerase then extends the 3' end of the template polynucleotide by synthesizing the complement of the template using only canonical nucleotides (dA, dT, dG, dC), including the target polynucleotide and the 5' hairpin. It is more energetically favourable for the 5' hairpin to reform and for the complement of the 5' hairpin to form a new 3' hairpin than for the 5' hairpin to hybridise to its complement. Therefore, the second extension product forms a new template that comprises the target polynucleotide (1), the 5' hairpin (2), a 3' hairpin (3), two complements of the target polynucleotide (4) and a copy of the target polynucleotide. The extension cycle can be repeated to produce increasingly longer templates that comprise the template polynucleotide and multiple copies of the template polynucleotide and its complement.
Figure 3A:
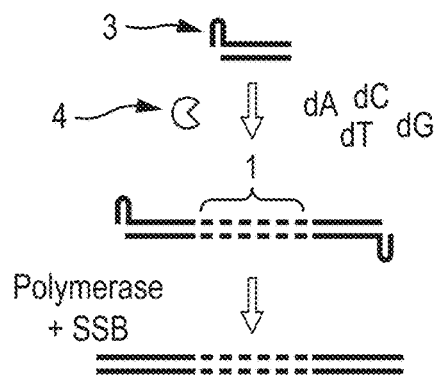
FIGS. 3A-3B further illustrate the principle of rolling linear amplification using adaptors comprising a 5' hairpin. The amplification cycles shown in FIG. 2 are depicted in the bottom right of FIGS. 3A-3B, but using a double stranded template instead of a single stranded template as in FIG. 2.
Figure 3B:
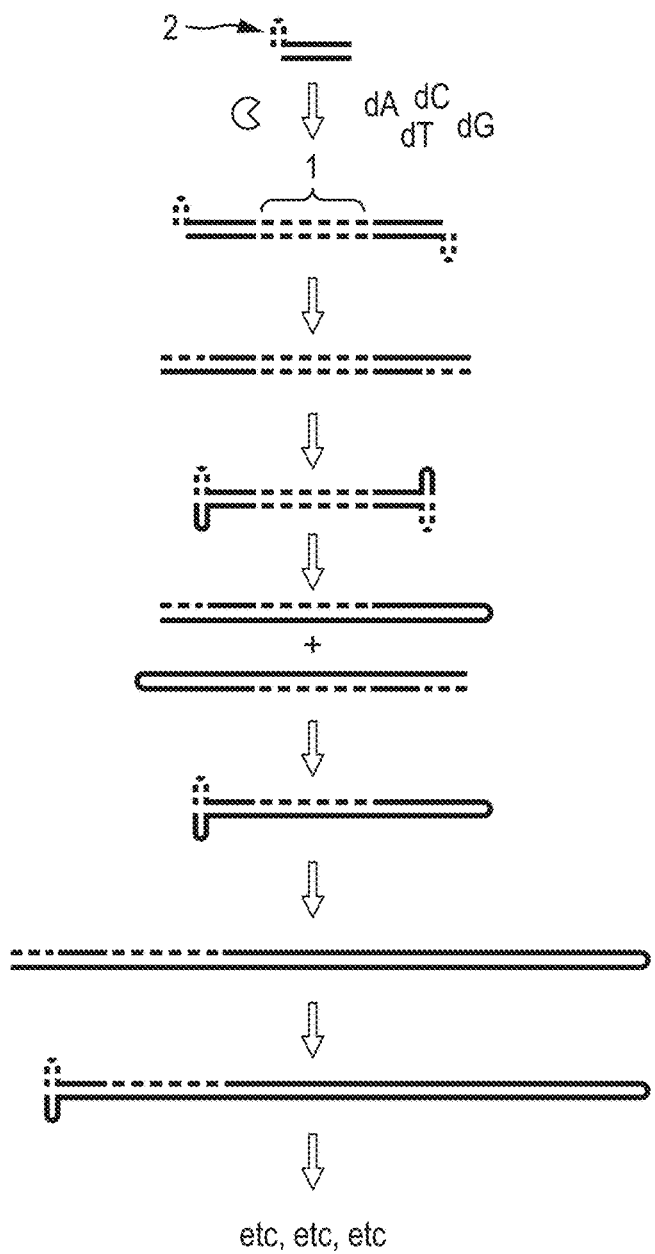
Figure 4A:
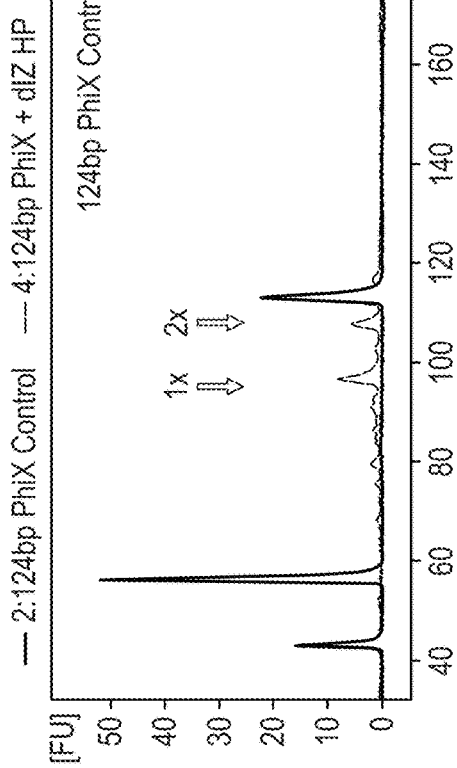
FIGS. 4A-4C show the results of analysing the products obtained when adaptors comprising a 5' dGTAC hairpin (FIG. 4B) or a 5' dITAZ hairpin (FIG. 4C) are ligated to a 124 bp polynucleotide (a PCR product which has been end repaired and polyA tailed) on an Agilent chip.
Figure 4B:
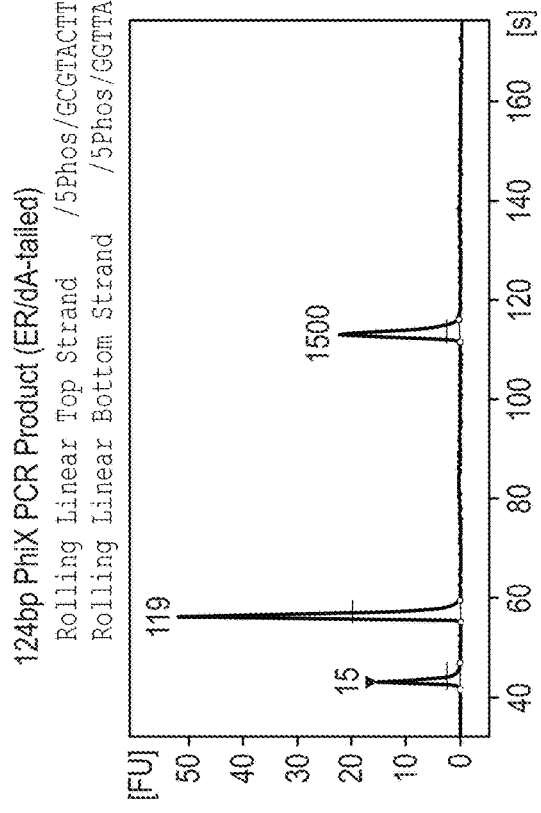
Figure 4C:
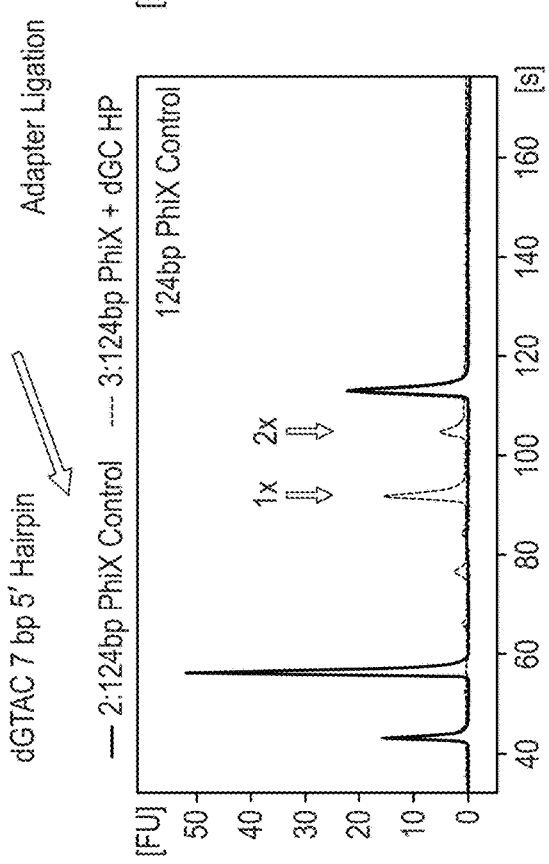
Figure 5A:
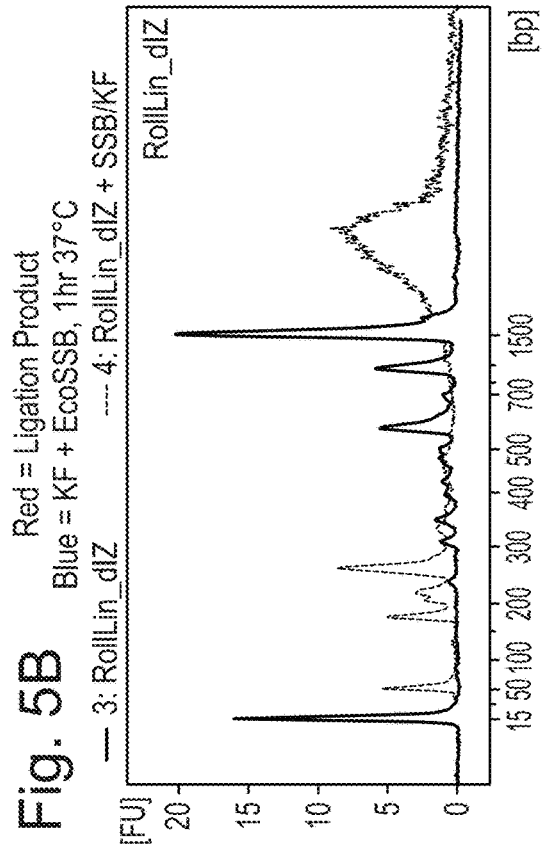
FIGS. 5A-5C show the results of analysing the products obtained when polymerase and SSB are added to the 124 bp polynucleotide to which adaptors have been ligated.
Figure 5B:
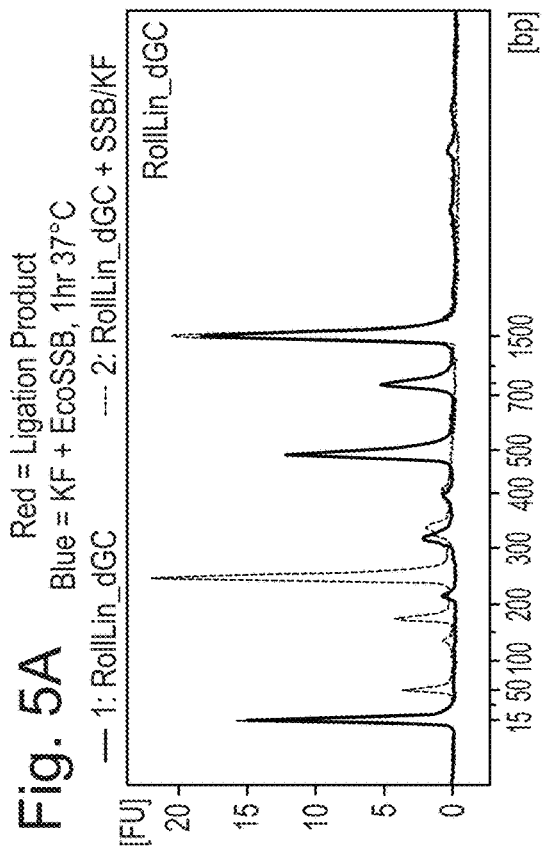
Figure 5C:
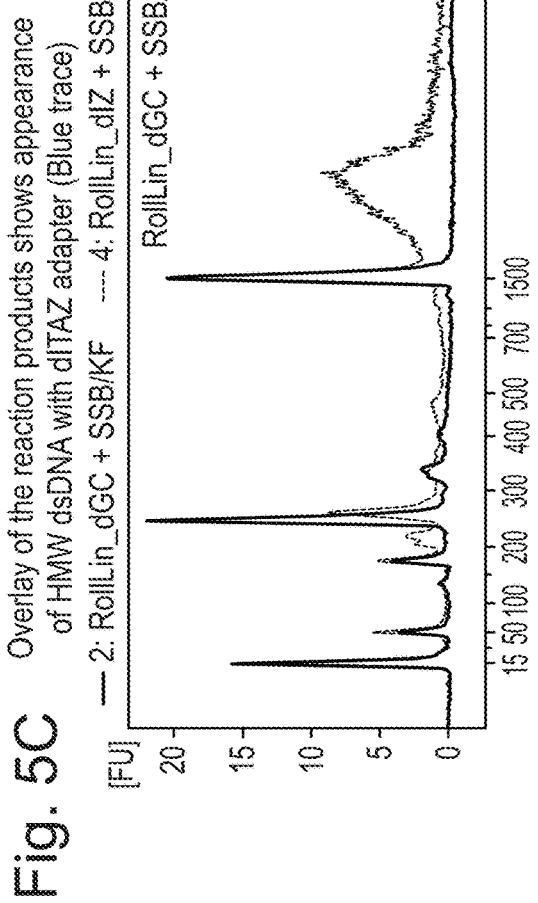
Figure 6A:
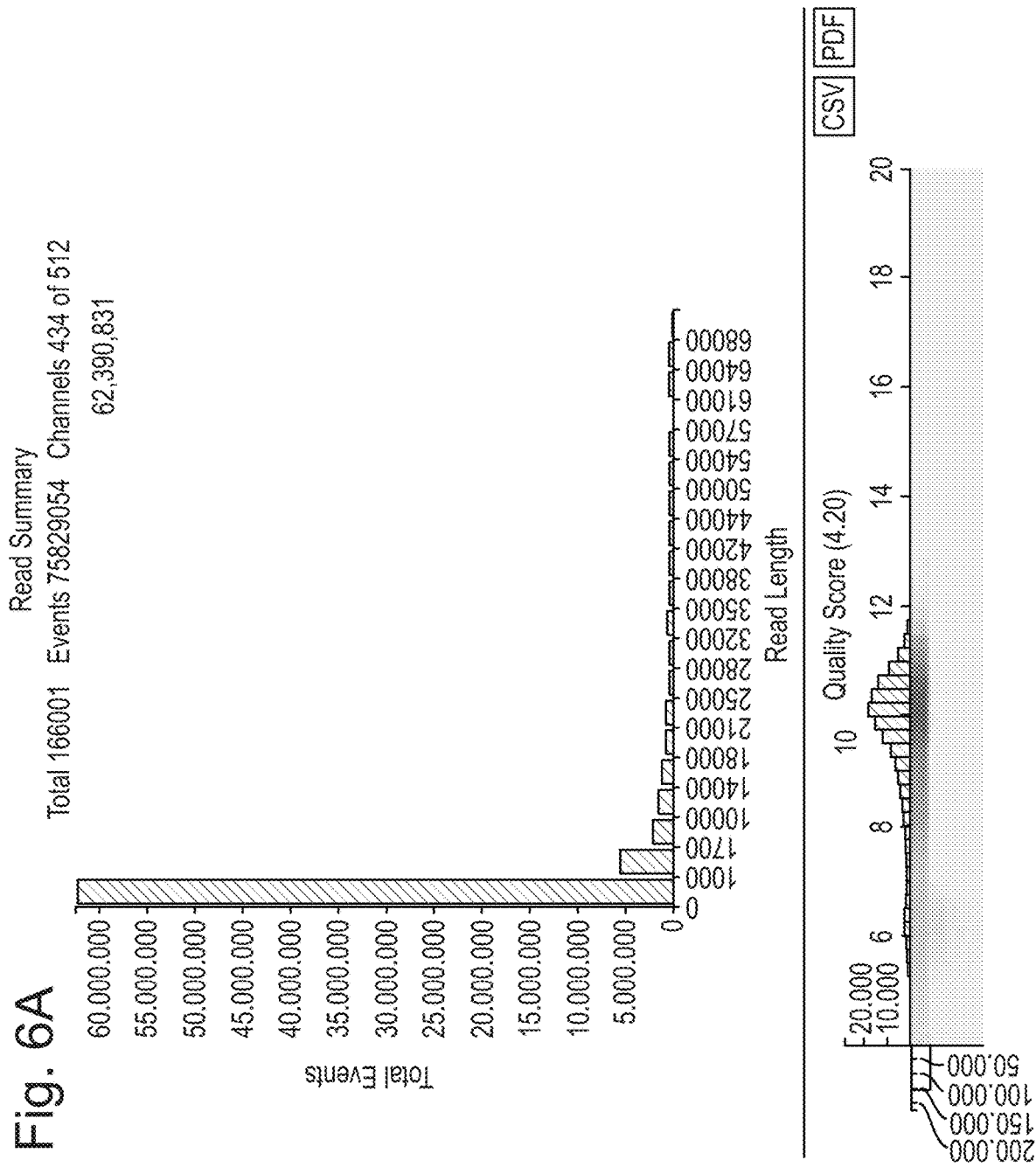
FIGS. 6A-6B show electrophysiology data obtained using Oxford Nanopore Technology's MinION DNA sequencing device.
Figure 6B:
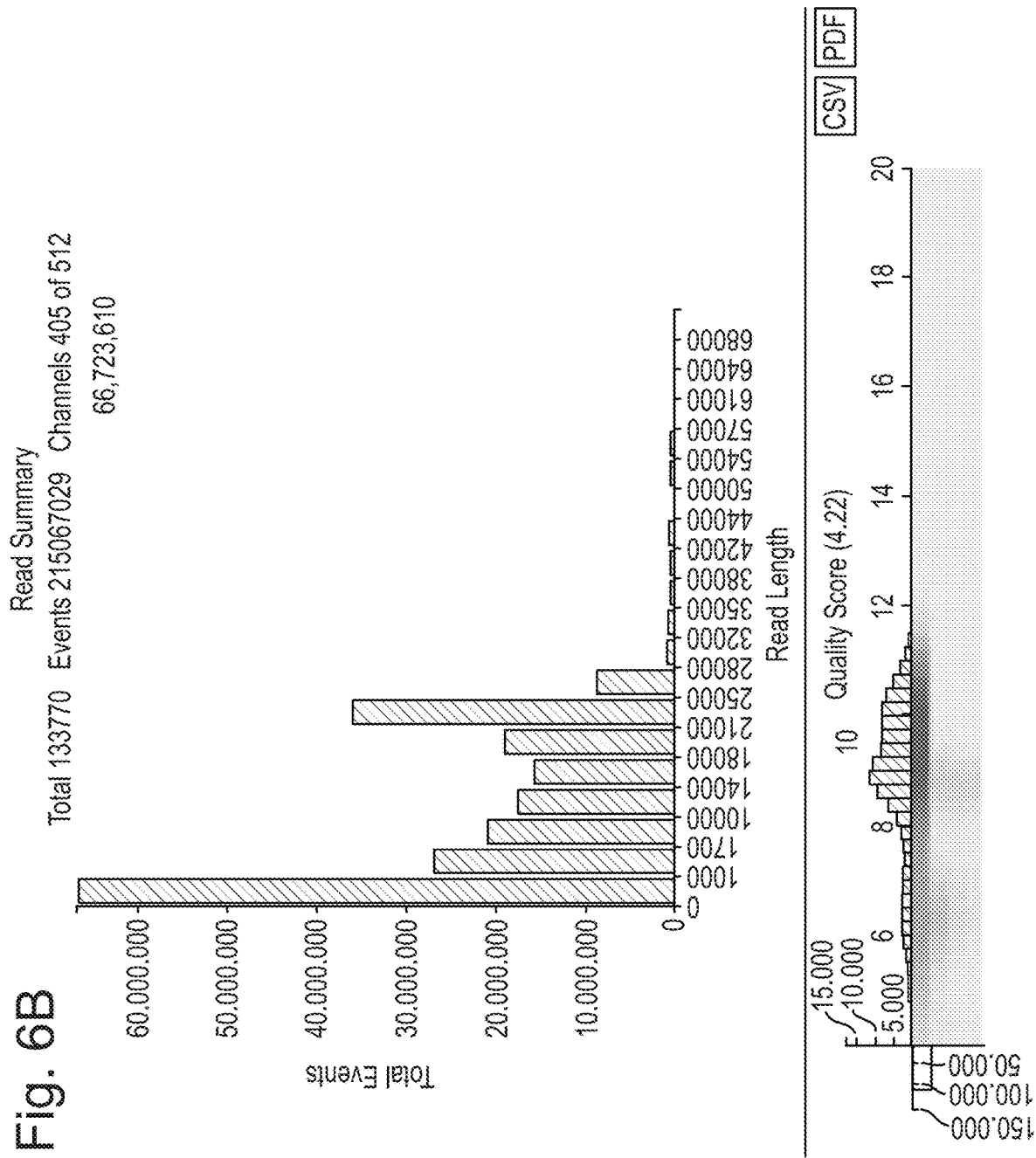

SEQ ID NO: 1 is the top strand of a control DNA adaptor comprising a 5' hairpin-forming sequence comprising only dGTAC nucleotides.

SEQ ID NO: 2 is the top strand of a DNA adaptor comprising a 5' hairpin-forming sequence comprising dITAZ nucleotides.

SEQ ID NO: 3 is the bottom strand of both the control DNA adaptor and the DNS adaptor disclosed herein.

SEQ ID NO: 4 is the sequence of a 5' dITAZ tail added to PCR primers.

SEQ ID NO: 5 is the top strand of a DNA adaptor comprising a 5' hairpin-forming sequence comprising dITAZ nucleotides (RLA_Top).

SEQ ID NO: 6 is the top strand of a DNA adaptor comprising a 5' hairpin-forming sequence comprising dITAZ nucleotides (RLA_Top-Da).

SEQ ID NO: 7 is the top strand of a DNA adaptor comprising a 5' hairpin-forming sequence comprising dITAZ nucleotides (RLA_Top-12bp1).

SEQ ID NO: 8 is the top strand of a DNA adaptor comprising a 5' hairpin-forming sequence comprising dITAZ nucleotides (RLA_Top-12bp2).

SEQ ID NO: 9 is the bottom strand of a DNA adaptor that comprises a restriction site for SpeI and hybridises to each of SEQ ID NOs: 5 to 8 with a single base pair mismatch in the region of the restriction site (RLA_btm_v2_SpeI).

SEQ ID NO: 10 is the bottom strand of a DNA adaptor that is complementary to and hybridises to each of SEQ ID NOs: 5 to 8 (RLA_btm_v2).

SEQ ID NO: 11 is the top strand of a DNA adaptor comprising a 5' hairpin-forming sequence comprising dITAZ nucleotides.

DETAILED DESCRIPTION

It is to be understood that different applications of the disclosed methods and products may be tailored to the specific needs in the art. It is also to be understood that the terminology used herein is for the purpose of describing particular embodiments of the methods and products only, and is not intended to be limiting.

In addition as used in this specification and the appended claims, the singular forms "a", "an", and "the" include plural referents unless the content clearly dictates otherwise. Thus, for example, reference to "a polynucleotide" includes two or more polynucleotides, reference to "an anchor" refers to two or more anchors, reference to "a helicase" includes two or more helicases, and reference to "a transmembrane pore" includes two or more pores and the like.

All publications, patents and patent applications cited herein, whether supra or infra, are hereby incorporated by reference in their entirety.

Amplification Method

The inventors have devised a method of amplifying a polynucleotide, comprising:

(a) providing a template polynucleotide comprising a 5' hairpin, a target polynucleotide and a 3' hairpin, wherein the 5' hairpin comprises one or more non-canonical nucleotides;

(b) contacting the template polynucleotide with a polymerase and canonical nucleotides, wherein:
  (i) the polymerase extends, using the canonical nucleotides, the template polynucleotide from its 3' end to form a first extended polynucleotide comprising the 5' hairpin at its 5' end and the complement of the 5' hairpin at its 3' end, wherein the complement of the 5' hairpin forms a 3' hairpin; and
  (ii) the polymerase extends the first extended polynucleotide from its 3' end to form a second extended polynucleotide comprising the 5' hairpin at its 5' end and the complement of the 5' hairpin at its 3' end, wherein the complement of the 5' hairpin forms a 3' hairpin.

The extended polynucleotides in the method comprise, like the starting template polynucleotide, a 5' hairpin that contains at least one non-canonical nucleotide and a 3' hairpin. Therefore each extended polynucleotide can function as a template polynucleotide and be extended by the polymerase to produce a further extended polynucleotide that comprises a 5' hairpin that contains at least one non-canonical nucleotide and a 3' hairpin.

Thus, the polymerase can extend the second extended polynucleotide from its 3' end to form a third extended polynucleotide comprising the 5' hairpin at its 5' end and the complement of the 5' hairpin at its 3' end, wherein the complement of the 5' hairpin forms a 3' hairpin. The polymerase can extend the third extended polynucleotide, and optionally any further extended polynucleotides produced by extending the third extended polynucleotide and/or by subsequent extensions, to produce further extended polynucleotides comprising the 5' hairpin at their 5' ends and the complement of the 5' hairpin at their 3' ends, wherein the complement of the 5' hairpin forms a 3' hairpin.

The amplification cycle, i.e. polymerase extension from the 3' hairpin to synthesise the complement of the polynucleotide strand comprising a 5' hairpin having at least one non-canonical nucleotide, can be repeated multiple times, such as from 1, 2, 3, 4, 5, 6. 7, 8, 9 or 10 times up to about 20, 30, 40, 50, 100, 200, 300, 400 or 500 times.

In one embodiment, the amplification cycle can be repeated until the extension product is of a desired length. For example, the amplification cycle can be repeated until the extension product is from 50 base pairs in length, such as from 100 base pairs, 500 base pairs, 1 kb, 10 kb, 100 kb, 250 kb or 500 kb, to over 1000 kb in length, such as from 2000 kb, 5000 kb or 10,000 kb.

The method may be carried out such that steps (a) and (b) are performed sequentially or simultaneously.

In one embodiment, provided is a method of amplifying a target polynucleotide, comprising:

a) providing a template polynucleotide comprising a 5' hairpin, a target polynucleotide and a 3' hairpin, wherein the 5' hairpin comprises canonical nucleotides;

b) contacting the template polynucleotide with a polymerase and at least one non-canonical nucleotides, wherein:
  (i) the polymerase extends, the template polynucleotide from its 3' end to form a first extended polynucleotide comprising the 5' hairpin at its 5' end and the complement of the 5' hairpin at its 3' end, wherein the complement of the 5' hairpin forms a 3' hairpin; and
  (ii) the polymerase extends the first extended polynucleotide from its 3' end to form a second extended polynucleotide comprising the 5' hairpin at its 5' end and the complement of the 5' hairpin at its 3' end, wherein the complement of the 5' hairpin forms a 3' hairpin.

In this embodiment, the 5' hairpin may contain only canonical nucleotides and the complementary sequence is synthesised using at least one non-canonical nucleotides, it is more energetically favourable for the ends of the extended polynucleotide to form a 3' hairpin and a 5' hairpin, than for the 3' and 5' ends of the extended polynucleotide to hybridise to one another. Therefore, in the extended polynucleotide, the original 5' hairpin and a new 3' hairpin form rapidly after synthesis of the extension complementary to the original polynucleotide strand. The newly formed 3' hairpin provides a site from which a polymerase can initiate to copy the extended polynucleotide so that the whole cycle can be repeated. This cycle can be repeated multiple times.

Hairpin structures can be formed in ways other than using non-canonical nucleotides. For example, as the ends of double-stranded DNA are in a dynamic equilibrium between a melted single strand form and an annealed double strand form, hairpins may form at the ends of double stranded DNA when palindromic complementary sequences are present at the ends of the DNA strands. The formation of hairpins can be influenced in such DNA molecules by increasing the AT content and/or by including repeating sequences to increase the probability of hairpin formation by weakening the double-stranded conformation. The use of non-canonical nucleotides in the present disclosure is advantageous over the use of repeating AT-containing sequences because it is more energetically favourable for a hairpin between canonical nucleotides to form at the 3' end of the newly synthesized strand, than for a double-stranded polynucleotide to form between non-canonical nucleotides and canonical nucleotides. Hence, rather than being in an equilibrium where there is a limited probability that a hairpin will form, the formation of a hairpin is guaranteed. This means that more, longer amplification products containing more copies of the target polynucleotide will be produced.

5' Hairpin

The 5' hairpin may be of any length. For example, the hairpin may comprise from 2 to 20 base paired nucleotides, such as 3, 4, 5, 6, 7, 8, 9, 10, 12 or 15 base paired nucleotides.

A nucleic acid hairpin is also known as a stem-loop, typically comprising a double-stranded stem portion of base-paired nucleotides, and a single-stranded loop portion of non-base-paired nucleotides joining the two strands of the stem.

Thus, the 5' hairpin may comprise a stem portion and a loop portion.

In some embodiments, the stem of the 5' hairpin is about 5 to about 15 nucleotides in length, for example 5, 6, 7, 8, 9, 10, 11, 12, 13, 14 or 15 nucleotides in length. Thus, the stem may comprise about 5 to about 15 nucleotide base-pairs forming a double-stranded polynucleotide segment.

In some embodiments, the loop of the 5' hairpin comprises about 2 to about 10 nucleotides, for example 2, 3, 4, 5, 6, 7, 8, 9 or 10 nucleotides.

The 5' hairpin comprises at least one non-canonical nucleotide. Any non-canonical nucleotide that can form a base pair with a canonical nucleotide can be used. As used herein the term non-canonical nucleotide includes any nucleotide that comprises a base other than guanine (G), thymine (T), adenine (A), cytosine (C) and uracil (U). Examples of suitable non-canonical nucleotides include inosine, zebularine, 2-amino-adenine (e.g. 2-amino-dA), 2-thiothymine and 2-aminopurine. Inosine is a universal nucleotide. In particular, it can form base pairs with cytosine, uracil, adenine, or zebularine. Zebularine is similar to cytosine and so can form a base pair with guanine or inosine. 2-amino-dA can form base pairs with thymine or inosine. Preferably the hairpin comprises zebularine and inosine. In one embodiment, the zebularine and inosine nucleotides are positioned in the polynucleotide so that they base pair with each other in the hairpin.

The non-canonical nucleotide may be a modified nucleotide, including a modified G, T, A, C or U. The non-canonical nucleotide may comprise methylcytosine, 2,6-Diaminopurine-2'-deoxyriboside, 2-Aminopurine-2'-deoxyriboside, 2,6-Diaminopurine-riboside, 2-Aminopurine-riboside, Pseudouridine, Puromycin, 2,6-Diaminopurine-2'-O-methylriboside, 2-Aminopurine-2'-O-methylriboside and Aracytidine.

The non-canonical nucleotide may be a universal nucleotide. A universal nucleotide is one which will hybridise or bind to some degree to all of the nucleotides in the template polynucleotide. A universal nucleotide is preferably one which will hybridise or bind to some degree to any two or more, such as any three, any four or all, of nucleotides comprising A, T, G, C and U. The universal nucleotide may hybridise or bind more strongly to some nucleotides than to others. For instance, I will show a preferential order of pairing of I-C>I-A>I-G approximately =I-T.

The universal nucleotide may comprise one of the following bases: hypoxanthine, 4-nitroindole, 5-nitroindole, 6-nitroindole, formylindole, 3-nitropyrrole, nitroimidazole, 4-nitropyrazole, 4-nitrobenzimidazole, 5-nitroindazole, 4-aminobenzimidazole or phenyl (C6-aromatic ring). The universal nucleotide may comprises one of the following nucleosides: 2'-deoxyinosine, inosine, 7-deaza-2'-deoxyinosine, 7-deaza-inosine, 2-aza-deoxyinosine, 2-aza-inosine, 2-0'-methylinosine, 4-nitroindole 2'-deoxyribonucleoside, 4-nitroindole ribonucleoside, 5-nitroindole 2'-deoxyribonucleoside, 5-nitroindole ribonucleoside, 6-nitroindole 2'-deoxyribonucleoside, 6-nitroindole ribonucleoside, 3-nitropyrrole 2'-deoxyribonucleoside, 3-nitropyrrole ribonucleoside, an acyclic sugar analogue of hypoxanthine, nitroimidazole 2'-deoxyribonucleoside, nitroimidazole ribonucleoside, 4-nitropyrazole 2'-deoxyribonucleoside, 4-nitropyrazole ribonucleoside, 4-nitrobenzimidazole 2'-deoxyribonucleoside, 4-nitrobenzimidazole ribonucleoside, 5-nitroindazole 2'-deoxyribonucleoside, 5-nitroindazole ribonucleoside, 4-aminobenzimidazole 2'-deoxyribonucleoside, 4-aminobenzimidazole ribonucleoside, phenyl C-ribonucleoside, phenyl C-2'-deoxyribosyl nucleoside, 2'-deoxynebularine, 2'-deoxyisoguanosine, K-2'-deoxyribose, P-2'-deoxyribose and pyrrolidine.

The non-canonical nucleotide may comprise a chemical atom or group that is not present in a canonical nucleotide, such as a propynyl group, a thio group, an oxo group, a methyl group, a hydroxymethyl group, a formyl group, a carboxy group, a carbonyl group, a benzyl group, a propargyl group or a propargylamine group. The chemical group or atom may be or may comprise a fluorescent molecule, biotin, digoxigenin, DNP (dinitrophenol), a photo-labile group, an alkyne, DBCO, azide, free amino group, a redox dye, a mercury atom or a selenium atom. Commercially available nucleosides comprising such chemical groups that may be present in the non-canonical nucleotide include, but are not limited to, 6-Thio-2'-deoxyguanosine, 7-Deaza-2'-deoxyadenosine, 7-Deaza-2'-deoxyguanosine, 7-Deaza-2'-deoxyxanthosine, 7-Deaza-8-aza-2'-deoxyadenosine, 8-5'(5'S)-Cyclo-2'-deoxyadenosine, 8-Amino-2'-deoxyadenosine, 8-Amino-2'-deoxyguanosine, 8-Deuterated-2'-deoxyguanosine, 8-Oxo-2'-deoxyadenosine, 8-Oxo-2'-deoxyguanosine, Etheno-2'-deoxyadenosine, N6-Methyl-2'-deoxyadenosine, O6-Methyl-2'-deoxyguanosine, O6-Phenyl-2'deoxyinosine, 2'-Deoxypseudouridine, 2-Thiothymidine, 4-Thio-2'-deoxyuridine, 4-Thiothymidine, 5' Aminothymidine, 5-(1-Pyrenylethynyl)-2'-deoxyuridine, 5-(C2-EDTA)-2'-deoxyuridine, 5-(Carboxy) vinyl-2'-deoxyuridine, 5,6-Dihydro-2'-deoxyuridine, 5,6-Dihydrothymidine, 5-Bromo-2'-deoxycytidine, 5-Bromo-2'-deoxyuridine, 5-Carboxy-2'-deoxycytidine, 5-Fluoro-2'-deoxyuridine, 5-Formyl-2'-deoxycytidine, 5-Hydroxy-2'-deoxycytidine, 5-Hydroxy-2'-deoxyuridine, 5-Hydroxymethyl-2'-deoxycytidine, 5-Hydroxymethyl-2'-deoxyuridine, 5-Iodo-2'-deoxycytidine, 5-Iodo-2'-deoxyuridine, 5-Methyl-2'-deoxycytidine, 5-Methyl-2'-deoxyisocytidine, 5-Propynyl-2'-deoxycytidine, 5-Propynyl-2'-deoxyuridine, 6-O-(TMP)-5-F-2'-deoxyuridine, C4-(1,2,4-Triazol-1-yl)-2'-deoxyuridine, C8-Alkyne-thymidine, dT-Ferrocene, N4-Ethyl-2'-deoxycytidine, O4-Methylthymidine, Pyrrolo-2'-deoxycytidine, Thymidine Glycol, 4-Thiouridine, 5-Methylcytidine, 5-Methyluridine, Pyrrolocytidine, 3-Deaza-5-Aza-2'-O-methylcytidine, 5-Fluoro-2'-O-Methyluridine, 5-Fluoro-4-O-TMP-2'-O-Methyluridine, 5-Methyl-2'-O-Methylcytidine, 5-Methyl-2'-O-Methylthymidine, 2',3'-Dideoxyadenosine, 2',3'-Dideoxycytidine, 2',3'-Dideoxyguanosine, 2',3'-Dideoxythymidine, 3'-Deoxyadenosine, 3'-Deoxycytidine, 3'-Deoxyguanosine, 3'-Deoxythymidine and 5'-O-Methylthymidine.

The non-canonical nucleotide may comprise a halogen atom. The halogen atom may be attached to any position on the nucleotide, such as the base and/or the sugar. The halogen atom may be fluorine (F), chlorine (Cl), bromine (Br) or iodine (I). Commercially available nucleosides comprising a halogen atom that may be present in the non-canonical nucleotide include, but are not limited to, 8-Bromo-2'-deoxyadenosine, 8-Bromo-2'-deoxyguanosine, 5-Bromouridine, 5-Iodouridine, 5-Bromouridine, 5-Iodouridine, 5'-Iodothymidine and 5-Bromo-2'-O-methyluridine.

In the 5' hairpin, one or more of the base paired nucleotides may comprise one non-canonical nucleotide or two non-canonical nucleotides. For example, from 2 to 20, such as 3, 4, 5, 6, 7, 8, 9, 10, 12 or 15 base paired nucleotides in the hairpin may each comprise one non-canonical nucleotide or two non-canonical nucleotides. In one embodiment, at least about 10%, 20%, 30%, 40% or 50% of the base paired nucleotides in the hairpin each comprise one or two non-canonical nucleotides, preferably two non-canonical nucleotides. In one embodiment, up to about 60%, 70%, 80%, 90% or more, such as 100%, of the base paired nucleotides in the hairpin each comprise one or two non-canonical nucleotides, preferably two non-canonical nucleotides.

Each non-canonical nucleotide is typically capable of base pairing with one or more canonical nucleotide. In the method disclosed herein, a polymerase will typically incorporate a canonical base, e.g. A, C, G or T, opposite the non-canonical nucleotide. Preferably, each non-canonical nucleotide is capable of base pairing with one of the canonical nucleotides G and C, or modified versions thereof, but forms only two hydrogen bonds when base pairing (in contrast to the three hydrogen bonds formed in a G-C base pair). Examples of non-canonical nucleotides capable of forming two hydrogen bonds when base pairing with the canonical nucleotides G and C, or modified versions thereof, include inosine and zebularine.

In this embodiment, when a non-canonical nucleotide is present in a template strand, a polymerase will typically preferentially incorporate a G or C, or a modified version thereof, opposite the non-canonical nucleotide. By way of example, a polymerase may preferentially incorporate cytosine opposite inosine, and guanine opposite zebularine.

Thus, in the method of the invention, the 5' hairpin comprising non-canonical nucleotides, for example inosine and zebularine, may act as a template for the polymerase to form a complementary strand comprising the canonical nucleotides cytosine and guanine, or modified versions thereof, thus facilitating the separation of the two complementary strands and hairpin formation as described herein.

The hairpin typically comprises two or more, such as 3, 4, 5, 6, 7, 8 or more, central nucleotides that do not form a base pair in the hairpin structure, but form a loop. Any nucleotides may be present in the loop, including canonical and/or non-canonical nucleotides. All of the nucleotides in the loop may be identical, for example polyT, polyA, polyC, polyG, polyI or polyZ, or the loop may comprise more than one type of nucleotide.

Hence the hairpin may be formed from a single-stranded polynucleotide of from about 7 to about 50 or more nucleotides, such as from about 10 to about 40, about 15 to about 30 or about 20 nucleotides. The outer nucleotides form base pairs and the central nucleotides form a loop.

The hairpin may be present in an adaptor, or primer, that comprises additional nucleotides. The additional nucleotides may in some embodiments be for the purposes described below. The adaptor and/or primer may include additional nucleotides at either or both sides of the hairpin in the adaptor. For example, the additional nucleotides may be present in the adaptor 5' and/or 3' to the hairpin. Preferably, the additional nucleotides are present at the 3' side of a 5' hairpin, or at the 5' side of a 3' hairpin.

The adaptor or primer may be of any suitable length. For example, the length of the adaptor and/or primer may be from about 8 to about 100, such as about 10 to about 90, about 20 to about 80, about 30 to about 70 or about 40, 50 or 60 nucleotides.

The 5' hairpin adaptor may comprise, in some embodiments, one or more spacer. When present, the spacer is preferably located 5' of the 5' hairpin in the adaptor. In the disclosed method, polymerase activity may be terminated when it reaches the spacer after synthesising the sequence complementary to the 5' hairpin. Spacers are well known in the art and include, for example, one or more iSpC3 groups (i.e. nucleotides which lack sugar and a base), one or more photo-cleavable (PC) groups, one or more hexandiol groups, one or more spacer 9 (iSp9) groups, one or more spacer 18 (iSp18) groups, a polymer or one or more thiol connections. The one or more spacers may comprise any combination of these groups. Many of these groups are commercially available from IDT® (Integrated DNA Technologies®).

Termination of RLA Using a Modified Adapter

By incorporating a selectively cleavable group, such as a modified base, into the 5' hairpin, or 5' hairpin adaptor, then rolling linear amplification can be terminated at a defined time point in the reaction by selectively targeting the introduced modified base with an enzyme that specifically cleaves the sequence at that modified base. The modified base may, for example, be incorporated into the 5' hairpin, either into the loop or stem portion of the hairpin. Alternatively, the modified base may be included in the adaptor at the 5' side, or preferably at the 3' side of the 5' hairpin in the adapter. This means that all product will end at the completion of a repeat copying event and produce a double stranded DNA end, which might be suitable for ligation. One example of a suitable position for incorporating a modified base is shown below, underlined.

(SEQ ID NO: 11)
IZITAZTTTTTAITAZIZTT<u>T</u>GCTTACGGTTCACTACTCACGACGATGT

Examples of suitable modified bases that may be used in this regard include RNA bases for use with RNaseH, inosine for use with hAAG and T7 endonuclease, or deoxyuridine and USER. The 5' hairpin, or 5' hairpin adaptor, may include one or more, such as, for example 2 or 3 such modified bases, which may be different to enable the used a choice of cleavage options.

Therefore, in some embodiments, the adaptor comprises a selectively cleavable group. In some embodiments, the adaptor comprises a hairpin forming region, including a stem-loop-stem, and a selectively cleavable group.

Barcoding of RLA Products Using a Modified Adapter

For further characterisation of single DNA molecules, a barcode can be incorporated into the double stranded DNA portion of the adapter. This allows for identification of single molecules within a sample or for identification of different samples when run as a mix in one sequencing assay. Therefore, in some embodiments, the adaptor comprises a barcode region. In some embodiments, the adaptor comprises a hairpin forming region, including a stem-loop-stem, and a barcode. The adaptor may comprise a hairpin forming region, including a stem-loop-stem, a barcode and a selectively cleavable group. The selectively cleavable group is preferably located 5' of the barcode. The restriction site may be located either side of the barcode, preferably 5', and is preferably 3' of the cleavable group. The barcode is preferably 3' of the 5' hairpin.

Polynucleotide barcodes are well-known in the art (Kozarewa, I. et al., (2011), *Methods Mol. Biol.* 733, p 279-298). A barcode is a specific sequence of polynucleotide that affects the current flowing through the pore in a specific and known manner.

Digestion of RLA Products

It can prove useful to increase the concentration of analyte in a solution. To achieve this, rolling linear amplification products can be digested into single repeat blocks by incorporation of a restriction site into the adapter. After synthesis the products can then be broken down and analysed further individually. By additionally incorporating barcodes, these can be informatically re-assembled after further analysis if desired. Therefore, in some embodiments, the adaptor comprises a restriction site, or other site at which an enzyme can cut the amplification product. In some embodiments, the adaptor comprises a hairpin forming region, including a stem-loop-stem and a restriction site. The adaptor may additionally comprise a barcode and/or a selectively cleavable group.

Where the restriction site is present in a 5' hairpin adaptor, it may be located 5' or 3', preferably 3', of the 5' hairpin. Where the restriction site is present in a 3' hairpin adaptor, it may be located 5' or 3', preferably 5', of the 3' hairpin.

The selectively cleavable group is preferably located 5' of the barcode. The restriction site may be located either side of the barcode, preferably 5', and is preferably 3' of the cleavable group.

Restriction sites are well known in the art. The skilled person is readily able to identify a restriction site and select an appropriate restriction enzyme.

Template Polynucleotide

The template polynucleotide typically comprises a target polynucleotide flanked by 5' and 3' hairpin-forming sequences.

The 5' hairpin may have the characteristics described above.

In the initial template polynucleotide, the 3' hairpin may be a complement of the 5' hairpin that typically comprises only canonical (i.e. GTAC) nucleotides, or may be any polynucleotide that forms a hairpin. The 3' hairpin may be of any length. For example, the hairpin may comprise from 2 to 20 base paired nucleotides, such as 3, 4, 5, 6, 7, 8, 9, 10, 12 or 15 base paired nucleotides. The hairpin typically comprises two or more, such as 3, 4, 5, 6, 7, 8 or more, central nucleotides that do not form a base pair in the hairpin structure, but form a loop. Any nucleotides may be present in the loop, including canonical and/or non-canonical nucleotides. The nucleotides in the loop may be identical, for example polyT, polyA, polyC, polyG, or the loop may comprise more than one type of nucleotide.

In any extended polynucleotide that serves as a subsequent template polynucleotide for further extension by a polymerase, the 3' hairpin is the complement of the 5' hairpin and comprises only canonical (i.e. GTAC) nucleotides.

The template polynucleotide may be single stranded or double stranded. Where the template polynucleotide is double stranded, one or both strands of the template polynucleotide may comprise a 5' hairpin and a 3' hairpin as defined above. Where both strands of the template polynucleotide comprise a 5' hairpin and a 3' hairpin as defined above, both strands of the template polynucleotide are typically extended in the amplification reaction.

In one embodiment, each strand of the double stranded template polynucleotide comprises a 5' hairpin that includes at least one non-canonical nucleotide. It is not essential that a double stranded template polynucleotide comprises a 3' hairpin because the 3' end of each strand of the template polynucleotide can act as an initiation site for the polymerase, such that the polymerase would copy the 5' hairpin on the sense strand to produce a 3' hairpin prior to amplification of the template polynucleotide, in particular the target polynucleotide.

Accordingly, provided is a method comprising providing a double stranded polynucleotide comprising a 5' hairpin that comprises one or more non-canonical nucleotides, and contacting the polynucleotide with a polymerase and canonical nucleotides under conditions suitable for polymerase activity. A single stranded binding protein may also be added with the polymerase.

Where the template polynucleotide is single stranded, the template polynucleotide comprises a 5' hairpin and a 3' hairpin. The 3' hairpin of the single stranded polynucleotide serves as an initiation site for the polymerase.

Target Polynucleotide

A target polynucleotide is used to as a template polynucleotide in the amplification method. The target polynucleotide can be double stranded or single stranded.

The target polynucleotide can be a nucleic acid, such as deoxyribonucleic acid (DNA) or ribonucleic acid (RNA). The template can be single stranded DNA or RNA, double stranded DNA or RNA or a DNA/RNA duplex, e.g. one strand of RNA hybridized to one strand of DNA.

The polynucleotide may be any synthetic nucleic acid known in the art, such as peptide nucleic acid (PNA), glycerol nucleic acid (GNA), threose nucleic acid (TNA), locked nucleic acid (LNA) or other synthetic polymers with nucleotide side chains. The PNA backbone is composed of repeating N-(2-aminoethyl)-glycine units linked by peptide bonds. The GNA backbone is composed of repeating glycol units linked by phosphodiester bonds. The TNA backbone is composed of repeating threose sugars linked together by phosphodiester bonds. LNA is formed from ribonucleotides as discussed above having an extra bridge connecting the 2' oxygen and 4' carbon in the ribose moiety.

The target polynucleotide can be any length. For example, the target polynucleotide can be at least about 10, at least 50, at least 70 at least 100, at least 150, at least 200, at least 250, at least 300, at least 400 or at least 500 nucleotides or nucleotide pairs in length. The target polynucleotide can be up to about 1,000 or more nucleotides or nucleotide pairs, 5,000 or more nucleotides or nucleotide pairs in length, 10,000 or more nucleotides or nucleotide pairs in length 100,000 or more nucleotides or nucleotide pairs in length or 500,000 or more nucleotides or nucleotide pairs in length, or 1,000,000 or more nucleotides or nucleotide pairs in length, or 10,000,000 or more nucleotides or nucleotide pairs in length. The target oligonucleotide is preferably from about 30 to about 100,000 nucleotides in length, such as from about 50 to about 50,000 nucleotides in length, or about 70 to about 10,000 in length.

The target polynucleotide may be a fragment of a longer polynucleotide. In this embodiment, the longer polynucleotide is typically fragmented into multiple, such as two or more, shorter target polynucleotides.

In some embodiments, the method of various aspects described herein may be used to amplify multiple target polynucleotides, such as 2, 3, 4 or 5 to 10, 15, 20 or more polynucleotides, within a sample.

Sample

The target polynucleotides may be present in a sample. The sample may be any suitable sample. The sample may be a biological sample. Any embodiment of the methods described herein may be carried out in vitro on a sample obtained from or extracted from any organism or microorganism. The organism or microorganism is typically archaean, prokaryotic or eukaryotic and typically belongs to one of the five kingdoms: plantae, animalia, fungi, monera and protista. In some embodiments, the methods of various aspects described herein may be carried out in vitro on a sample obtained from or extracted from any virus.

The sample is preferably a fluid sample. The sample typically comprises a body fluid. The body fluid may be obtained from a human or animal. The human or animal may have, be suspected of having or be at risk of a disease. The sample may be urine, lymph, saliva, mucus, seminal fluid or amniotic fluid, but is preferably whole blood, plasma or serum. Typically, the sample is human in origin, but alternatively it may be from another mammal such as from commercially farmed animals such as horses, cattle, sheep or pigs or may alternatively be pets such as cats or dogs.

Alternatively a sample of plant origin is typically obtained from a commercial crop, such as a cereal, legume, fruit or vegetable, for example wheat, barley, oats, canola, maize, soya, rice, bananas, apples, tomatoes, potatoes, grapes, tobacco, beans, lentils, sugar cane, cocoa, cotton, tea or coffee.

The sample may be a non-biological sample. The non-biological sample is preferably a fluid sample. Examples of non-biological samples include surgical fluids, water such as drinking water, sea water or river water, and reagents for laboratory tests.

The sample may be processed prior to being assayed, for example by centrifugation or by passage through a membrane that filters out unwanted molecules or cells, such as red blood cells. The sample may be measured immediately upon being taken. The sample may also be typically stored prior to assay, preferably below −70° C.

In some embodiments, the sample may comprise genomic DNA. The genomic DNA may be fragmented or any of the methods described herein may further comprise fragmenting the genomic DNA. The DNA may be fragmented by any suitable method. For example, methods of fragmenting DNA are known in the art. Such methods may use a transposase, such as a MuA transposase or a commercially available G-tube.

Polymerase

Any suitable polymerase may be used in the method. The polymerase is any enzyme that can initiate synthesis of a polynucleotide complementary to a strand of a template polynucleotide at a 3' end of a polynucleotide strand that is hybridized to its complement in the same or another polynucleotide strand. The polymerase is an enzyme that can synthesise the polynucleotide by adding successive canonical nucleotides to the 3' end to create the complementary polynucleotide. The polymerase continues to synthesise the complementary strand until it reaches the 5' end of the template polynucleotide.

The polymerase is preferably a strand displacing polymerase. A strand displacing polymerase is a polymerase that can displace a polynucleotide that is hybridized to the strand of the template polynucleotide that is being copied as it moves along the template polynucleotide. The displaced strand is typically hybridized closer than the polymerase to the 5' end of the strand of the template polynucleotide that is being copied.

Some examples of polymerases that can be used include but are not limited to BST 2.0 or BST 3.0 (which are commercially available from NEB), PyroPhage® 3173 DNA Polymerase (which is commercially available from Lucigen® Corporation), SD Polymerase (commercially available from Bioron®), Klenow (which is commercially available from NEB), Phi29 DNA polymerase or variants thereof. The polymerase may be a heat stable polymerase, such as Taq polymerase (which is commercially available from Thermo Scientific Enzymes)

A single stranded binding protein (SSB) may be added. The SSB may aid strand displacement. SSBs may be obtained commercially, for example from NEB and Promega.

The polymerase amplifies the polynucleotide by adding free nucleotides. Therefore, nucleotides are added to the reaction. The nucleotides that are added are canonical nucleotides, for example guanine (G), cytosine (C), adenine (A) and threonine (T) or uracil (U). For example, where the template polynucleotide is DNA, dG, dC, dA and dT are added. These are commonly referred to as dNTPs.

Buffers suitable for amplification of polynucleotides are known in the art.

Reaction Conditions

The method may be an isothermal amplification method. Hence in one embodiment, the method is carried out at a constant temperature. The method may, for example, be carried out at a temperature of from about 20° C. to about 70° C., such as at room temperature (RT), about 37° C., about 55° C., or about 65° C. The skilled person will readily be able to determine the optimal temperature for a given polymerase. Higher temperatures, such as 75 to 80° C. may be used when a heat stable polymerase, such as Taq polymerase, is used.

The amplification may be carried out for any suitable period of time. This may depend on the length of the target polynucleotide and/or the desired degree of amplification. For example, the amplification may be allowed to continue for a period of from about 20 minutes or more, such as for example from about 30 minutes or more, preferably from about 45 minutes, about 60 minutes, about 90 minutes, about 2 hours, about 6 hours, about 12 hours to about 24 hours, about 3 days or more.

At the end of the amplification, the reaction mixture may be heated to inactivate the polymerase, for example for heating to at least about 80° C. A higher inactivation temperature, such as at least about 100° C. may be used where a heat stable polymerase, such as Taq polymerase, is used. To inactivate the polymerase, the temperature is held at a temperature of at least about 80° C., or at least about 100° C., for a period of about 5 minutes or longer.

In one embodiment, heat may be used to separate the strands of the template polynucleotide. Alternatively, the pH and/or ionic strength of the reaction mixture may be increased to separate the strands.

Preparation of Template Polynucleotide

The method may comprise an initial step of preparing the template polynucleotide. The template polynucleotide may be prepared by ligating an adaptor comprising a 5' hairpin, or that is designed such that it can form a 5' hairpin, to the 5' ends of each strand of a double stranded target polynucleotide, wherein the 5' hairpin comprises at least one non-canonical nucleotide. The adaptor may be a single stranded adaptor. The adaptor may be a double stranded adaptor. The double stranded adaptor preferably comprises a 3' hairpin, or that is designed such that it can form a 3' hairpin. The 3' hairpin is typically comprised only of canonical nucleotides, but may comprise one or more non-canonical nucleotides. Ligation of a double stranded adaptor comprising the 5' hairpin, or a sequence capable of forming the 5' hairpin, and the 3' hairpin, or a sequence capable of forming the 3' hairpin, to the ends of a target polynucleotide results in the formation of a template polynucleotide comprising a double stranded target polynucleotide flanked by 5' and 3' hairpin-forming sequences at both ends.

Where the target polynucleotide is a double stranded polynucleotide, a single stranded adaptor comprising the 5' hairpin, or a sequence capable of forming the 5' hairpin, or a double stranded adaptor comprising the 5' hairpin, or a sequence capable of forming the 5' hairpin, wherein the strand of the adaptor that is ligated to the 3' end of each strand of the target polynucleotide is shorter than the strand of the adaptor that is ligated to the 5' end of each strand of the target polynucleotide. After ligation, a double stranded template comprising at each end a 5' hairpin, or a sequence capable of forming the 5' hairpin is produced. When the polymerase and canonical nucleotides are added to the double stranded template, the 3' end of each strand of the template polynucleotide is extended to produce a 3' hairpin that is complementary to the 5' hairpin. The 3' hairpin comprises only canonical nucleotides.

The template polynucleotide may be prepared by ligating an adaptor comprising a 5' hairpin to the 5' end of a single stranded target polynucleotide that comprises a 3' hairpin, wherein the 5' hairpin comprises at least one non-canonical nucleotide. The template polynucleotide may be prepared by ligating an adaptor comprising a 5' hairpin to the 5' end of a single stranded target polynucleotide, wherein the 5' hairpin comprises at least one non-canonical nucleotide and by ligating an adaptor comprising a 3' hairpin to the 3' end of the single stranded target polynucleotide. In this embodiment, the adaptor is typically a single stranded adaptor. The 3' hairpin is typically comprised only of canonical nucleotides, but may comprise one or more non-canonical nucleotides.

Ligation may be carried out by methods known in the art. Typically a ligase is used to ligate the adaptor to the target polynucleotide. The double stranded target nucleotide may be blunt ended. The double stranded target nucleotide may be blunt ended by any suitable method, such as for example, end repair. The double stranded target polynucleotide preferably comprises a dA tail, but may alternatively comprise a dG, dC or dT tail. The adaptor may comprise blunt ends at the end that does not comprise the hairpin. The adaptor preferably comprises a dT tail at the end that does not comprise the hairpin, but may alternatively comprise a dG, dC or dA tail. The double stranded target polynucleotide can be ligated via its dA tail to the dT tail in the adaptor. Alternatively, the double stranded target polynucleotide can be hybridized via its other complementary tail to the tail of the adaptor. The hairpin(s) in the adaptor are as described above.

The adaptor may comprise additional nucleotides at the end for ligation to the target polynucleotide. For example, the adaptor may comprise from about 2, 3, 4 or 5 to about 20, 30, 50 or more additional nucleotides and/or base paired nucleotides in addition to the hairpin forming sequence(s), such as from about 10 to about 40 or about 20 to about 30 additional nucleotides and/or base paired nucleotides. The additional nucleotides and/or base paired nucleotides are typically canonical nucleotides.

Adaptors may be ligated to a target polynucleotide without any knowledge of the sequence of the target polynucleotide.

In one embodiment, the double stranded adaptor may be a MuA substrate and a MuA transposase may be used to (i) fragment a polynucleotide to produce the target polynucleotide and (ii) ligate the MuA substrate to the target polynucleotide. Methods for using MuA transposase to ligate adaptors are described in WO 2016/059363.

The template polynucleotide may be prepared by primer hybridization and extension. Amplification by primer addition can be carried out either on known targets, for which at least some sequence information is known, or on random fragments.

For amplification of a desired region of interest primers can be designed according to established methods such as for PCR, etc.

For random fragments an amplification adaptor with primer binding sites is first ligated to the ends of the target polynucleotide, such as for example by using known methods for next-generation sequencing (NGS) library preparation. The target polynucleotide can be either double stranded or single stranded. Methods are known for attaching adaptors to the ends of double stranded polynucleotides and for attaching adaptors to the ends of single stranded polynucleotides.

PCR can be performed before the Linear Rolling Amplification reaction if desired. A polymerase suitable for incorporation of dNTPs opposite deoxyinosine is recommended, such polymerases are well known and one suitable example is Taq polymerase. As with standard PCR reactions, annealing and extension times and temperatures are dependent upon the primer sequence used and these can readily be determined. Accordingly, in the method, the template polynucleotide may be produced by PCR.

Hence in the method, a target polynucleotide may be amplified using: (i) a first primer comprising a 5' hairpin and a sequence at its 3' end that is complementary to a sequence in the 3' end of the first strand of the target polynucleotide; and (ii) a second primer comprising a 5' hairpin and a sequence at its 3' end that is complementary to a sequence in the 3' end of the second strand of the target polynucleotide.

In one embodiment, the target polynucleotide may be produced using an isothermal amplification method using a strand displacing polymerase.

Provided herein is a method of amplifying a polynucleotide, comprising: (a) providing a primer pair, wherein each primer comprises a 5' hairpin that comprises one or more non-canonical nucleotides; (b) contacting a sample comprising a target polynucleotide with the primer pair; and (c) carrying out an amplification reaction using the primer pair.

Amplification Product

A novel amplification product is produced by the method disclosed herein. The amplification product is a polynucleotide obtainable by a method according to any of the methods described herein. The polynucleotide provided herein comprises multiple copies of a target sequence and its complement. The target (Tar) and complement (Com) are present in the sequence in a 5' to 3' direction as follows (Tar-Com)$_x$, wherein x is an integer greater than 2. X may, for example be from 2 to about 100 or more, such as from about 3, 5, 10 or 20 to about 50, 60, 70, 80 or 90.

In the polynucleotide the target and complement sequences closest to the 5' end are separated by the sequence of the initial 3' hairpin (3'H) and any adaptor and/or primer sequence used in the method. Subsequent target and complement repeats are separated by repeats of the same sequence, which is the complement of the 5' hairpin and any adjacent adaptor and/or primer sequence in the original template polynucleotide, but comprised of canonical nucleotides (5'HC). The target sequence closest to the 5' end is the original target sequence (OTar). The original target sequence may contain modifications, such as methyl groups. The 5' hairpin comprising at least one non-canonical nucleotide (5'H) and any adjacent adaptor and/or primer sequences are typically present in the product.

The polynucleotide may thus have the formula 5'H-OTar-3'H-Com-(5'HC-Tar-5'HC-Com-)x, wherein x is an integer. X may, for example be from 1 to about 100 or more, such as from about 3, 5, 10 or 20 to about 50, 60, 70, 80 or 90.

The amplification product may comprises a mixture of polynucleotides of different lengths, wherein each polynucleotide is as defined above. Hence the product may comprises multiple different, such as 2, 3, 4, 5, 10 up to 20, 30, 50, 100 or more polynucleotides as described above wherein x has a different value in each of the different polynucleotides.

Characterisation Method

In one embodiment, the method may be used to detect the presence of a target polynucleotide in a sample. In this embodiment, the presence of an amplification product indicates that the target polynucleotide is present in the sample.

In one embodiment, the amplification product may be used for any desired purpose. In one embodiment, the amplification product is characterised. The characterisation method may comprise gel analysis, detecting pH change due to dNTP incorporation, detecting a change in fluorescence (increase or decrease), detecting turbidity/viscosity, detecting absorbance change (increase or decrease), detecting any reporter on the dNTPs. The characterisation method may utilise a nanopore.

For characterisation, the amplification products can be kept intact, or can be cleaved into the individual units. This can be achieved easily, such as by the incorporation of a restriction site into the hairpin in place of or in addition to a polyT (e.g. TTTT), polyA, polyC or polyG. One advantage of cleavage is that it can lead to an analyte increase.

Provided herein is a method of characterising a polynucleotide, comprising:

(a) contacting the polynucleotide produced by the amplification method with a nanopore such the polynucleotide translocates through the nanopore; and (b) taking one or more measurements as the polynucleotide moves with respect to the nanopore, wherein the measurements are indicative of one or more characteristics of the polynucleotide and thereby characterising the polynucleotide.

The measurements may be, for example, translocation time, reporter incorporation, tag release and/or blob counting.

The amplification product can be sequenced. Any method may be used for sequencing, typically a next generation sequencing method, for example, any method of ensemble or single molecule sequencing. Examples of suitable sequencing methods include standard sequencing by synthesis (SBS) sequencing methods, such as Genia, PacBio, Illumina, Helicos, Solid or 454 methods, and single molecule sequencing methods, which may be either direct or indirect, these can be performed using a nanopore, such as using Oxford Nanopore Technologies' sequencing technology, or via any other known method, such as AFM, Sequencing by Hybridisation or Stratos' Sequencing by Expansion.

Figure 7:
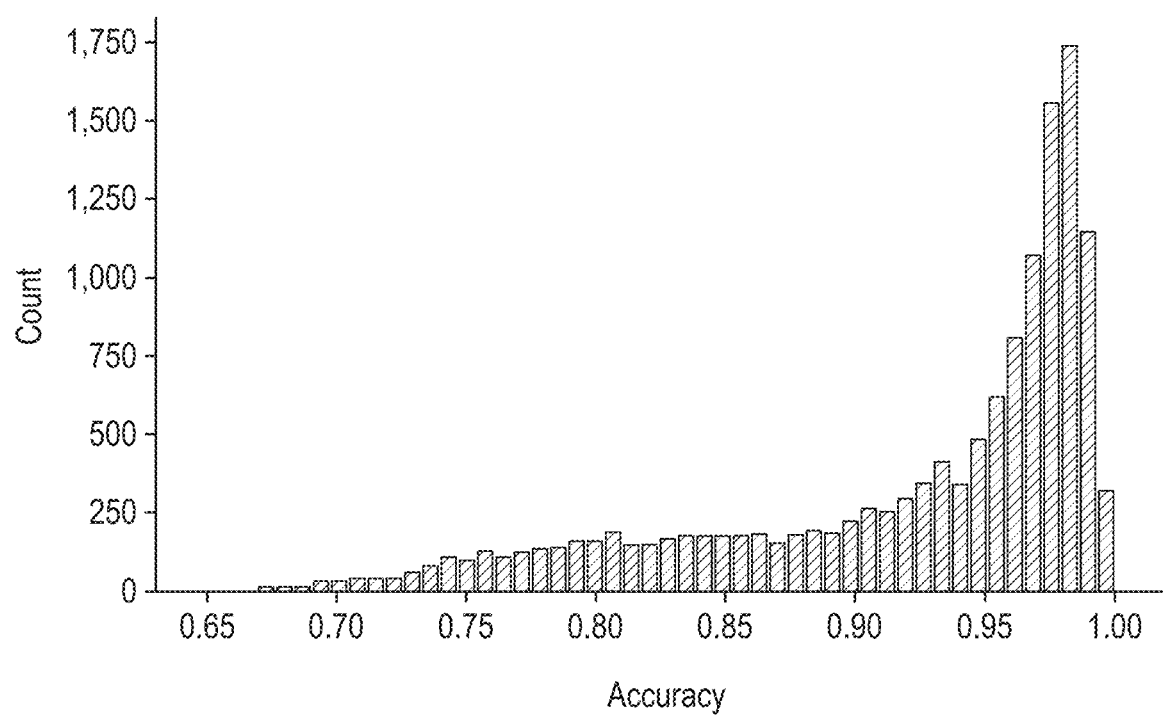
FIG. 7 shows the results of an analysis of the MinION sequencing data from a single repeating molecule obtained using the dITAZ 5' hairpin adaptor. The repeating molecule contains multiple repeats of the target sequence and complement. A consensus pile up of the sequencing data for each repeat was piled up and an accuracy of 98% for the single molecule was obtained.
Figure 8:
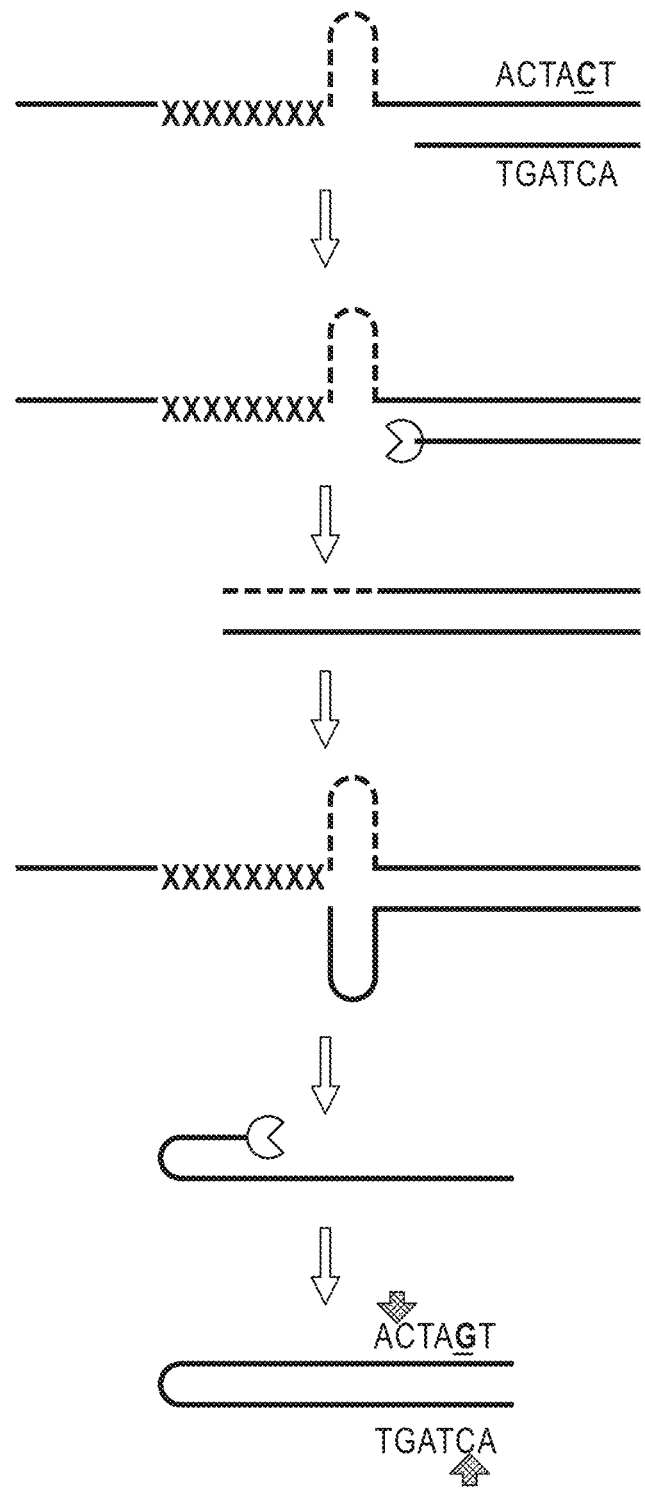
FIG. 8 illustrates the principle behind Example 4. An adapter comprising a top strand that contains a spacer region (XXXXXXXX) and a hairpin-forming IZ-containing region, and an annealed bottom strand comprising a restriction site sequence, wherein the top strand has a base pair mismatch with the bottom strand in the sequence that anneals to the restriction site sequence. A polymerase produces the complement of the hairpin sequence and terminates when it reaches the spacer. The hairpin in the top strand reforms because it is more energetically favourable than binding to its newly synthesised complement, which forms a 3' hairpin on the bottom strand. The 3' hairpin serves as an initiation site for the polymerase which synthesises the complement of the bottom strand. This results in a double stranded product that contains the restriction site, and which can be cleaved by the restriction enzyme (SpeI in Example 4).

Sequencing the amplification product provides a route to enhanced accuracy of the target sequence. Multiple copies of the target sequence and its complement provide sequencing information enabling the sequence of the target polypeptide to be determined with a high degree of accuracy as illustrated in FIG. 7. Typically, the accuracy of sequence determination is 95% or more, such as 98% or more or 99% or more.

The method may further comprise adding sequencing adaptors to one or both ends of the extended polynucleotide.

In one embodiment, a size selection may be performed prior to characterisation. For example long polynucleotides likely to comprise at least about 5, such as at least 10 or more copies of the target sequence may be selected for characterisation.

The amplification method described herein can be used in other applications such as qPCR, LAMP processes, etc.

In one embodiment, the method provides simultaneous amplification and detection/characterisation, such as sequencing by synthesis. As one example, the products of amplification, may be detected and/or characterised by detecting and analysing optical signals using a nanopore sensor, or a zero mode wave guide or Raman spectroscopy. As another example, the products of amplification, may be detected and/or characterised by detecting and analysing non-optical signals using a nanopore sensor, such as a nanopore.

To facilitate such detection and/or characterisation, the nucleotides provided with the polymerase may be labelled, using any suitable optical or non-optical label.

The nucleotides provided with the polymerase may be modified. Typically the modification does not reduce the strength of binding of the nucleotide to its complementary nucleotide in a double-stranded polynucleotide, or hairpin structure.

To facilitate detection and/or characterisation, the template polynucleotide may be tethered to a nanopore sensor, or to a membrane comprising a nanopore sensor. The tether may be included in a sequencing adaptor ligated to an end of the amplification product. Such sequencing adaptors are known in the art, and are disclosed, for example, in WO2012/164270.

Adaptors

Provided is a double stranded polynucleotide adaptor comprising a first strand and a second strand, wherein the first strand comprises a 5' hairpin comprising one or more non-canonical nucleotides, and the second strand comprises a 3' hairpin.

The features of the adaptors and hairpins are as described above.

Primers

Provided is a primer pair, wherein each primer comprises a 5' hairpin that comprises one or more non-canonical nucleotides.

For amplification of a desired region of interest primers can be designed according to established methods such as for PCR, etc. The primer additionally comprises a 5' hairpin as described herein.

The primer is typically a single stranded polynucleotide, such as a single stranded DNA. The primer may, for example, have a length of from at least about 20, 30, 40 or 50 to about 100 nucleotides. The primer may contain a sequence of from about 6, 8, 10, 15, 20 or more nucleotides that is complementary to a sequence in the target polynucleotide or to a sequence in an adaptor that is ligated to the target polynucleotide.

Kits

Provided is a kit for amplifying a target polynucleotide comprising: (i) an adaptor as described herein or a primer pair as described herein; and (ii) a polymerase. The polymerase is preferably a strand displacing polymerase. The kit may further comprise any one or more of the components described herein for use in the amplification method. In one embodiment, the kit may further comprise one or more sequencing adaptors.

The following Examples illustrate the invention.

Example 1: Linear Amplification by Adaptor Ligation

Materials and Methods
Adaptors

Adaptors with the following sequences were prepared at 10 μM by slow cooling from 95° C. to 23° C. at 2° C. min$^{-1}$ in 10 mM Tris-HCl pH7.5, 50 mM NaCl, 0.5 mM EDTA.
Adaptor Sequences:

```
Rolling Linear Top Strand-dGTAC Control
                                         (SEQ ID NO: 1)
/5Phos/GCGTACTTTTTAGTACGCTTTTCGGCGTCTGCTTGGGTGTTTA
ACCT Rolling Linear Top Strand
                                         (SEQ ID NO: 2)
/5Phos/IZITAZTTTTTAITAZIZTTTTCGGCGTCTGCTTGGGTGTTTA
ACCT Rolling Linear Bottom Strand
                                         (SEQ ID NO: 3)
/5Phos/GGTTAAACACCCAAGCAGACGCCG
```

Ligation

Ligation reactions were prepared as follows and left at room temperature for 10 minutes:

| | |
|---|---|
| Adaptor (10 μM) | 5 μl |
| DNA fragment (End-repaired and dA-tailed) | 500 ng |
| NEB Blunt T/A Master Mix 2× | 50 μl |
| Nuclease Free Water | To 100 μl |

Reaction products were purified using Agencourt AMPure XP beads (Beckman Coulter) according to manufacturer's protocol and eluted in 37.5 μl of 10 mM Tris-HCl pH7.5, 50 mM NaCl, 0.5 mM EDTA.

Amplification

Rolling linear amplification reactions were prepared as follows and incubated at 37° C. for 60 minutes then 80° C. for 5 mins to heat inactivate:

| | |
|---|---|
| Ligated DNA (from above) | 15 μl |
| dNTPs (10 mM) | 2 μl |
| NEB Klenow Fragment | 3 μl |
| NEBuffer 2 | 5 μl |
| NEB ET SSB | 1 μl |
| Nuclease Free Water | To 50 μl |

Reaction products were purified using Agencourt AMPure XP beads (Beckman Coulter) according to manufacturer's protocol and eluted in 43 μl of 10 mM Tris-HCl pH7.5, 50 mM NaCl, 0.5 mM EDTA.

Example 2: Sequencing

Nanopore sequencing was performed using Oxford Nanopore Technologies MinION DNA sequencing device with sample preparation kit Ligation Sequencing Kit 1D (SQK-LSK108) according to the manufacturer's protocol.

The results are shown in FIGS. 4 to 7.

Example 3: Linear Amplification by Primer Addition

Materials and Methods
Primers

Primers were designed according to the experiment type and target DNA and remain the user's choice. Primers were tailed at the 5' with the sequence below:

```
                                         (SEQ ID NO: 4)
/5Phos/IZITAZTTTTTAITAZIZTTTT
```

Amplification

Rolling linear amplification reactions were prepared as follows and incubated at 65° C. for 60 minutes then 80° C. for 5 mins to heat inactivate. PCR was performed prior to the amplification reaction. The primers could have been omitted from the rolling linear amplification reaction, but their removal is optional. If PCR was not performed before this step, then the reaction could have been supplemented with 200 nM primers.

| | |
|---|---|
| DNA (200 ng) | 15 μl |
| dNTPs (10 mM) | 2 μl |
| NEB BST 3.0 | 3 μl |
| Isothermal Amplification Buffer 10× | 5 μl |
| NEB ET SSB | 1 μl |
| Nuclease Free Water | To 50 μl |

Reaction products were purified using Agencourt AMPure XP beads (Beckman Coulter) according to manufacturer's protocol and eluted in 43 μl of 10 mM Tris-HCl pH7.5, 50 mM NaCl, 0.5 mM EDTA.

The results obtained were similar to the amplification method which used adaptors to create the template polynucleotide.

Example 4: Alternative Top Strands

A series of top strands with different 5' hairpin compositions were prepared to demonstrate the ability of different 5' hairpin sequences to act as a template for rolling linear amplification (RLA):

```
RLA_Top
                                         (SEQ ID NO: 5)
2GCTTGGGTGTTTAACC8888IZITAZTTTTTAITAZIZTTTTGCTTACG
GTTCACTACTCACGACGATGT

RLA_Top-Da
                                         (SEQ ID NO: 6)
2GCTTGGGTGTTTAACC8888IZITAZAAAAATITAZIZAAAAGCTTACG
GTTCACTACTCACGACGATGT

RLA_Top-12bp1
                                         (SEQ ID NO: 7)
2GCTTGGGTGTTTAACC8888IZIAZIITATIAAAAATZATAZZITZIZA
AAAGCTTACGGTTCACTACTCACGACGATGT

RLA_Top-12bp2
                                         (SEQ ID NO: 8)
2GCTTGGGTGTTTAACC8888ZAITAZITAIIAAAAATZZTAZITAZTIA
AAAGCTTACGGTTCACTACTCACGACGATGT
```

To confirm the abilities of the 5' hairpins to act as templates for rolling linear amplification, a bottom strand was annealed that contained a restriction site for the restriction enzyme SpeI:

```
           RLA_btm_v2_SpeI
                                       (SEQ ID NO: 9)
           5CATCGTCGTGACTAGTGAACCGTAAGC
```

Key: 2: 5' DBCO-TEG
 5: 5' Phosphate
 8: C3 spacer
 I: deoxyinosine
 Z: deoxyzebularine The restriction site is only present in the bottom strand and so on incubation with the cognate enzyme it does not digest. However if, on incubation with a polymerase and nucleotides, the 5' hairpin is able to act as a template for rolling linear amplification then the resultant product will contain a restriction site on both strands of the dsDNA product and so be digested on incubation with the cognate enzyme. This was demonstrated for all of the alternative 5' hairpin sequences tested.

The Top and Bottom strands of the adapter were annealed at 10 μM, from 95° C. at 2° C. min$^{-1}$, in 10 mM Tris pH 7.5, 50 mM NaCl.

Figure 9:
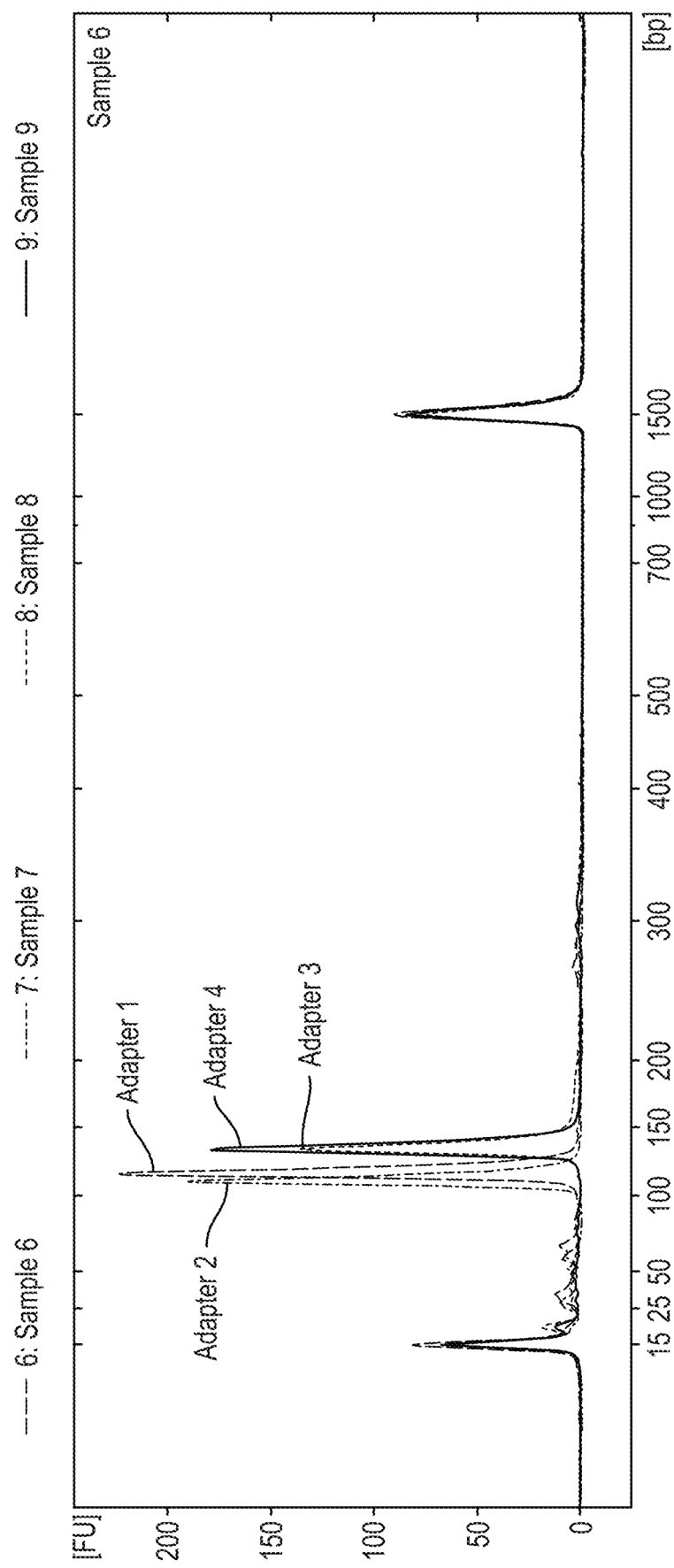
FIG. 9 shows the sizes of hairpin adapters on an Agilent 1000 chip. Adapter 1 is RLA_Top+RLA_btm_v2_SpeI; Adapter 2 is RLA_Top-dA+RLA_btm_v2_SpeI; Adapter 3 is RLA_Top-12bp1+RLA_btm_v2_SpeI; Adapter is RLA_Top-12bp2+RLA_btm_v2_SpeI.
Figure 10:
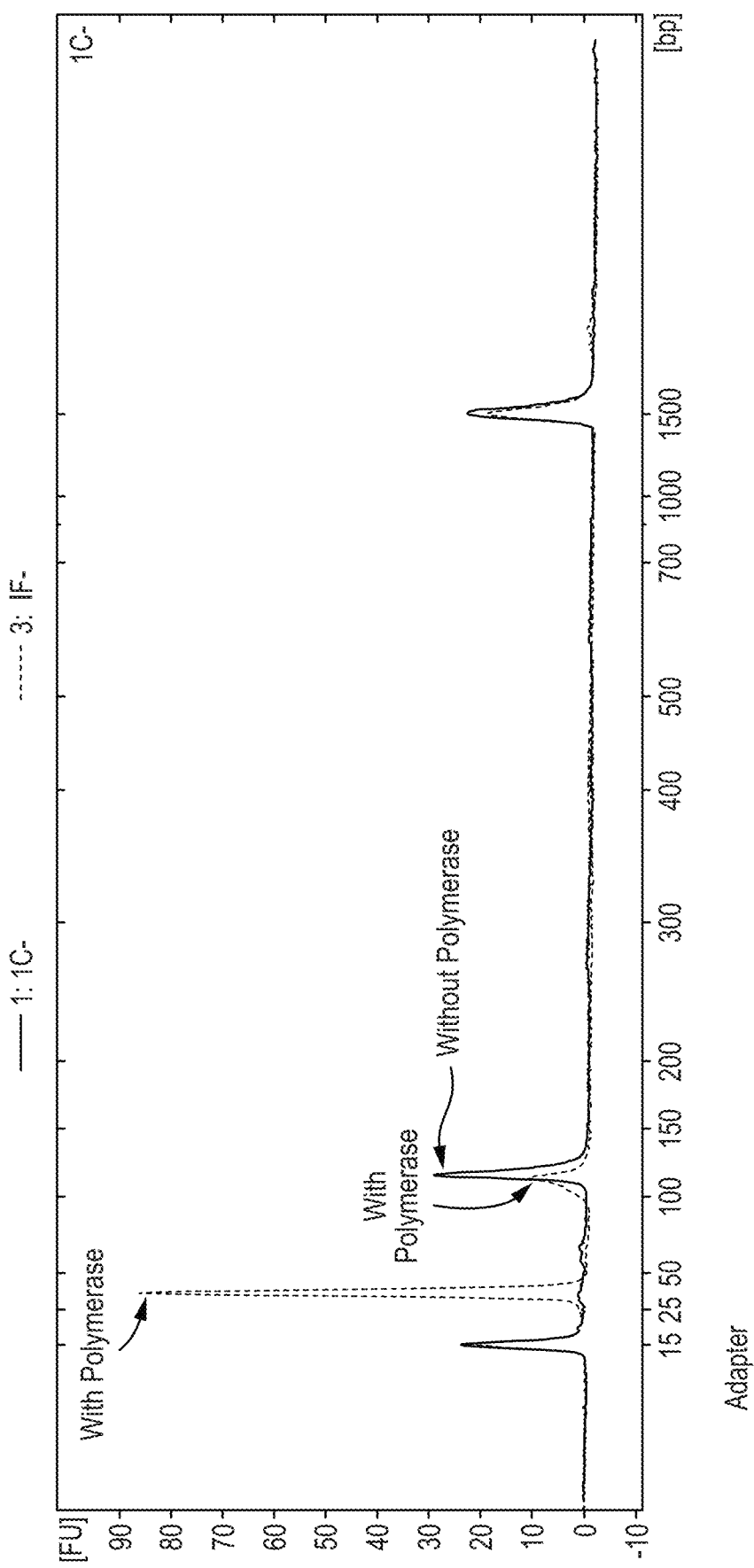
FIG. 10 is an Agilent 1000 chip trace showing the products produced when the polymerase Bst 3.0 is used to fill in the adapter formed by annealing RLA_Top and RLA_btm_v2_SpeI. Traces with and without the polymerase are shown.
Figure 11:
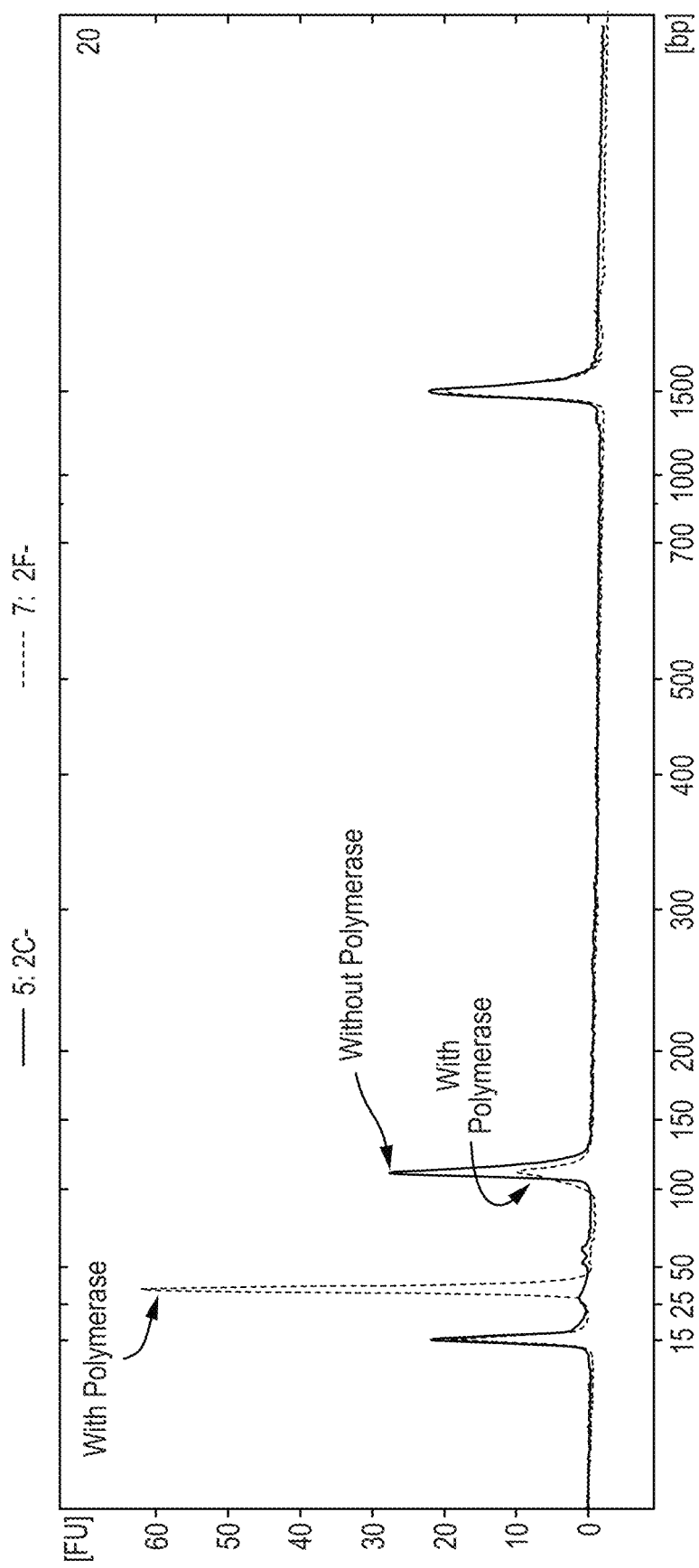
FIG. 11 is an Agilent 1000 chip trace showing the products produced when the polymerase Bst 3.0 is used to fill in an adapter formed by annealing RLA_Top-dA and RLA_btm_v2_SpeI. Traces with and without polymerase are shown.
Figure 12:
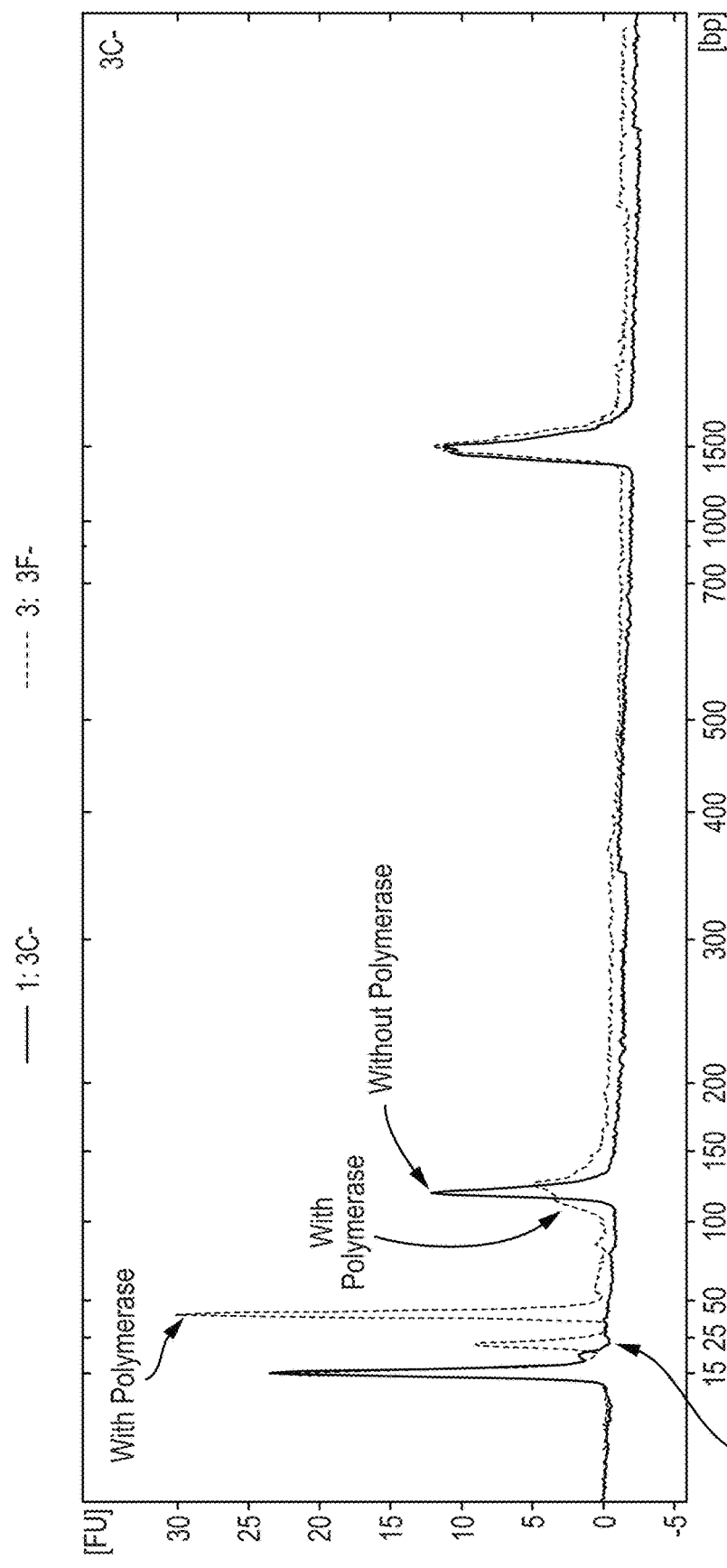
FIG. 12 is an Agilent 1000 chip trace showing the products obtained when the polymerase Bst 3.0 is used to fill-in an adapter formed by annealing RLA_Top-12bp1 and RLA_btm_v2_SpeI. Traces with and without polymerase are overlaid. The extra peak is the same size as one of the digestion products. It is therefore believed that a small amount of SpeI contaminated the sample.
Figure 13:
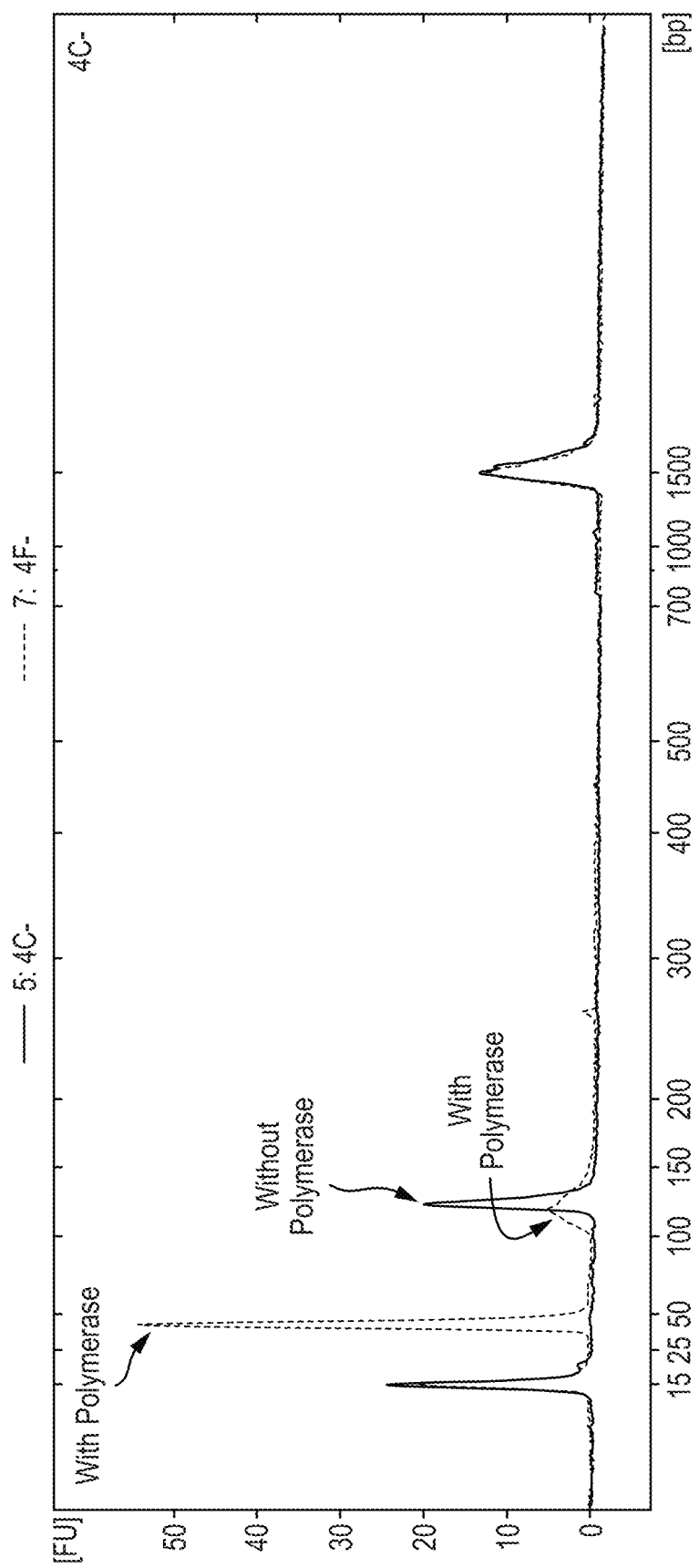
FIG. 13 is an Agilent 1000 chip trace showing the products obtained when the polymerase Bst 3.0 is used to fill in an adapter formed by annealing RLA_Top-12bp2 and RLA_btm_v2_SpeI. Traces with and without polymerase are overlaid.

1 μl of 100 nM annealed strands were run on an Agilent 1000 chip to determine adapter size (FIG. 9).

Adapters were tested for ability to act as a template for rolling linear amplification as follows. The reagents shown in the table below were mixed and incubated at 65° C. for 5 mins. 1 μl of 100 nM product was run on an Agilent 1000 chip to determine fill-in.

| Reagent | Control | Fill-in | Final |
|---|---|---|---|
| Water | 3.8 | 3.6 | |
| Adapter (10 μM) | 0.5 | 0.5 | 1 μM |
| 10× isothermal buffer | 0.5 | 0.5 | |
| 10 mM dNTPs | 0.2 | 0.2 | |
| Bst 3.0 | | 0.2 | |
| Total | 5 | 5 | |

For all adapters, the disappearance of the band corresponding to adapter (between approximately 100-150 bp on the x-axis) in the traces without polymerase can be observed (FIGS. 10-13). In addition, in all cases there is an appearance of a new band in the traces with polymerase (between approximately 25-50 bp on the x-axis), which is the putative fill-in product.

Adapters and fill-in products were subjected to SpeI digestion to determine if rolling linear amplification had occurred. Adapter or fill-in product was diluted to 200 nM in a 20 μl reaction containing 1×NEB CutSmart buffer and 5 U SpeI, before being incubated for 30 minutes at 37° C. 1 μl of reaction product was run on an Agilent 1000 chip to determine digestion.

Figure 14:
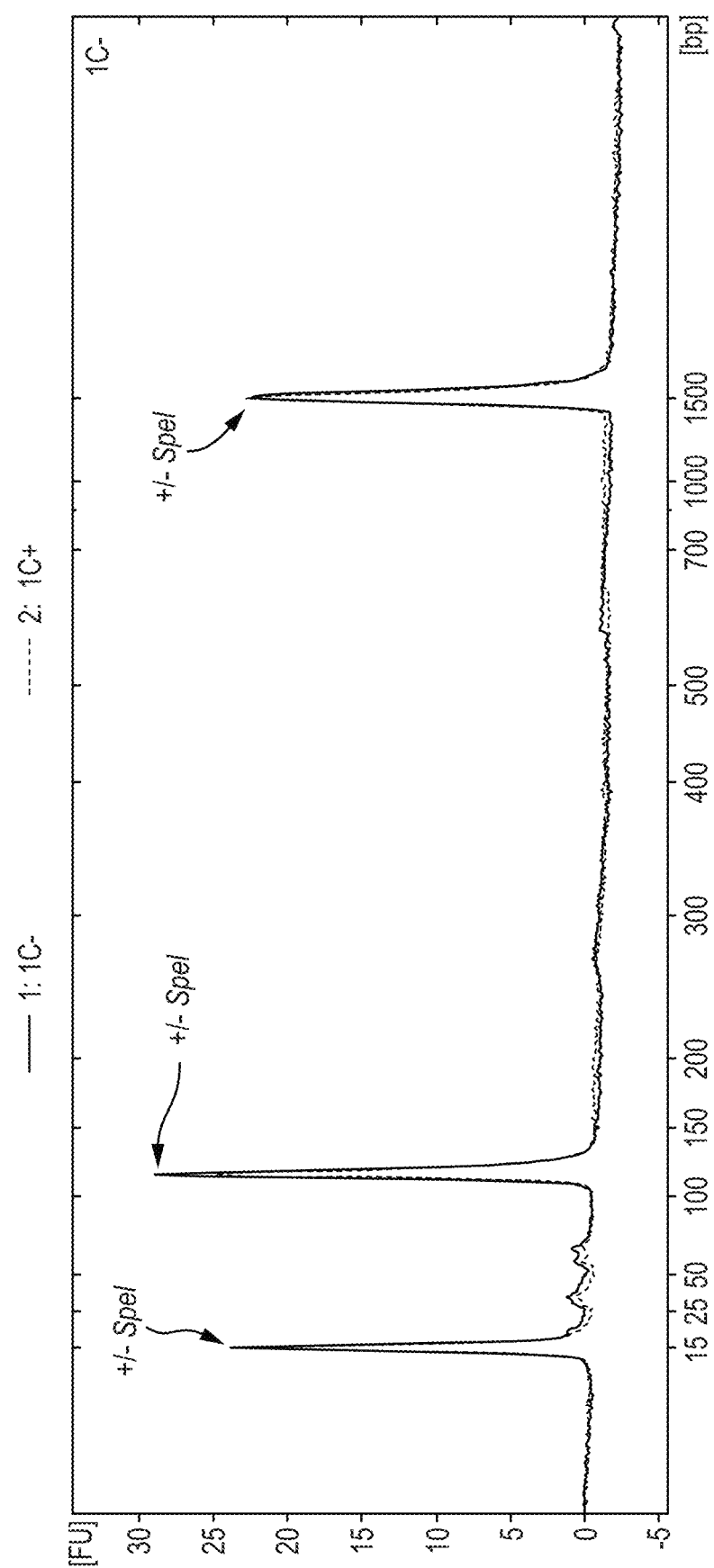
FIG. 14 is an example of the negative result for SpeI digestion seen for the adapter, RLA_Top and RLA_btm_v2_SpeI. Traces in the absence of SpeI and in presence of SpeI are overlaid.

None of the annealed strand combinations showed SpeI digestion, as illustrated for the strand combination RCA_Top and RLA_btm_v2_Spe1 in FIG. 14.

The results shown in FIG. 14 are representative of all adapters incubated with and without SpeI, in that no digestion was observed.

In contrast, all of the additional bands in the traces obtained in the presence of SpeI, i.e. the putative rolling linear amplification products, were digested by SpeI, indicating that rolling linear amplification had successfully occurred and these were indeed the amplification products. An example trace is shown in FIG. 15.

Example 5: Alternative Temperatures

Rolling linear amplification was performed over a range of different temperatures.

An adapter formed from RLA_Top and RLA_btm_v2 (5CATCGTCGTGAGTAGTGAACCGTAAGC) (SEQ ID NO: 10) were ligated onto an end-repaired and dA-tailed amplification product of lambda phage gDNA.

A 50 μl ligation consisting of: 1 μg of 3.6 kb strand, 200 nM adapter, 4,000 U T4 DNA ligase in 1× quick T4 ligase buffer was incubated for 10 mins at room temperature before a 0.6×SPRI purification with DNA being eluted in 50 μl of 10 mM Tris-HCl pH 7.5.

A 200 μl master mix was made consisting of: 40 μl recovered ligation product, 400 μM dNTPs and 2.4 U Bst3.0 in 1× Isothermal amplification buffer (NEB). Sample were aliquoted into 40 μl reactions and incubated for 30 mins at 50° C., 55° C., 60° C., 65° C. or 70° C. Following incubation samples were 0.6×SPRI purified and eluted in 12 μl of 10 mM Tris-HCl pH 7.5. 10 μl of recovered DNA was mixed with 1 μl of RAP from Oxford Nanopore Technologies' RAD004 kit and loaded onto a pre-prepared flowcell according to manufacturer's instructions. Sequenced strands were then analysed for the presence of repeats of the template and complement sections and the number of repeats plotted as a bar chart, showing rolling linear amplification took place over the range of temperatures tested (FIG. 16).

Example 6: Linear Amplification by Adaptor Ligation

Materials and Methods
Adaptors

Adaptors with the following sequences were prepared at 10 μM by slow cooling from 95° C. to 23° C. at 2° C. min$^{-1}$ in 10 mM Tris-HCl pH7.5, 50 mM NaCl, 0.5 mM EDTA.
Adaptor Sequences:

```
Rolling Linear Top Strand-dGTAC Control
                                       (SEQ ID NO: 1)
/5Phos/GCGTACTTTTTAGTACGCTTTTCGGCGTCTGCTTGGGTGTTTA
ACCT Rolling Linear Top Strand
                                       (SEQ ID NO: 2)
/5Phos/IZITAZTTTTTAITAZIZTTTTCGGCGTCTGCTTGGGTGTTTA
ACCT Rolling Linear Bottom Strand
                                       (SEQ ID NO: 3)
/5Phos/GGTTAAACACCCAAGCAGACGCCG
```

Ligation

Ligation reactions were prepared as follows and left at room temperature for 10 minutes:

| | |
|---|---|
| Adaptor (10 μM) | 5 μl |
| DNA fragment (End-repaired and dA-tailed) | 500 ng |
| NEB Blunt T/A Master Mix 2× | 50 μl |
| Nuclease Free Water | To 100 μl |

Reaction products were purified using Agencourt AMPure XP beads (Beckman Coulter) according to manufacturer's protocol and eluted in 37.5 μl of 10 mM Tris-HCl pH7.5, 50 mM NaCl, 0.5 mM EDTA.
Amplification Rolling linear amplification reactions were prepared as follows and incubated at 65° C. for 60 minutes then 80° C. for 5 mins to heat inactivate:

| Ligated DNA (from above) | 15 μl |
| --- | --- |
| dNTPs (10 mM) | 2 μl |
| NEB BST 3.0 | 3 μl |
| Isothermal Amplification Buffer 10× | 5 μl |
| NEB ET SSB | 1 μl |
| Nuclease Free Water | To 50 μl |

Reaction products were purified using Agencourt AMPure XP beads (Beckman Coulter) according to manufacturer's protocol and eluted in 43 μl of 10 mM Tris-HCl pH7.5, 50 mM NaCl, 0.5 mM EDTA.

The results obtained were similar to the results obtained in Example 1 using Klenow Fragment polymerase, demonstrating successful rolling linear amplification with BST 3.0 polymerase.

The invention claimed is:

1. A method of amplifying a target polynucleotide, comprising:
   a) providing a template polynucleotide comprising a 5' hairpin, a target polynucleotide and a 3' hairpin, wherein the 5' hairpin comprises one or more non-canonical nucleotides;
   b) contacting the template polynucleotide with a polymerase and canonical nucleotides,
   c) extending
      the template polynucleotide, using the polymerase and canonical nucleotides, from the 3' hairpin to form a first extended polynucleotide comprising the 5' hairpin at its 5' end and the complement of the 5' hairpin at its 3' end, wherein the complement of the 5' hairpin forms a 3' hairpin; and
   d) extending
      the first extended polynucleotide, using the polymerase, from its 3' hairpin to form a second extended polynucleotide comprising the 5' hairpin at its 5' end and the complement of the 5' hairpin at its 3' end, wherein the complement of the 5' hairpin forms a 3' hairpin wherein the 5' hairpin comprises a selectively cleavable group and the method is terminated using an enzyme that cleaves the polynucleotide at the selectively cleavable group.

2. A method according to claim 1, wherein the polymerase extends the second extended polynucleotide from its 3' hairpin to form a third extended polynucleotide comprising the 5' hairpin at its 5' end and the complement of the 5' hairpin at its 3' end, wherein the complement of the 5' hairpin forms a 3' hairpin.

3. A method according to claim 2, wherein the polymerase extends the third extended polynucleotide from its 3' hairpin, and optionally any further extended polynucleotides produced by extending the third extended polynucleotide and/or by subsequent extensions, to produce further extended polynucleotides comprising the 5' hairpin at their 5' ends and the complement of the 5' hairpin at their 3' ends, wherein the complement of the 5' hairpin forms a 3' hairpin.

4. A method according to claim 1, wherein the polymerase is a strand displacing polymerase.

5. A method according to claim 1, wherein the method is carried out at a constant temperature.

6. A method according to claim 1, further comprising the initial step of preparing the template polynucleotide by primer hybridization and extension.

7. A method according to claim 6, wherein a target polynucleotide is amplified using: (i) a first primer comprising a 5' hairpin and a sequence at its 3' end that is complementary to a sequence in the 3' end of the first strand of the target polynucleotide; and (ii) a second primer comprising a 5' hairpin and a sequence at its 3' end that is complementary to a sequence in the 3' end of the second strand of the target polynucleotide.

8. A method according to claim 6, wherein the template polynucleotide is produced by PCR.

9. A method according to claim 6, wherein the template polynucleotide is produced using an isothermal amplification method using a strand displacing polymerase.

10. A method according to claim 1, further comprising adding sequencing adaptors to one or both ends of the extended polynucleotide.

* * * * *